(12) United States Patent
Chafeev et al.

(10) Patent No.: US 8,450,358 B2
(45) Date of Patent: May 28, 2013

(54) ENANTIOMERS OF SPIRO-OXINDOLE COMPOUNDS AND THEIR USES AS THERAPEUTIC AGENTS

(75) Inventors: Mikhail Chafeev, Burnaby (CA); Jianmin Fu, Coquitlam (CA); Jean-Jacques Cadieux, Burnaby (CA)

(73) Assignee: Xenon Pharmaceuticals Inc., Burnaby, BC (CA)

( * ) Notice: Subject to any disclaimer, the term of this patent is extended or adjusted under 35 U.S.C. 154(b) by 61 days.

(21) Appl. No.: 12/825,168

(22) Filed: Jun. 28, 2010

(65) Prior Publication Data

US 2010/0331386 A1    Dec. 30, 2010

Related U.S. Application Data

(60) Provisional application No. 61/221,424, filed on Jun. 29, 2009.

(51) Int. Cl.
*A01N 43/38* (2006.01)
*A61K 31/40* (2006.01)
*C07D 491/00* (2006.01)
*C07D 495/00* (2006.01)

(52) U.S. Cl.
USPC .......................................... 514/409; 548/410

(58) Field of Classification Search
None
See application file for complete search history.

(56) References Cited

U.S. PATENT DOCUMENTS

| | | | |
|---|---|---|---|
| 3,189,617 A | 6/1965 | Archer et al. | 260/319 |
| 3,723,459 A | 3/1973 | Paragamian | 260/325 |
| 3,845,770 A | 11/1974 | Theeuwes et al. | 128/260 |
| 4,045,576 A | 8/1977 | Welstead, Jr. et al. | 424/309 |
| 4,326,525 A | 4/1982 | Swanson et al. | 128/260 |
| 4,438,130 A | 3/1984 | Kaplan | 424/274 |
| 4,440,785 A | 4/1984 | Walsh | 424/317 |
| 4,670,566 A | 6/1987 | Walsh | 548/485 |
| 4,886,788 A | 12/1989 | Skuballa et al. | 514/58 |
| 4,935,446 A | 6/1990 | Imaki et al. | 514/530 |
| 5,023,265 A | 6/1991 | Scherlock et al. | 514/300 |
| 5,116,854 A | 5/1992 | Marfat | 514/365 |
| 5,182,289 A | 1/1993 | Ting et al. | 514/278 |
| 5,278,162 A | 1/1994 | Wilkerson | 514/252 |
| 5,296,478 A | 3/1994 | Teleha | 514/235.2 |
| 5,304,121 A | 4/1994 | Sahatjian | |
| 5,453,516 A | 9/1995 | Fischer et al. | 548/543 |
| 5,663,431 A | 9/1997 | Di Malta et al. | 562/828 |
| 5,686,624 A | 11/1997 | Di Malta et al. | 548/410 |
| 5,696,145 A | 12/1997 | Foulon et al. | 514/409 |
| 5,723,625 A | 3/1998 | Keplinger et al. | 548/408 |
| 5,726,322 A | 3/1998 | Di Malta et al. | 548/410 |
| 5,728,723 A | 3/1998 | Di Malta et al. | 514/418 |
| 5,763,471 A | 6/1998 | Fourtillan et al. | 514/409 |
| 5,767,128 A | 6/1998 | Guillaumet et al. | 514/300 |
| 5,776,936 A | 7/1998 | Lee et al. | 514/250 |
| 5,849,780 A | 12/1998 | Di Malta et al. | 514/409 |
| 5,886,026 A | 3/1999 | Hunter et al. | |
| 5,994,350 A | 11/1999 | Foulon et al. | 514/232.8 |
| 6,046,341 A | 4/2000 | Foulon et al. | 548/411 |
| 6,090,818 A | 7/2000 | Foulon et al. | 514/278 |
| 6,099,562 A | 8/2000 | Ding et al. | |
| 6,110,969 A | 8/2000 | Tani et al. | 514/530 |
| 6,225,347 B1 | 5/2001 | Buchmann et al. | 514/530 |
| 6,235,780 B1 | 5/2001 | Ohuchida et al. | 514/530 |
| 6,262,293 B1 | 7/2001 | Tani et al. | 560/18 |
| 6,288,119 B1 | 9/2001 | Ohuchida et al. | 514/573 |
| 6,355,627 B1 | 3/2002 | Ishida et al. | 514/58 |
| 6,414,153 B1 | 7/2002 | Kelly et al. | 546/113 |
| 6,670,357 B2 | 12/2003 | Leftheris et al. | 514/218 |
| 6,964,973 B2 | 11/2005 | Zhi et al. | 514/312 |
| 7,368,470 B2 | 5/2008 | Sundermann et al. | 514/415 |
| 7,700,641 B2 | 4/2010 | Chafeev et al. | 514/409 |
| 7,799,798 B2 | 9/2010 | Chafeev et al. | 514/278 |
| 2002/0039790 A1 | 4/2002 | Keplinger et al. | 435/371 |
| 2004/0038970 A1 | 2/2004 | Thurieau et al. | 514/234.2 |
| 2004/0167224 A1 | 8/2004 | Ozaki et al. | 514/616 |

(Continued)

FOREIGN PATENT DOCUMENTS

| | | | |
|---|---|---|---|
| CA | 2095718 A1 | 5/1992 | |
| CA | 2107348 A1 | 7/1993 | |

(Continued)

OTHER PUBLICATIONS

Stella et al. (Prodrugs: Challenges and Rewards, Part 1, 2007).*
Vippagunta et al. (Adv. Drug. Deliv. Rev., 48: 3-26, 2001).*
Patani et al. (Chem. Rev., 1996, 96, 3146-76).*
Hoffman, Organic Chemistry: An intermediate text, Second Edition, 2004.*
Goldberg, "The Significance of Molecular Type, Shape and Complementarity in Clathrate Inclusion," *Topics in Current Chemistry 149*: 1-44, 1988.
Guillaumet et al., "Synthese d'un analogue dioxinique du psoralene," *Tetrahedron Letters 29*(22): 2665-2666, 1988.

(Continued)

*Primary Examiner* — Anna Pagonakis
(74) *Attorney, Agent, or Firm* — Seed IP Law Group PLLC

(57) ABSTRACT

This invention is directed to the (S)-enantiomer of the compound of formula (I):

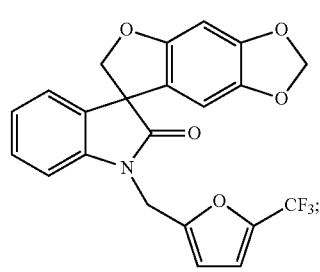

(I)

or a pharmaceutically acceptable solvate or prodrug thereof. This (S)-enantiomer is useful for the treatment of diseases or conditions, such as pain, which are ameliorated or alleviated by the modulation of voltage-gated sodium channels.

3 Claims, 6 Drawing Sheets

U.S. PATENT DOCUMENTS

| | | | |
|---|---|---|---|
| 2005/0004137 A1 | 1/2005 | Romano | 514/253.07 |
| 2005/0004138 A1 | 1/2005 | Romano | 514/253.07 |
| 2005/0014764 A1 | 1/2005 | Romano et al. | 514/253.06 |
| 2005/0020617 A1 | 1/2005 | Bastian et al. | 514/300 |
| 2005/0038036 A1 | 2/2005 | Romano et al. | 514/253.06 |
| 2005/0075351 A1 | 4/2005 | Berg et al. | 514/266.2 |
| 2005/0153998 A1 | 7/2005 | Ito et al. | 514/278 |
| 2005/0159473 A1 | 7/2005 | Sall et al. | 514/414 |
| 2005/0171186 A1 | 8/2005 | Fensome et al. | 514/418 |
| 2005/0256110 A1 | 11/2005 | Collins et al. | 514/224.2 |
| 2005/0256144 A1 | 11/2005 | Kath et al. | 514/275 |
| 2006/0247441 A1 | 11/2006 | Wilk | 548/408 |
| 2007/0049609 A1 | 3/2007 | Broka et al. | 514/269 |
| 2007/0072831 A1 | 3/2007 | Cai et al. | 514/80 |
| 2007/0105820 A1 | 5/2007 | Chafeev et al. | 514/80 |
| 2007/0299102 A1 | 12/2007 | Felding et al. | 514/299 |
| 2008/0103151 A9 | 5/2008 | Chafeev et al. | 514/248 |
| 2010/0099728 A1 | 4/2010 | Chafeev et al. | 514/409 |
| 2010/0125072 A1 | 5/2010 | Chafeev et al. | 514/232.8 |
| 2010/0130487 A1 | 5/2010 | Chafeev et al. | 514/232.8 |
| 2010/0137299 A1 | 6/2010 | Chafeev et al. | 514/232.8 |
| 2010/0160291 A1 | 6/2010 | Chafeev et al. | 514/211.09 |
| 2010/0160362 A1 | 6/2010 | Cadieux et al. | 514/278 |
| 2010/0173967 A1 | 7/2010 | Chafeev et al. | 514/409 |
| 2011/0034500 A1 | 2/2011 | Chafeev et al. | 514/278 |
| 2011/0086899 A1 | 4/2011 | Winters et al. | 514/409 |
| 2011/0087027 A1 | 4/2011 | Cadieux et al. | 546/15 |
| 2011/0251224 A1 | 10/2011 | Chafeev et al. | 514/278 |
| 2011/0269788 A1 | 11/2011 | Cadieux et al. | 514/278 |

FOREIGN PATENT DOCUMENTS

| | | |
|---|---|---|
| CA | 2129215 A1 | 1/1995 |
| CA | 2 274 898 A1 | 6/1998 |
| CA | 2 450 550 A1 | 1/2003 |
| CA | 2 466 915 A1 | 8/2003 |
| CA | 2 487 494 A1 | 12/2003 |
| CA | 2 235 686 C | 6/2007 |
| DE | 1 956 237 A | 5/1971 |
| DE | 2113343 A1 | 9/1972 |
| EP | 0 147 805 A2 | 7/1985 |
| EP | 0 164 860 A1 | 12/1985 |
| EP | 0 175 551 A1 | 3/1986 |
| EP | 0 608 058 A1 | 7/1994 |
| EP | 1 422 217 A2 | 5/2004 |
| EP | 1 557 166 A1 | 7/2005 |
| FR | 2 722 195 A1 | 1/1996 |
| JP | 10-95766 A | 4/1998 |
| JP | 2003-505388 | 2/2003 |
| WO | WO 86/03749 A1 | 7/1986 |
| WO | WO 91/01306 A1 | 2/1991 |
| WO | WO 91/04974 A1 | 4/1991 |
| WO | WO 91/06545 A1 | 5/1991 |
| WO | WO 92/09577 A1 | 6/1992 |
| WO | WO 93/12786 A1 | 7/1993 |
| WO | WO 93/15051 A1 | 8/1993 |
| WO | WO 94/03427 A1 | 2/1994 |
| WO | WO 95/06688 A1 | 3/1995 |
| WO | WO 95/14667 A1 | 6/1995 |
| WO | WO 97/15556 A1 | 5/1997 |
| WO | WO 97/36895 A1 | 10/1997 |
| WO | WO 98/25901 A1 | 6/1998 |
| WO | WO 98/50016 A2 | 11/1998 |
| WO | WO 00/06556 A1 | 2/2000 |
| WO | WO 00/71129 A1 | 11/2000 |
| WO | WO 01/05790 A1 | 1/2001 |
| WO | WO 01/38564 A2 | 5/2001 |
| WO | WO 01/38564 A3 | 5/2001 |
| WO | WO 01/74775 A1 | 10/2001 |
| WO | WO 02/30868 A1 | 4/2002 |
| WO | WO 02/38544 A2 | 5/2002 |
| WO | WO 03/000677 A1 | 1/2003 |
| WO | WO 03/037274 A2 | 5/2003 |
| WO | WO 03/037890 A2 | 5/2003 |
| WO | WO 03/064425 A1 | 8/2003 |
| WO | WO 03/078394 A1 | 9/2003 |
| WO | WO 03/106457 A1 | 12/2003 |
| WO | WO 2004/000225 A2 | 12/2003 |
| WO | WO 2004/000227 A2 | 12/2003 |
| WO | WO 2004/048320 A1 | 6/2004 |
| WO | WO 2005/011657 A2 | 2/2005 |
| WO | WO 2005/016913 A1 | 2/2005 |
| WO | WO 2005/019208 A1 | 3/2005 |
| WO | WO 2005/035498 A1 | 4/2005 |
| WO | WO 2005/092304 A2 | 10/2005 |
| WO | WO 2005/092895 A2 | 10/2005 |
| WO | WO 2005/097107 A2 | 10/2005 |
| WO | WO 2005/097122 A2 | 10/2005 |
| WO | WO 2005/099689 A1 | 10/2005 |
| WO | WO 2005/104711 A2 | 11/2005 |
| WO | WO 2005/105753 A2 | 11/2005 |
| WO | WO 2005/110992 A1 | 11/2005 |
| WO | WO 2005/111024 A1 | 11/2005 |
| WO | WO 2006/012173 A1 | 2/2006 |
| WO | WO 2006/017075 A1 | 2/2006 |
| WO | WO 2006/023107 A1 | 3/2006 |
| WO | WO 2006/023109 A1 | 3/2006 |
| WO | WO 2006/049290 A1 | 5/2006 |
| WO | WO 2006/055752 A2 | 5/2006 |
| WO | WO 2006/087019 A1 | 8/2006 |
| WO | WO 2006/091646 A2 | 8/2006 |
| WO | WO 2006/110654 A1 | 10/2006 |
| WO | WO 2006/110917 A2 | 10/2006 |
| WO | WO 2006/113864 A2 | 10/2006 |
| WO | WO 2006/113875 A2 | 10/2006 |
| WO | WO 2008/046046 A1 | 4/2008 |
| WO | WO 2008/046049 A1 | 4/2008 |
| WO | WO 2008/046065 A1 | 4/2008 |
| WO | WO 2008/046082 A2 | 4/2008 |
| WO | WO 2008/046083 A2 | 4/2008 |
| WO | WO 2008/046084 A2 | 4/2008 |
| WO | WO 2008/046087 A2 | 4/2008 |
| WO | WO 2008/060789 A2 | 5/2008 |
| WO | WO 2008/117050 A1 | 10/2008 |
| WO | WO 2010/045197 A1 | 4/2010 |
| WO | WO 2010/045251 A2 | 4/2010 |
| WO | WO 2010/053998 A1 | 5/2010 |
| WO | WO 2010/078307 A1 | 7/2010 |
| WO | WO 2010/132352 A2 | 11/2010 |
| WO | WO 2011/002708 A1 | 1/2011 |
| WO | WO 2011/047173 A2 | 4/2011 |
| WO | WO 2011/047174 A1 | 4/2011 |
| WO | WO 2011/106729 A2 | 9/2011 |

OTHER PUBLICATIONS

MacNicol, "Clathrates and Molecular Inclusion Phenomena," *Chemical Society Reviews* 7(1): 65-87, 1978.

Pouton, "Lipid formulations for oral administration of drugs: non-emulsifying, self-emulsifying and 'self-microemulsifying' drug delivery systems," *European Journal of Pharmaceutical Sciences* 11(Suppl 2): S93-S98, 2000.

Saenger, "Cyclodextrin Inclusion Compounds in Research and Industry," *Angew. Chem. Int. Ed. Engl 19*: 344-362, 1980.

Sircar et al., "Synthesis and SAR of N-Benzoyl-1-Biphenylalanine Dervatives: Discovery of TR-14035, a Dual $\alpha_4\beta_7/\alpha_4\beta_1$ Integrin Antagonist," *Bioorganic & Medicinal Chemistry Letters 10*: 2051-2066, 2002.

Weber and Czugler, "Functional Group Assisted Clathrate Formation—Scissor-Like and Roof-Shaped Host Molecules," *Topics in Current Chemistry 149*: 45-135, 1988.

Chafeev et al., entitled Spiro-Oxindole Compounds and Their Uses as Therapeutic Agents, Office Action dated Feb. 4, 2011, for U.S. Appl. No. 12/650,196, 31 pages.

Chafeev et al., entitled Spiro-Oxindole Compounds and Their Uses as Therapeutic Agents, Amendment and Winther Declaration dated May 4, 2011, for U.S. Appl. No. 12/650,196, 197 pages.

Sun et al., entitled Spiro-Oxindole Compounds and Their Uses as Therapeutic Agents, Amendment dated Nov. 10, 2010, for U.S. Appl. No. 12/650,218, 28 pages.

Sun et al., entitled Spiro-Oxindole Compounds and Their Uses as Therapeutic Agents, Notice of Allowance mailed 1Dec. 13, 2010, for U.S. Appl. No. 12/650,218, 19 pages.

Sun et al., entitled Spiro-Oxindole Compounds and Their Uses as Therapeutic Agents, Supplemental Amendment dated Mar. 2, 2011, for U.S. Appl. No. 12/650,218, 3 pages.

Chafeev et al., entitled Spiroheterocyclic Compounds and Their Uses as Therapeutic Agents, Preliminary Amendment dated Oct. 25, 2010, for U.S. Appl. No. 12/855,514, 32 pages.

International Search Report and Written Opinion, mailed Apr. 1, 2011, for PCTAN PCT/US2010/052704, 12 pages.

Winters et al., entitled Pharmaceutical Compositions for Oral Administration, Preliminary Amendment dated Dec. 27, 2010, for U.S. Appl. No. 12/905,048, 9 pages.

International Search Report and Written Opinion, mailed Oct. 1, 2010, for PCTAN PCT/US2010/040187, 13 pages.

International Search Report and Written Opinion, mailed Oct. 6, 2010, for PCTAN PCT/US2009/060537, 18 pages.

International Preliminary Report on Patentability, mailed Apr. 19, 2011, for PCTAN PCT/US2009/060537, 11 pages.

International Preliminary Report on Patentability, mailed Apr. 19, 2011, for PCTAN PCT/US2009/060455, 7 pages.

Chafeev et al., entitled Spiro-Oxindole Compounds and Their Use as Therapeutic Agents, Office Action dated Apr. 1, 2011, for U.S. Appl. No. 12/577,799, 49 pages.

Adams et al., "Bicyclic N-Hydroxyurea Inhibitors of 5-Lipoxygenase: Pharmacodynamic, Pharmacokinetic, and in Vitro Metabolic Studies Characterizing N-Hydroxy-N-(2,3-dihydro-6-(phenylmethoxy)-3-benzofuranyl)urea," *J. Med. Chem.* 39(26): 5035-5046, 1996.

Akai, "Development of Novel Asymmetric Reactions Oriented to Next-Generation Enzymatic Organic Syntheses," *Yakugaku Zasshi* 123(11): 919-931, 2003.

Al-Thebeiti and El-Zohry, "A Facile Route for the Synthesis of Some New Spiro[indo-line-3,3'-indan]-2,1'-Dione Derivatives," *Heterocycles* 41(11): 2475-2480, 1995.

Alabaster et al., "The Synthesis of 5-Substituted 2,3-Dihydrobenzofurans," *Synthesis* 12: 950-952, Dec. 1988.

Alcaide et al., "Efficient Entry to Diversely Functionalized Spirocyclic Oxindoles from Isatins through Carbonyl-Addition/Cyclization Reaction Sequences," *J. Org. Chem.* 71(6): 2346-2351, 2006.

Alper et al., "Eine neuartige Methode zur Synthese von Spiro[pyrrolidin-3,3'-oxindolen]: katalysierte Ringerweiterung von Cyclopropanen mit Aldiminen," *Angew. Chem.* 111(21): 3379-3381, 1999.

Alper et al., "Facile, Novel Methodology for the Synthesis of Spiro[pyrrolidin-3,3'-oxindoles]: Catalyzed Ring Expansion Reactions of Cyclopropanes by Aldimines," *Angew. Chem. Int. Ed.* 38(21): 3186-3189, 1999.

Anger et al., "Medicinal Chemistry of Neuronal Voltage-Gated Sodium Channel Blockers," *Journal of Medicinal Chemistry* 44(2): 115-137, Jan. 18, 2001.

Autrey and Tahk, "The Synthesis and Stereochemistry of Some Isatylideneacetic Acid Derivatives," *Tetrahedron* 23: 901-917, 1967.

Bacher et al., "Oxindole alkaloids from *Uncaria tomentosa* induce apoptosis in proliferating, G0/G1-arrested and bcl-2-expressing acute lymphoblastic leukaemia cells," *British Journal of Haematology* 132: 615-622, 2005.

Banfi et al., "High Diastereoface Selection in an Ester Enolate Addition to α-Alkoxy Aldehydes: Stereoselective Synthesis of α-Methylene-β-hydroxy-γ-alkoxy Esters," *J. Org. Chem.* 49: 3784-3790, 1984.

Basavaiah et al., "$TiCl_4$ catalyzed tandem construction of C—C and C—O bonds: a simple and one-pot atom-economical stereoselective synthesis of spiro-oxindoles," *Chem. Commun.* 2621-2623, 2005.

Bean et al., "Lidocaine Block of Cardiac Sodium Channels," *J. Gen. Physiol.* 81: 613-642, May 1983.

Bennett and Xie, "A peripheral mononeuropathy in rat that produces disorders of pain sensation like those seen in man," *Pain* 33: 87-107, 1988.

Beyersbergen Van Henegouwen et al., "First Total Synthesis of *ent*-Gelsedine via a Novel Iodide-Promoted Allene *N*-Acyliminium Ion Cyclization," *J. Org. Chem.* 65(24): 8317-8325, 2000.

Beyersbergen Van Henegouwen et al., "Total Synthesis of (+)-Gelsedine," *Angew. Chem. Int. Ed.* 38(15): 2214-2217, 1999.

Billert and Beckert, "Beiträge zur Chemie der Pyrido[1,2-α]pyrazine—Reaktivität gegenüber Heterocumulenen der Kohlensäurereihe und Ketenen," *J. Prakt. Chem.* 341(4): 332-341, 1999.

Binder et al., "Disease mechanisms in neuropathic itch," *Nature Clinical Practice/Neurology* 4(6): 329-337, Jun. 2008.

Blair and Bean, "Roles of Tetrodotoxin (TTX)-Sensitive $Na^+$ Current, TTX-Resistant $Na^+$ Current, and $Ca^{2+}$ Current in the Action Potentials of Nociceptive Sensory Neurons," *Journal of Neuroscience* 22(23): 10277-10290, Dec. 1, 2002.

Bond et al., "Cyclopiamines A and B, Novel Oxindole Metabolites of *Penicillium cyclopium* Westling," *Journal of the Chemical Society, Perkin Transaction 1: Organic and Rio-Organic Chemistry* 7: 1751-1761, 1979.

Brackenbury and Djamgoz, "Activity-dependent regulation of voltage-gated $Na^+$ channel expression in Mat-LyLu rat prostate cancer cell line," *J. Physiol.* 573.2: 343-356, 2006.

Bramson et al., "Oxindole-Based Inhibitors of Cyclin-Dependent Kinase 2 (CDK2): Design, Synthesis, Enzymatic Activities, and X-ray Crystallographic Analysis," *J. Med. Chem.* 44: 4339-4358, 2001.

Braude and Lindwall, "Condensations of Isatin with Acetone by the Knoevenagel Method," *Journal of the American Chemical Society* 55: 325-327, Jan. 1933.

Caldwell et al., "Sodium channel $Na_v1.6$ is localized at nodes of Ranvier, dendrites, and synapses," *PNAS* 97(10): 5616-5620, May 9, 2000.

Cañas-Rodriguez and Leeming, "N-Phenyl-2-indolinones and N-Phenylindolines. A New Class of Antidepressant Agents," *Journal of Medicinal Chemistry* 15(7): 762-770, 1972.

Capilla et al., "Synthesis of isoquinolines and tetrahydroisoquinolines as potential antitumour agents," *Tetrahedron* 57: 8297-8303, 2001.

Carlson et al., "Potential hypolipidemic agents: VI. Syntheses of some new halo-substituted pyridine compounds. Effects on noradrenaline-stimulated free fatty acid mobilization," *Acta Pharm. Suecica* 9: 411-418, 1972.

Cassebaum and Liedel, "Beziehungen zwischen Konstitution und α-Aminosäure-dehydrogenasewirkung von Isatinen," *Journal für praktische Chemie* 4(12):91-95, 1960.

Cestèle and Catterall, "Molecular mechanisms of neurotoxin action on voltage-gated sodium channels," *Biochimie* 82: 883-892, 2000.

Chande et al., "Facile synthesis of active antitubercular, cytotoxic and antibacterial agents: a Michael addition approach," *European Journal of Medicinal Chemistry* 40: 1143-1148, 2005.

Chaplan et al., "Quantitative assessment of tactile allodynia in the rat paw," *Journal of Neuroscience Methods* 53: 55-63, 1994.

Chioni et al., "A novel adhesion molecule in human breast cancer cells: Voltage-gated $Na^+$ channel β1 subunit," *The International Journal of Biochemistry & Cell Biology* 41: 1216-1227, 2009.

Chung and Chung, "Sodium channels and neuropathic pain," *Novartis Found Symposium* 261: 19-31, 2004.

Clare et al., "Voltage-gated sodium channels as therapeutic targets," *Drug Discovery Today* 5(11): 506-520, Nov. 2000.

Claudi et al., "Synthesis and Dopamine Receptor Affinities of 2-(4-Fluoro-3-hydroxyphenyl)ethylamine and N-Substituted Derivatives," *J. Med. Chem.* 33: 2408-2412, 1990.

Coppola, "*N*-Arylation of Isatins. A Direct Route to *N*-Arylisatoic Anhydrides," *J. Heterocyclic Chem.* 24: 1249-1251, Sep./Oct. 1987.

Cossy et al., "A Convenient Route to Spiropyrrolidinyl-Oxindole Alkaloids via C-3 Substituted Ene-Pyrrolidine Carbamate Radical Cyclization," *Tetrahedron Letters* 39: 2331-2332, 1998.

Cox et al., "An *SCN9A* channelopathy causes congenital inability to experience pain," *Nature* 444: 894-898, Dec. 14, 2006.

Craner et al., "Molecular changes in neurons in multiple sclerosis: Altered axonal expression of $Na_v1.2$ and $Na_v1.6$ sodium channels and $Na^+/Ca^{2+}$ exchanger," *PNAS* 101(21): 8168-8173, May 25, 2004.

Cravotto et al., "Azomethine Ylide Cycloaddition/Reductive Heterocyclization Approach to Oxindole Alkaloids: Asymmetric Synthesis of (−)-Horsfiline," *J. Org. Chem.* 66(25): 8447-8453, 2001.

Creveling and Daly, "Batrachotoxinin A [$^3$H]Benzoate Binding to Sodium Channels," *Methods in Neurosciences* 8: 25-37, 1992.

Cube et al., "3-(2-Ethoxy-4-{4-[3-hydroxy-2-methyl-4-(3-methylbutanoyl)-phenoxy]butoxy}phenyl)propanoic acid: a brain penetrant allosteric potentiator at the metabotropic glutamate receptor 2 (mGluR2)," *Bioorganic & Medicinal Chemistry Letters* 15: 2389-2393, 2005.

Dallacker and Sanders, "Darstellung und Reaktionen von 5-(3'-Hydroxy-oxindol-3'-yl)-1,3-benzdioxole," *Chemiker-Zeitung* 110(11): 405-411, 1986.

Devers and Galer, "Topical Lidocaine Patch Relieves a Variety of Neuropathic Pain Conditions: An Open-Label Study," *Clinical Journal* 16(3): 205-208, Sep. 2000, obtained from URL=http://ovidsp.tx.ovid.com/spb/ovidweb.cgi, download date Apr. 18, 2008, 5 pages.

Dib-Hajj et al., "Genetics and Molecular Pathophysiology of $Na_v1.7$-Related Pain Syndromes," *Advances in Genetics* 63: 85-110, 2008.

Dib-Hajj et al., "NaN, a novel voltage-gated Na channel, is expressed preferentially in peripheral sensory neurons and down-regulated after axotomy," *Proc. Natl. Acad. Sci. USA* 95: 8963-8968, Jul. 1998.

Ding et al., "Structure-Based Design of Spiro-oxindoles as Potent, Specific Small-Molecule Inhibitors of the MDM2-p53 Interaction," *J. Med. Chem* 49(12): 3432-3435, 2006.

Diss et al., "A potential novel marker for human prostate cancer: voltage-gated sodium channel expression in vivo," *Prostate Cancer and Prostatic Diseases* 8: 266-273, 2005.

Do and Bean, "Subthreshold Sodium Currents and Pacemaking of Subthalamic Neurons: Modulation by Slow Inactivation," *Neuron* 39: 109-120, Jul. 3, 2003.

Domingo et al., "Studies on the Biosynthesis of Paraherquamide A and VM99955. A Theoretical Study of Intramolecular Diels—Alder Cycloaddition," *J. Org. Chem.* 68(7): 2895-2902, 2003.

Doyle et al., "Rhodium (II) Acetate and Nafion-H Catalyzed Decomposition of N-Aryldiazoamides. An Efficient Synthesis of 2(3H)-Indolinones," *J. Org. Chem* 53(5): 1017-1022, 1988.

Dubuisson and Dennis, "The Formalin Test: A Quantitative Study of the Analgesic Effects of Morphine, Meperidine, and Brain Stem Stimulation in Rats and Cats," *Pain* 4: 161-174, 1977.

Dutton et al., "A Total Synthesis of Gelsemine: Oxindole Spiroannelation," *J. Chem. Soc., Chem. Commun.* 765-766, 1994.

Dutton et al., "Synthesis of Hindered Spiro-Oxindoles by Photolysis of 1-(1-Alkenyl)bensotriazoles," *Tetrahedron* 55: 11927-11942, 1999.

El-Ahl, "Three-Component 1,3-Dipolar Cycloaddition Reactions in Synthesis of Spiro[pyrrolidine-2,3'-oxindoline] Derivatives," *Heteroatom Chemistry* 13(4): 324-329, 2002.

El-Gendy and Ahmedy, "Synthesis and Antimicrobial Activity of some New 2-Indolinone Derived Oximes and Spiro-Isoxazolines," *Arch. Pharm. Res.* 23(4): 310-314, 2000.

Ettinger and Argoff, "Use of Antiepileptic Drugs for Nonepileptic Conditions: Psychiatric Disorders and Chronic Pain," *Neurotherapeutics: The Journal of the American Society for Experimental NeuroTherapeutics* 4:75-83, Jan. 2007.

Feldman and Karatjas, "Extending Pummerer Reaction Chemistry. Asymmetric Synthesis of Spirocyclic Oxindoles via Chiral Indole-2-sulfoxides," *Org. Lett.* 8(18): 4137-4140, 2006.

Feldman et al., "Extending Pummerer Reaction Chemistry. Development of a Strategy for the Regio- and Stereoselective Oxidative Cyclization of 3-(ω-Nucleophile)-Tethered Indoles," *J. Org. Chem.* 70(16): 6429-6440, 2005.

Feldman and Vidulova, "Extending Pummerer Reaction Chemistry. Application to the Oxidative Cyclization of Indole Derivatives," *Organic Letters* 6(11): 1869-1871, 2004.

Fishman et al., "Intravenous Lidocaine for Treatment-resistant Pruritus," *American Journal of Medicine* 102: 584-585, Jun. 1997.

Flanagan et al., "Radical cyclisation reactions with indoles," *Tetrahedron Letters* 44: 1795-1798, 2003.

Fokas et al., "Solution Phase Synthesis of a Spiro[pyrrolidine-2,3'-oxindole] Library via a Three Component 1,3-Dipolar Cycloaddition Reaction," *Tetrahedron Letters* 39: 2235-2238, 1998.

Foster et al., "457. Furano-compounds. Part VII. A Synthesis of 2 : 3-Dihydropsoralene," *J. Chem. Soc.* 2254-2260, 1948.

Fraser et al., "Voltage-Gated Sodium Channel Expression and Potentiation of Human Breast Cancer Metastasis," *Clin. Cancer Res.* 11(15): 5381-5389, Aug. 1, 2005.

Fuchs and Funk, "Indol-2-one Intermediates: Mechanistic Evidence and Synthetic Utility. Total Syntheses of (±)-Flustramines A and C," *Org. Lett.* 7(4): 677-680, 2005.

Fuchs and See, "Basolateral amygdala inactivation abolishes conditioned stimulus- and heroin-induced reinstatement of extinguished heroin-seeking behavior in rats," *Psychopharmacology* 160: 425-433, 2002.

Fuji et al., "Direct Asymmetric Synthesis of Quaternary Carbon Centers via Addition-Elimination Process: Nitroolefination of α-Substituted δ-Lactones," *J. Am. Chem. Soc.* 111: 7921-7925, 1989.

Fujita et al., "The Beckmann Rearrangement by Means of Phosphoryl Chloride/N,N-Dimethylacetamide; A Novel and Convenient Method for Preparing Benzoxazoles," *Synthesis* 68-69, Jan. 1982.

Gálvez and García, "Synthesis of Isomeric β-Haloethylthienopyrroles," *J. Heterocyclic Chem.* 21: 393-395, Mar.-Apr. 1984.

Ganguly et al., "Solution- and solid-phase synthesis of enantiomerically pure spiro oxindoles," *Tetrahedron Letters* 43: 8981-8983, 2002.

Ganguly et al., "Synthesis of heterocyclic compounds using radical reactions and evidence for the formation of spiro radical intermediates," *Tetrahedron Letters* 45: 883-886, 2004. See also Ganguly et al., "Corrigendum to 'Synthesis of heterocyclic compounds using radical reactions and evidence for the formation of spiro radical intermediates,'" [*Tetrahedron Letters* 45: 883-886, 2004], *Tetrahedron Letters* 45: 3835, 2004.

Garden et al., "Investigation of the selective reduction of isatin derivatives. Synthesis of α-hydroxyacetophenone derivatives and ethyl spiro-3,3-(ethylenedioxy)-2-hydroxyindoline carboxylates," *Tetrahedron Letters* 44: 7617-7621, 2003.

Garden et al., "A versatile synthetic methodology for the synthesis of tryptophols," *Tetrahedron* 58: 8399-8412, 2002.

Goldberg et al., "Loss-of-function mutations in the $Na_v1.7$ gene underlie congenital indifference to pain in multiple human populations," *Clin. Genet.* 71: 311-319, 2007.

González-López de Turiso and Curran, "Radical Cyclization Approach to Spirocyclohexadienones," *Organic Letters* 7(1): 151-154, 2005.

Grigg et al., "Palladium Catalysed Ter- and Tetra-molecular Queuing Processes. One-pot Routes to 3-Spiro-2-Oxindoles and 3-Spiro-2(3H)-Benzofuranones," *Tetrahedron Letters* 37(5): 695-698, 1996.

Grigg et al., "Spiro-oxindoles via bimetallic [Pd(0)/Ag(I)] catalytic intramolecular Heck-1,3-dipolar cycloaddition cascade reactions," *Tetrahedron Letters* 43: 2605-2608, 2002.

Grigoryan et al., "Synthesis and antispasmodic activity of spiro[β-carbolineindolones] and spiro[indoleindolo[2,3-c]azepinones]," *Hayastani Kimiakan Handes* 58(3): 100-104, 2005, CAPLUS Database Accession No. 2005:876436, 4 pages, Abstract only.

Hains et al., "Upregulation of Sodium Channel $Na_v1.3$ and Functional Involvement in Neuronal Hyperexcitability Associated with Central Neuropathic Pain after Spinal Cord Injury," *Journal of Neuroscience* 23(26): 8881-8892, Oct. 1, 2003.

Hamann et al., "Motor disturbances in mice with deficiency of the sodium channel gene Scn8a show features of human dystonia," *Experimental Neurology* 184: 830-838, 2003.

Haufe et al., "The promiscuous nature of the cardiac sodium current," *Journal of Molecular and Cellular Cardiology* 42: 469-477, 2007.

Hiemstra et al., "Models of Folate Coenzymes—VIII: An Approach to Yohimbane Alkaloids Via Carbon-Fragment Transfer From $N^5$, $N^{10}$-Methylenetetrahydrofolate Models," *Tetrahedron* 39(23): 1981-1986, 1983.

Ikoma et al., "The neurobiology of itch," *Nature Reviews Neuroscience* 7: 535-547, Jul. 2006.

Inan et al., "Inhibitory effect of lidocaine on pain and itch using formalin-induced nociception and 5'-guanidinonaltrindole-induced scratching models in mice: Behavioral and neuroanatomical evidence," *European Journal of Pharmacology* 616: 141-146, 2009.

Iranpoor et al., "A novel method for the highly efficient synthesis of 1,2-benzisoxazoles under neutral conditions using the $Ph_3P/DDQ$ system," *Tetrahedron Letters* 47: 8247-8250, 2006.

Ishiyama et al., "Synthesis of Arylboronates via the Palladium(0)-Catalyzed Cross-Coupling Reaction of Tetra(alkoxo)diborons with Aryl Triflates," *Tetrahedron Letters* 38(19): 3447-3450, 1997.

Islip and White, "236. Some Reactions of 2-(3-Oxindolyl)ethylamines," *Journal of the Chemical Society* 1201-1204, 1964.

Itoh et al., "Introduction of a Hydroxy Group at the Para Position and N-Iodophenylation of N-Arylamides Using Phenyliodine(III) Bis(Trifluoracetate)," *J. Org. Chem.* 67: 7424-7428, 2002.

Jarvis et al., "A-803467, a potent and selective $Na_v1.8$ sodium channel blocker, attenuates neuropathic and inflammatory pain in the rat," *PNAS* 104(20): 8520-8525, May 15, 2007.

Jorgensen and Berteau, "Thyroxine Analogs. 21. o- and m-L-Thyroxine and Related Compounds," *Journal of Medicinal Chemistry* 14(12): 1199-1202, 1971.

Julian et al., "Studies in the Indole Series. VI. On the Synthesis of Oxytryptophan and Further Studies of 3-Alkylation of Oxindoles," *Journal of the American Chemical Society* 57: 2026-2029, Nov. 1935.

Julian et al., "Studies in the Indole Series. VIII. Yohimbine (Part 1). The Mechanism of Dehydrogenation of Yohimbine and Related Compounds," *Journal of the American Chemical Society* 70: 174-179, Jan. 1948.

Kaila et al., "Synthesis and Biological Evaluation of Quinoline Salicylic Acids as P-Selectin Antagonists," *J. Med. Chem.* 50: 21-39, 2007.

Kamara et al., "The First Direct Transformation of 2,2'-Dihydroxychalcones into Coumestans," *Tetrahedron* 55: 861-868, 1999.

Kamiya et al., "A Nonsense Mutation of the Sodium Channel Gene SCN2A in a Patient with Intractable Epilepsy and Mental Decline," *Journal of Neuroscience* 24(11): 2690-2698, Mar. 17, 2004.

Kang et al., "Pteropodine and isopteropodine positively modulate the function of rat muscarinic $M_1$ and $5-HT_2$ receptors expressed in *Xenopus* oocyte," *European Journal of Pharmacology* 444: 39-45, 2002.

Karp et al., "Preparation of 4-Hydroxy-2-trifluoromethylthiophene: A Novel Bioisostere of α,α,α-Trifluoro-m-cresol," *Synthesis* 8: 1078-1080, 2000.

Kende et al., "Intramolecular Radical Cyclization of Phenolic Enolates," *J. Am. Chem. Soc.* 110: 2210-2218, 1988.

Kim et al., "BACE1 regulates voltage-gated sodium channels and neuronal activity," *Nature Cell Biology* 9(7): 755-764, Jul. 2007.

Kim et al., "Design, synthesis, and evaluation of dioxane-based antiviral agents targeted against the Sindbis virus capsid protein," *Bioorganic & Medicinal Chemistry Letters* 15: 3207-3211, 2005.

King et al., "Hydroxy-quinoxalines and -phenazines, and Experiments on the Preparation of Hydroxyquinoxaline Di-N-oxides," *J. Chem. Soc.* 3012-3016, 1949.

Kirmse et al., "Intramolecular Reactivity of Arylcarbenes: Derivatives of o-Tolylcarbene," *J. Org. Chem.* 59: 3821-3829, 1994.

Klugbauer et al., "Structure and functional expression of a new member of the tetrodotoxin-sensitive voltage-activated sodium channel family from human neuroendocrine cells," *EMBO J.* 14(6): 1084-1090, 1995.

Kobayashi and Furukawa, "Studies on Indole Derivatives. I. Synthesis of 3-Phenyl-9H-pyridazino-[3,4-b]indole Derivatives," *Chemical & Pharmaceutical Bulletin* 12(10): 1129-1135, Oct. 1964.

Kollmar et al., "2-Amino-3-Fluorobenzoic Acid [Benzoic acid, 2-amino-3-fluoro-]," *Organic Syntheses, Coll.* 79: 196, 2002, 5 pages.

Kornet and Thio, "Oxindole-3-spiropyrrolidines and -piperidines. Synthesis and Local Anesthetic Activity," *Journal of Medicinal Chemistry* 19(7): 892-898, 1976.

Kotha et al., "Recent applications of the Suzuki-Miyaura cross-coupling reaction in organic synthesis," *Tetrahedron* 58: 9633-9695, 2002.

Kubo et al., "Michael Additions of Indoles to 2-oxoindolin-3-ylidene Ketones," *Heterocycles* 4(10): 1675-1680, 1976.

Kumar et al., "A New Route to Spiropyrrolidinyl-oxindole Alkaloids via Iodide Ion Induced Rearrangement of [(N-Aziridinomethylthio)methylene]-2-oxindoles," *Organic Letters* 3(26): 4193-4196, 2001.

Kuzma et al., "Progress in the Development of Ultra-Long-Acting Local Anesthetics," *Regional Anesthesia* 22(6): 543-551, Nov.-Dec. 1997.

Lackey and Sternbach, "Synthesis of Substituted Quinoline-4-carboxylic Acids," *Synthesis*: 993-997, Oct. 1993.

Lai et al., "The role of voltage-gated sodium channels in neuropathic pain," *Current Opinion in Neurobiology* 13:291-297, 2003.

Laus, "Kinetics of isomerization of tetracyclic spiro oxindole alkaloids," *J. Chem. Soc., Perkin Trans.* 2: 315-317, 1998.

Laus et al., "Analysis of the kinetics of isomerization of spiro oxindole alkaloids," *J. Chem. Soc., Perkin Trans.* 2: 1931-1936, 1996.

Lee-Son et al., "Stereoselective Inhibition of Neuronal Sodium Channels by Local Anesthetics," *Anesthesiology* 77: 324-335, 1992.

Lerchner and Carreira, "Synthesis of (±)-Strychnofoline via a Highly Convergent Selective Annulation Reaction," *Chem. Eur. J.* 12: 8208-8219, 2006.

Leuwer et al., "An improved model for the binding of lidocaine and structurally related local anaesthetics to fast-inactivated voltage-operated sodium channels, showing evidence of cooperativity," *British Journal of Pharmacology* 141(1): 47-54, 2004.

Lindemann et al., "Zur Kenntnis der Indoxazene," *Justus Liebigs Annalen der Chemie* 456: 284-311, 1927.

Lindwall and MacLennan, "A Condensation of Acetophenone with Isatin by the Knoevenagel Method," *Journal of the American Chemical Society* 54: 4739-4744, Dec. 1932.

Liu et al., "Mutations in Cardiac Sodium Channels: Clinical Implications," *Am. J. Pharmacogenomics* 3(3): 173-179, 2003.

Lossin et al., "Molecular Basis of an Inherited Epilepsy," *Neuron* 34: 877-884, Jun. 13, 2002.

Loudon and Ogg, "2:3-Dihydro-3-oxobenz-1:4-oxazines," *J. Chem. Soc.*: 739-744, 1955.

Lutz and Clark, "Acid-Catalyzed Rearrangements of the γ-(Methylanilino)lactone of cis-β-(p-Bromobenzoyl)-β-methylacrylic Acid, and of trans-β-(p-Bromobenzoyl)acrylic Methylanilide, to Oxindoles," *J. Org. Chem.* 25: 193-196, Feb. 1960.

Lyalin et al., [title unavailable], *Zhurnal Organicheskoi Khimii* 20(4): 846-849, 1984.

Ma and Cai, "N,N-Dimethyl Glycine-Promoted Ullmann Coupling Reaction of Phenols and Aryl Halides," *Organic Letters* 5(21): 3799-3802, 2003.

Maercker and Theysohn, "Versuche zur Umlagerung von 2-Cyclopropyl-äthyl-Anionen," *Liebigs Ann. Chem.* 759: 132-157, 1972.

Maginnity and Gaulin, "Derivatives of o-, m- and p-Aminobenzotrifluoride," *J. Am. Chem. Soc.* 73: 3579-3580, Aug. 1951.

Majumdar et al., "1-Alkylisatins via Aldol-Retro-aldol Condensation," *J. Chem. Research (S)*, 460-461, 1996.

Mann et al., "The Synthesis of Lignans and Related Structures using Quinodimethanes and Isobenzofurans: Approaches to the Podophyllins," *J. Chem. Soc. Perkin Trans. I*: 2081-2088, 1984.

Mannaioni et al., "Tryptophan Metabolism and Hepatic Encephalopathy. Studies on the Sedative Properties of Oxindole," *Advances in experimental medicine and biology* 467: 155-167, 1999.

Mao and Baldwin, "New Spirocyclic Oxindole Synthesis Based on a Hetero Claisen Rearrangement," *Organic Letters* 6(14): 2425-2428, 2004.

Mao and Chen, "Systemic lidocaine for neuropathic pain relief," *Pain* 87: 7-17, 2000.

Marcantonio et al., "An Investigation into Causes and Effects of High Cyanide Levels in the Palladium-Catalyzed Cyanation Reaction," *Organic Letters* 6(21): 3723-3725, 2004.

Marti and Carreira, "Construction of Spiro[pyrrolidine-3,3'-oxindoles]—Recent Applications to the Synthesis of Oxindole Alkaloids," *Eur. J. Org. Chem.* 2209-2219, 2003.

Marti and Carreira, "Total Synthesis of (−)-Spirotryprostatin B: Synthesis and Related Studies," *J. Am. Chem. Soc.* 127(32): 11505-11515, 2005.

McMurtrey and Daves, Jr., "König's Adducts of N-Alkyl(aryl)aminoethanols and Quinones. 3,4-Dihydro-4-alkyl(aryl)-8a-hydroxy-2H-1,4,benzoxazin-6(8aH)-ones," *J. Org. Chem.* 35(12): 4252-4253, 1970.

McNeal et al., "[$^3$H]Batrachotoxinin A 20α-Benzoate Binding to Voltage-Sensitive Sodium Channels: A Rapid and Quantitative Assay for Local Anesthetic Activity in a Variety of Drugs," *J. Med. Chem.* 28(3): 381-388, 1985.

Meisler et al., "Sodium channel gene family: epilepsy mutations, gene interactions and modifier effects," *J. Physiol.* 588.11: 1841-1848, 2010.

Miyake et al., "Preparation and Synthetic Applications of 2-Halotryptamines: Synthesis of Elacomin and Isoelacomine," *Organic Letters* 6(5): 711-713, 2004.

Miyamoto et al., "Highly Diastereoselective One-Pot Synthesis of Spirocyclic Oxindoles through Intramolecular Ullmann Coupling and Claisen Rearrangement," *Angew. Chem. Int. Ed.* 45: 2274-2277, 2006.

Miyaura and Suzuki, "Palladium-Catalyzed Cross-Coupling Reactions of Organoboron Compounds," *Chem. Rev.* 95: 2457-2483, 1995.

Morie et al., "Asymmetric Synthesis of the Enantiomers of 2-Aminomethyl-4-(4-Fluorobenzyl)morpholine, an Intermediate of Mosapride, a Gastroprokinetic Agent," *Heterocycles* 38(5): 1033-1040, 1994.

Morinville et al., "Distribution of the Voltage-Gated Sodium Channel $Na_v1.7$ in the Rat: Expression in the Autonomic and Endocrine Systems," *Journal of Comparative Neurology* 504: 680-689, 2007.

Morton et al., "Novel solid-phase synthesis of 1,5-benzothiazepine-4-one derivatives," *Tetrahedron Letters* 41: 3029-3033, 2000.

Muci and Buchwald, "Practical Palladium Catalysts for C—N and C—O Bond Formation," *Topics in Current Chemistry* 219: 131-209, 2002.

Muhammad et al., "Two stereoisomeric pentacyclic oxindole alkaloids from *Uncaria tomentosa*; uncarine C and uncarine E," *Acta Cyst. C57*: 480-482, 2001.

Nagakura et al., "Allodynia and Hyperalgesia in Adjuvant-Induced Arthritic Rats: Time Course of Progression and Efficacy of Analgesics," *The Journal of Pharmacology and Experimental Therapeutics* 306(2): 490-497, 2003, obtained from URL=http://jpet.aspetjournals.org, download date Aug. 14, 2009.

Nagamura and Saito, "Antitumor Antibiotics: Duocarmycins," *Chemistry of Heterocyclic Compounds* 34(12): 1386-1405, 1998.

Nagamura et al., "Wagner-Meerwein Rearrangement of Duocarmycins," *Chem. Pharm. Bull.* 44(5): 933-939, May 1996.

Nair et al., "Formal dipolar cycloaddition of allylsilanes to *o*-quinonoid compounds: a convenient route to benzofused and spirofused heterocycles," *Tetrahedron Letters* 43: 5349-5351, 2002.

Nair et al., "N-Heterocyclic Carbene Catalyzed Reaction of Enals and 1,2-Dicarbonyl Compounds: Stereoselective Synthesis of Spiro γ-Butyrolactones," *Org. Lett.* 8(3): 507-509, 2006.

Nakamura et al., "Cancer preventive agents, Part 2: Synthesis and evaluation of 2-phenyl-4-quinolone and 9-oxo-9,10-dihydroacridine derivatives as novel antitumor promoters," *Bioorganic & Medicinal Chemistry* 13: 4396-4401, 2005.

Newkome et al., "α-Methyl Functionalization of Electron-Poor Heterocycles: Free Radical Chlorination," *Synthesis* 676-679, Aug. 1984.

Nicolaus, *Decision Making in Drug Research*, Raven Press, New York, 1983, Franz Gross (ed.), "Symbiotic Approach to Drug Design," pp. 173-186.

Niemann et al., "The Synthesis of 3'-Fluoro-*dl*-thyronine and Some of its Iodinated Derivatives," *J. Am. Chem. Soc.* 63: 609-611, Feb. 1941.

Oguri et al., "Amino Acids and Peptides. XXVIII. A New Synthesis of α-Amino Acid Derivatives by Alkylation of Schiff Bases derived from Glycine and Alanine," *Chem. Pharm. Bull.* 25(9): 2287-2291, 1977.

Okita and Isobe, "Synthesis of the Pentacyclic Intermediate for Dynemicin A and Unusual Formation of Spiro-oxindole Ring," *Tetrahedron* 50(38): 11143-11152, 1994.

Onishi et al., "Concise, Asymmetric Total Synthesis of Spirotryprostatin A," *Organic Letters* 5(17): 3135-3137, 2003.

Onishi et al., "Concise, asymmetric total synthesis of spirotryprostatin A," *Tetrahedron* 60: 9503-9515, 2004.

Orlova et al., "Synthesis of 2,3,4,5-Tetrahydro-1,5-Benzox(and Thi)azepines and Their Utilization for the Preparation of Condensed Indoles," Translated from *Khimiya Geterotsiklicheskikh Soedinenii* 9: 1262-1266, Sep. 1975, 5 pages.

Overman and Watson, "Diasteroselection in the Formation of Spirocyclic Oxindoles by the Intramolecular Heck Reaction," *J. Org. Chem* 71: 2587-2599, 2006.

Papale et al., "Heterozygous mutations of the voltage-gated sodium channel *SCN8A* are associated with spike-wave discharges and absence epilepsy in mice," *Human Molecular Genetics* 18(9): 1633-1641, 2009.

Pereira et al., "Severe epilepsy, retardation, and dysmorphic features with a 2q deletion including *SCN1A* and *SCN2A*," *Neurology* 63: 191-192, 2004.

Pietra and Tacconi, "α-Alkyl- and α-aryl-N-methyltryptamines," *Farmaco, Edizione Scientifica* 14: 854-866, 1959, CAPLUS Database Accession No. 1960:50362, 1 page, Abstract only.

Popp and Pajouhesh, "Potential Anticonvulsants IV: Condensation of Isatin with Benzoylacetone and Isopropyl Methyl Ketone," *Journal of Pharmaceutical Sciences* 71(9): 1052-1054, Sep. 1982.

Popp et al., "Synthesis of Potential Anticonvulsants: Consensation of Isatins with Acetone and Related Ketones," *Journal of Pharmaceutical Sciences* 69(10): 1235-1237, Oct. 1980.

Popp, "Potential Anticonvulsants. V. The Condensation of Isatins with C-Acetyl Heterocyclic Compounds," *J. Heterocyclic Chem.* 19: 589-592, May-Jun. 1982.

Priest, "Future potential and status of selective sodium channel blockers for the treatment of pain," *Current Opinion in Drug Discovery & Development* 12(5): 682-692, 2009.

Puopolo et al., "Roles of Subthreshold Calcium Current and Sodium Current in Spontaneous Firing of Mouse Midbrain Dopamine Neurons," *Journal of Neuroscience* 27(3): 645-656, Jan. 17, 2007.

Raj and Raghunathan, "A Novel Entry into a New Class of Spiro Heterocyclic Framework: A Facile Synthesis of Dispiro[oxindole-1,2,3,4-tetrahydro-naphthalen-1-one]pyrrolidines and Spiro[1,2,3,4-tetrahydro-naphthalen-1-one]pyrrolidines," *Synthetic Communications* 33(7): 1131-1139, 2003.

Raj and Raghunathan, "A novel entry into a new class of spiroheterocyclic framework: regioselective synthesis of dispiro[oxindole-cyclohexanone]-pyrrolidines and dispiro[oxindole-hexahydroindazole]pyrrolidines," *Tetrahedron* 57: 10293-10298, 2001.

Raj et al., "Synthesis, Antimicrobial and Antifungal Activity of a New Class of Spiro Pyrrolidines," *Bioorganic & Medicinal Chemistry* 11: 407-419, 2003.

Raymond et al., "Expression of Alternatively Spliced Sodium Channel α-Subunit Genes," *Journal of Biological Chemistry* 279(44): 46234-46241, Oct. 29, 2004.

Reddy et al., "Synthesis and Pharmacological Evaluation of N,N-Diarylguanidines as Potent Sodium Channel Blockers and Anticonvulsant Agents," *J. Med. Chem.* 41(17): 3298-3302, 1998.

Rehn et al., "The Three-Component Reaction between Isatin, α-Amino Acids, and Dipolarophiles," *Eur. J. Org. Chem.* 413-418, 2004.

Reimann et al., "Pain perception is altered by a nucleotide polymorphism in *SCN9A*," *PNAS* 107(11): 5148-5153, Mar. 16, 2010.

Ren and Dubner, "Enhanced Descending Modulation of Nociception in Rats With Persistent Hindpaw Inflamation," *Journal of Neurophysiology* 76(5): 3025-3037, Nov. 1996.

Rhodes et al., "Noninactivating voltage-gated sodium channels in severe myoclonic epilepsy of infancy," *PNAS* 101(30): 11147-11152, Jul. 27, 2004.

Rivalle and Bisagni, "Ethyl (4-N-Acylaminopyridin-3-yl)glyoxylate and 5-Azaisatin as New Synthons for a Route to Various New Polyheterocycles," *J. Heterocyclic Chem.* 34: 441-444, Mar.-Apr. 1997.

Rosevear and Wilshire, "Cyclization Reactions in Azole Chemistry: The Reaction of Some Azoles with *o*-Fluoro-acetophenone, *o*-Fluorobenzaldehyde and *o*-Fluorobenzophenone," *Aust. J. Chem.* 44: 1097-1114, 1991.

Ross et al., "Loss of Inhibitory Interneurons in the Dorsal Spinal Cord and Elevated Itch in *Bhlhb5* Mutant Mice," *Neuron* 65: 886-898, Mar. 25, 2010.

Rossiter, "A convenient synthesis of 3-methyleneoxindoles: cytotoxic metabolites of indole-3-acetic acids," *Tetrahedron Letters* 43: 4671-4673, 2002.

Ruan et al., "Sodium channel mutations and arrhythmias," *Nature Reviews Cardiology* 6: 337-348, May 2009.

Sadler, "Separation of Isomeric Isatins," *J. Org. Chem.* 21(2): 169-170, 1956.

Sakaki et al., "Discovery of IRL 3461: A Novel and Potent Endothelin Antagonist With Balanced $ET_A/ET_B$ Affinity," *Biooganic & Medicinal Chemistry Letters* 8: 2241-2246, 1998.

Sauviat et al., "Blockade of sodium channels by Bistramide A in voltage-clamped frog skeletal muscle fibres," *Biochimica et Biophysica Acta* 1103: 109-114, 1992.

Sawyer, "Recent Advances in Diaryl Ether Synthesis," *Tetrahedron* 56: 5045-5065, 2000.

Schnyder et al., "Synthesis of Primary Aromatic Amides by Aminocarbonylation of Aryl Halides Using Formamide as an Ammonia Synthon," *J. Org. Chem.* 66: 4311-4315, 2001.

Schulenburg and Archer, "An Unusual Base-catalyzed Cyclization," *Journal of the American Chemical Society* 83(14): 3091-3096, Jul. 20, 1961.

Sebahar et al., "Asymmetric, stereocontrolled total synthesis of (+) and (−)-spirotryprostatin B via a diastereoselective azomethine glide [1,3]-dipolar cycloaddition reaction," *Tetrahedron* 58: 6311-6322, 2002.

Shoop et al., "Anthelmintic Activity of Paraherquamide in Sheep," *J. Parasitol.* 76(3): 349-351, Jun. 1990.

Simas et al., "Regioselective Lithiation of Resorcinol Derivatives: Synthesis of Mono *O*-MOM- and *O*-Benzylresorcinols Prenylated at C-2 or C-4 Positions," *Synthesis* 6: 1017-1021, 1999.

Singh et al., "Novel cAMP PDE III Inhibitors: Imidazo[4,5-*b*]pyridine-2(3*H*)-ones and Thiazolo[4,5-*b*]pyridine-2(3*H*)-ones and Their Analogs," *J. Med. Chem.* 37: 248-254, 1994.

Smith et al., "Sodium channel protein expression enhances the invasiveness of rat and human prostate cancer cells," *FEBS Letters* 423: 19-24, 1998.

Sridhar and Raghunathan, "Rapid Access for the Synthesis of 1-N-Methyl-spiro[2.3' ]oxindole-spiro[3.7"] (3"-Aryl)-5"-methyl-3",3a",4",5",6",7"-hexahydro-2H-pyrazolo[4,3-c]pyridine-4-arylpyrrolidines Through Sequential 1,3-Dipolar Cycloaddition and Annulation," *Synthetic Communications* 36: 21-29, 2006.

Steinhoff et al., "Proteinase-Activated Receptor-2 Mediates Itch: A Novel Pathway for Pruritus in Human Skin," *Journal of Neuroscience* 23(15): 6176-6180, Jul. 16, 2003.

Subramaniyan et al., "A facile entry into a new class of spiroheterocycles: synthesis of dispiro[oxindolechromanone/flavanone/tetralone]pyrroloisoquinoline ring systems," *Tetrahedron* 58: 9075-9079, 2002.

Suchý et al., "Synthesis, Absolute Configuration, and Enantiomeric Enrichment of a Cruciferous Oxindole Phytoalexin, (*S*)-(−)-Spirobrassinin, and Its Oxazoline Analog," *J. Org. Chem.* 66: 3940-3947, 2001.

Tacconi et al., "Heterodiene Syntheses—V 1,2- versus 1,4-cycloaddition reactions of enamines to n-substituted 3-oxindolideneacetopheones," *Tetrahedron* 27: 561-579, 1971.

Takahashi et al., "Palladium(0)-Catalyzed Carbonylation on the Multipin™ System," *Tetrahedron Letters* 40: 7843-7846, 1999.

Tamaoka, "Paramyotonia Congenita and Skeletal Sodium Channelopathy," *Internal Medicine* 42(9): 769-770, Sep. 2003.

Tanelian and Brose, "Neuropathic Pain Can Be Relieved by Drugs That Are Use-dependent Sodium Channel Blockers: Lidocaine, Carbamazepine, and Mexiletine," *Anesthesiology* 74(5): 949-951, May 1991.

Ting et al., "Substituted 1,3-Dihydro-2*H*-pyrrolo[2,3-*b*]pyridin-2-ones as Potential Antiinflammatory Agents," *J. Med. Chem.* 33(10): 2697-2706, 1990.

Tokunaga et al., "Oxindole Derivatives as Orally Active Potent Growth Hormone Secretagogues," *J. Med. Chem.* 44(26): 4641-4649, 2001.

Trost and Brennan, "Palladium Asymmetric Allylic Alkylation of Prochiral Nucleophiles: Horsfiline," *Org. Lett.* 8(10): 2027-2030, 2006.

Trost and Frederiksen, "Palladium-Catalyzed Asymmetric Allylation of Prochiral Nucleophiles: Synthesis of 3-Allyl-3-Aryl Oxindoles," *Angew. Chem. Int. Ed.* 44: 308-310, 2005.

Twycross et al., "Itch: scratching more than the surface," *Q. J. Med.* 96: 7-26, 2003.

Usman et al., "1-Acetyl-3-(2-chloro-2,3-dihydrobenzofuran-3-yl)-1,2-dihydro-3-hydroxy-2-oxo-3*H*-indole," *Acta Cryst.* E58: o37-o39, 2002.

Venkatesan et al., "Total Synthesis of SR 121463 A, a Highly Potent and Selective Vasopressin $V_2$ Receptor Antagonist," *Journal of Organic Chemistry* 66(11): 3653-3661, Jun. 1, 2001.

Viaud et al., "Pyrrolo[2,3-*b*]pyridin-2(2*H*)-one Derivatives as Potential Non-opioid Analgesic Agents," *Pharmaceutical Sciences* 3: 283-287, 1997.

Viaud et al., "Acylation of Oxazolo[4,5-*b*]pyridin-2(3*H*)-ones, 2-Phenyloxazolo[4,5-*b*]pyridines and Pyrrolo[2,3-*b*]pyridin-2(2*H*)ones," *Tetrahedron* 53(14): 5159-5168, 1997.

Villamil et al., "Efficacy of lidocaine in the treatment of pruritus in patients with chronic cholestatic liver diseases," *The American Journal of Medicine* 118: 1160-1163, 2005.

Vippagunta et al., "Crystalline solids," *Advanced Drug Delivery Reviews* 48: 3-26, 2001.

Walker et al., "Limitations in Ring Rearrangement of Fused γ-Lactams Imposed by a Quaternary Carbon Atom. Cyclization of Acid Lactams to Spiro Keto Lactams," *J. Org. Chem.* 30(9): 2973-2983, Sep. 1965.

Wang and Ganesan, "A Biomimetic Total Synthesis of (−)-Spirotryprostatin B and Related Studies," *J. Org. Chem.* 65(15): 4685-4693, 2000.

Watanabe et al., "$Na_x2$/NaG Channel is involved in Control of Salt-Intake Behavior in the CNS," *Journal of Neuroscience* 20(20): 7743-7751, Oct. 15, 2000.

Weidmann et al., "2-[(2-Pyridylmethyl)sulfinyl]-1*H*-thieno[3,4-*d*]imidazoles. A Novel Class of Gastric $H^+/K^+$-ATPase Inhibitors," *J. Med. Chem.* 35: 438-450, 1992.

Wolff (ed.), *Burger's Medicinal Chemistry and Drug Discovery, Fifth Edition*, vol. 1: Principles and Practice, John Wiley & Sons, Inc., New York, New York, 1994, pp. 975-977.

Wood et al., "Voltage-Gated Sodium Channels and Pain Pathways," *J. Neurobiol.* 61: 55-71, 2004.

Wrona et al., "Hydroxyl Radical-Mediated Oxidation of Serotonin: Potential Insights into the Neurotoxicity of Methamphetamine," *J. Neurochem.* 64(3): 1390-1400, 1995.

Wu et al., "The Effect of Hypercholesterolemia on the Sodium Inward Currents in Cardiac Myocyte," *J. Mol. Cell. Cardiol.* 27: 1263-1269, 1995.

Yang and Williams, "Palladium-Catalyzed Cyanation of Aryl Bromides Promoted by Low-Level Organotin Compounds," *Organic Letters* 6(17): 2837-2840, 2004.

Yang et al., "Nucleophilic-Type Radical Cyclizations of Indoles: Conversion of 2-Cyano 3-Substituted Indoles to Spiro-Annelated Indolines and Tetrahydrocarbazolones," *J. Org. Chem.* 58: 3100-3105, 1993.

Zhang et al., "Crystal structure of *syn*-1-acetyl-9'aH-8'-methoxyspiro[indole-3,2'-oxeto[3',2':4,5]furo[3,2-*g*][1]benzopyran]2,6'-dione," *Journal of Chemical Crystallography* 33(3): 165-168, Mar. 2003.

Zhang et al., "Photoinduced [2+2] cycloadditions (the Paterno-Büchi reaction) of 1-acetylisatin with enol ethers—regioselectivity, diastereo-selectivity and acid catalysed transformations of the spirooxetane products," *J. Chem. Soc., Perkin Trans. 1*: 345-353, 2002.

Zinser et al., "Anthelmintic paraherquamides are cholinergic antagonists in gastrointestinal nematodes and mammals," *J. vet. Pharmacol. Therap.* 25: 241-250, 2002.

Invitation to Pay Additional Fees, mailed Aug. 23, 2006, for PCTAN PCT/US2006/014845, 11 pages.

International Search Report and Written Opinion, mailed Oct. 31, 2006, for PCTAN PCT/US2006/014865, 26 pages.

International Preliminary Report on Patentability, mailed Nov. 1, 2007, for PCTAN PCT/US2006/014865, 13 pages.

Chafeev et al., entitled Oxindole Compounds and Their Uses as Therapeutic Agents, Preliminary Amendment dated Jul. 14, 2006, for U.S. Appl. No. 11/408,269, 6 pages.

Chafeev et al., entitled Oxindole Compounds and Their Uses as Therapeutic Agents, Restriction Requirement mailed Sep. 9, 2008, for U.S. Appl. No. 11/408,269, 10 pages.
Chafeev et al., entitled Oxindole Compounds and Their Uses as Therapeutic Agents, Response to Restriction Requirement dated Oct. 9, 2008, for U.S. Appl. No. 11/408,269, 3 pages.
Chafeev et al., entitled Oxindole Compounds and Their Uses as Therapeutic Agents, Office Action mailed Dec. 15, 2008, for U.S. Appl. No. 11/408,269, 29 pages.
International Search Report and Written Opinion, mailed Oct. 6, 2006, for PCTAN PCT/US2006/014352, 11 pages.
International Preliminary Report on Patentability, mailed Oct. 16, 2007, for PCTAN PCT/US2006/014352, 6 pages.
Chafeev et al., entitled Spiro-Oxindole Compounds and Their Uses as Therapeutic Agents, Preliminary Amendment dated Jul. 5, 2006, for U.S. Appl. No. 11/402,310, 6 pages.
Chafeev et al., entitled Spiro-Oxindole Compounds and Their Uses as Therapeutic Agents, Restriction Requirement mailed Feb. 10, 2009, for U.S. Appl. No. 11/402,310, 7 pages.
Chafeev et al., entitled Spiro-Oxindole Compounds and Their Uses as Therapeutic Agents, Response to Restriction Requirement dated Feb. 25, 2009, for U.S. Appl. No. 11/402,310, 109 pages.
Chafeev et al., entitled Spiro-Oxindole Compounds and Their Uses as Therapeutic Agents, Office Action mailed May 15, 2009, for U.S. Appl. No. 11/402,310, 43 pages.
Chafeev et al., entitled Spiro-Oxindole Compounds and Their Uses as Therapeutic Agents, Amendment dated Aug. 17, 2009, for U.S. Appl. No. 11/402,310, 150 pages.
Chafeev et al., entitled Spiro-Oxindole Compounds and Their Uses as Therapeutic Agents, Notice of Allowance mailed Sep. 30, 2009, for U.S. Appl. No. 11/402,310, 9 pages.
Chafeev et al., entitled Spiro-Oxindole Compounds and Their Uses as Therapeutic Agents, Statement of the Substance of the Interview, mailed Oct. 30, 2009 for U.S. Appl. No. 11/402,310, 2 pages.
Chafeev et al., entitled Spiro-Oxindole Compounds and Their Uses as Therapeutic Agents, Communication dated Nov. 17, 2009, for U.S. Appl. No. 11/402,310, 4 pages.
Sun et al., entitled Spiro-Oxindole Compounds and Their Uses as Therapeutic Agents, Office Action dated Jul. 12, 2010, for U.S. Appl. No. 12/650,218, 26 pages.
Invitation to Pay Additional Fees, mailed Jan. 2, 2007, for PCTAN PCT/US2006/014887, 9 pages.
International Search Report and Written Opinion, mailed Mar. 15, 2007, for PCTAN PCT/US2006/014887, 22 pages.
International Preliminary Report on Patentability, mailed Nov. 1, 2007, for PCTAN PCT/US2006/014887, 12 pages.
Chafeev et al., entitled Heterocyclic Compounds and Their Uses as Therapeutic Agents, Preliminary Amendment dated Jul. 14, 2006, for U.S. Appl. No. 11/407,859, 6 pages.
Chafeev et al., entitled Heterocyclic Compounds and Their Uses as Therapeutic Agents, Restriction Requirement mailed Mar. 31, 2008, for U.S. Appl. No. 11/407,859, 9 pages.
Chafeev et al., entitled Heterocyclic Compounds and Their Uses as Therapeutic Agents, Response to Restriction Requirement dated Apr. 30, 2008, for U.S. Appl. No. 11/407,859, 39 pages.
Chafeev et al., entitled Heterocyclic Compounds and Their Uses as Therapeutic Agents, Office Action mailed Jun. 20, 2008, for U.S. Appl. No. 11/407,859, 46 pages.
Chafeev et al., entitled Heterocyclic Compounds and Their Uses as Therapeutic Agents, Amendment dated Oct. 17, 2008, for U.S. Appl. No. 11/407,859, 41 pages.
Chafeev et al., entitled Heterocyclic Compounds and Their Uses as Therapeutic Agents, Office Action mailed Jan. 15, 2009, for U.S. Appl. No. 11/407,859, 8 pages.
International Search Report and Written Opinion, mailed Aug. 11, 20/06, for PCTAN PCT/US2006/013318, 15 pages.
International Preliminary Report on Patentability, mailed Oct. 16, 2007, for PCTAN PCT/US2006/013318, 9 pages.
Chafeev et al., entitled Spiroheterocyclic Compounds and Their Uses as Therapeutic Agents, Preliminary Amendment dated Jul. 7, 2006, for U.S. Appl. No. 11/402,200, 6 pages.

Chafeev et al., entitled Spiroheterocyclic Compounds and Their Uses as Therapeutic Agents, Restriction Requirement mailed Feb. 10, 2009, for U.S. Appl. No. 11/402,200, 6 pages.
Chafeev et al., entitled Spiroheterocyclic Compounds and Their Uses as Therapeutic Agents, Response to Restriction Requirement dated Feb. 27, 2009, for U.S. Appl. No. 11/402,200, 31 pages.
Chafeev et al., entitled Spiroheterocyclic Compounds and Their Uses as Therapeutic Agents, Office Action mailed Apr. 24, 2009, for U.S. Appl. No. 11/402,200, 30 pages.
Chafeev et al., entitled Spiroheterocyclic Compounds and Their Uses as Therapeutic Agents, Amendment dated Aug. 24, 2009, for U.S. Appl. No. 11/402,200, 36 pages.
Chafeev et al., entitled Spiroheterocyclic Compounds and Their Uses as Therapeutic Agents, Office Action mailed Nov. 17, 2009, for U.S. Appl. No. 11/402,200, 7 pages.
Chafeev et al., entitled Spiroheterocyclic Compounds and Their Uses as Therapeutic Agents, Amendment dated Mar. 17, 2010, for U.S. Appl. No. 11/402,200, 17 pages.
Chafeev et al., entitled Spiroheterocyclic Compounds and Their Uses as Therapeutic Agents, Notice of Allowance dated May 13, 2010, for U.S. Appl. No. 11/402,200, 16 pages.
International Search Report and Written Opinion, mailed Mar. 3, 2008, for PCTAN PCT/US2007/081240, 16 pages.
International Preliminary Report on Patentability mailed Apr. 23, 20/09, for PCTAN PCT/US2007/081240, 9 pages.
International Search Report and Written Opinion, mailed Oct. 13, 2008, for PCTAN PCT/US2007/081323, 21 pages.
International Preliminary Report on Patentability, mailed Apr. 15, 2009, for PCTAN PCT/US2007/081323, 12 pages.
International Search Report and Written Opinion, mailed Mar. 3, 2008, for PCTAN PCT/US2007/081244, 21 pages.
International Preliminary Report on Patentability, mailed Apr. 23, 2009, for PCTAN PCT/US2007/081244, 12 pages.
Invitation to Pay Additional Fees, mailed Jul. 16, 2008, for PCTAN PCT/US2007/081319, 10 pages.
International Search Report and Written Opinion, mailed Dec. 29, 2008, for PCTAN PCT/US2007/081319, 18 pages.
International Preliminary Report on Patentability, mailed Apr. 15, 2009, for PCTAN PCT/US2007/081319, 8 pages.
International Search Report and Written Opinion, mailed May 19, 2008, for PCTAN PCT/US2007/081247, 18 pages.
International Preliminary Report on Patentability, mailed Apr. 15, 2009, for PCTAN PCT/US2007/081247, 10 pages.
Chafeev et al., entitled Use of Spiro-Oxindole Compounds as Therapeutic Agents, Preliminary Amendment dated Mar. 4, 2010, for U.S. Appl. No. 12/445,264, 18 pages.
International Search Report and Written Opinion, mailed May 13, 2008, for PCTAN PCT/US2007/081318, 12 pages.
International Preliminary Report on Patentability, mailed Apr. 15, 2009, for PCTAN PCT/US2007/081318, 5 pages.
International Search Report and Written Opinion, mailed Mar. 6, 2008, for PCTAN PCT/US2007/081297, 18 pages.
International Preliminary Report on Patentability, mailed Apr. 15, 2009, for PCTAN PCT/US2007/081297, 10 pages.
Invitation to Pay Additional Fees, mailed Jan. 27, 2009, for PCTAN PCT/US2007/081320, 7 pages.
Written Opinion of the International Searching Authority, mailed Jan. 5, 2009, for PCTAN PCT/US2007/081320, 11 pages.
International Preliminary Report on Patentability, mailed May 5, 2009, for PCTAN PCT/US2007/081320, 12 pages.
Invitation to Pay Additional Fees, mailed Feb. 9, 2010, for PCTAN PCT/US2009/060537, 8 pages.
Chafeev et al., entitled Spiro-Oxindole Compounds and Their Use as Therapeutic Agents, Preliminary Amendment dated Jan. 12, 2010, for U.S. Appl. No. 12/578,148, 57 pages.
International Search Report and Written Opinion, mailed Jan. 22, 2010, for PCTAN PCT/US2009/060455, 14 pages.
International Search Report and Written Opinion, mailed Apr. 8, 2010, for PCTAN PCT/US2009/069663, 13 pages.
Invitation to Pay Additional Fees, mailed Aug. 18, 2010, for PCTAN PCT/US2010/034223, 7 pages.

Arcangeli et al., "Targeting Ion Channels in Cancer: A Novel Frontier in Antineoplastic Therapy," *Current Medicinal Chemistry* 16: 66-93, 2009.

Byrn et al., "Chapter 11, Hydrates and Solvates," in *Solid-State Chemistry of Drugs*, Second Edition, 1999, pp. 233-247.

Catterall, "Molecular mechanisms of gating and drug block of sodium channels," *2002 Sodium channels and neuronal hyperexcitability*, Wiley, Chichester (Novartis Foundation Symposium 241), p. 206-225.

Diss et al., "Expression Profiles of Voltage-Gated Na$^+$ Channel α-Subunit Genes in Rat and Human Prostate Cancer Cell Lines," *The Prostate* 48:165-178, 2001.

Diss et al., "Identification and characterization of the promoter region of the Nav1.7 voltage-gated sodium channel gene (*SCN9A*)," *Mol. Cell. Neurosci.* 37: 537-547, 2008.

Hille, "Local Anesthetics: Hydrophilic and Hydrophobic Pathways for the Drug-Receptor Reaction," *The Journal of General Physiology* 69: 497-515, 1977.

Hille, "The pH-Dependent Rate of Action of Local Anesthetics on the Node of Ranvier," *The Journal of General Physiology* 69: 475-496, 1977.

Ikoma et al., "Neuronal Sensitization for Histamine-Induced Itch in Lesional Skin of Patients With Atopic Dermatitis," *Arch Dermatol.* 139: 1455-1458, Nov. 2003.

Laniado et al., "Short Communication: Expression and Functional Analysis of Voltage-Activated Na$^+$ Channels in Human Prostate Cancer Cell Lines and their Contribution to Invasion in Vitro," *American Journal of Pathology* 150(4): 1213-1221, Apr. 1997.

Li et al., "A case of primary erythermalgia with prurigo," *Clinical and Experimental Dermatology* 34: e313-e314, 2009.

Namer et al., "Separate Peripheral Pathways for Pruritus in Man," *J. Neurophysiol.* 100: 2062-2069, 2008.

Oaklander et al., "Intractable postherpetic itch and cutaneous deafferentation after facial shingles," *Pain* 96: 9-12, 2002.

Pearn, "Neurology of ciguatera," *J.Neurol. Neurosurg. Psychiatry* 70: 4-8, 2001.

Schmelz et al., "Specific C-Receptors for Itch in Human Skin," *The Journal of Neuroscience* 17(20): 8003-8008, Oct. 15, 1997.

Wang and Yosipovitch, "New insights into the pathophysiology and treatment of chronic itch in patients with End-stage renal disease, Chronic liver disease and Lymphoma," *Int. J. Dermatol.* 49(1): 1-11, Jan. 2010.

Xiao and Bennett, "C-fiber spontaneous discharge evoked by chronic inflammation is suppressed by a long-term infusion of lidocaine yielding nanogram per milliliter plasma levels," *Pain* 137: 218-228, 2008.

Zhao et al., "Voltage-gated sodium channel expression in rat and human epidermal keratinocytes: Evidence for a role in pain," *Pain* 139: 90-105, 2008.

Official Action from Intellectual Property India, mailed Mar. 28, 2011, for India Patent Application No. 4596/CHENP/2007, 4 pages.

Official Action from Intellectual Property Australia, dated Jan. 12, 2011, for Patent Application No. 2006235593, 5 pages.

Official Action from State Intellectual Property Office of China, dated Dec. 25, 2009, for Patent Application No. 200680011733.9, 4 pages.

Official Action from State Intellectual Property Office of China, dated Oct. 9, 2010, for Patent Application No. 200680011733.9, 4 pages.

Official Action from State Intellectual Property Office of China, dated Oct. 10, 2011, for Patent Application No. 201110027693.X, 5 pages.

Official Action from European Patent Office, dated Apr. 9, 2010, for Patent Application No. 06 750 402.7, 4 pages.

Response to Official Action from European Patent Office, dated Aug. 19, 2010, for Patent Application No. 06 750 402.7, 105 pages.

Official Action from European Patent Office, dated Sep. 14, 2010, for Patent Application No. 06 750 402.7, 3 pages.

Response to Official Action from European Patent Office, dated Jul. 6, 2011, for Patent Application No. 06 750 402.7, 175 pages.

Official Action from Israel Patent Office, dated Jan. 17, 2011, for Patent Application No. 186616, 3 pages.

Response to Official Action from Israel Patent Office, mailed Jul. 14, 2011, for Patent Application No. 186616, 5 pages.

Official Action from Intellectual Property India, mailed Apr. 29, 2011, for India Patent Application No. 4597/CHENP/2007, 2 pages.

Translation of Official Action from Patent Office of Japan, dated Nov. 22, 2011, for Patent Application No. 2008-506802, 11 pages.

Official Action from Intellectual Property Office of New Zealand, dated Sep. 1, 2009, for Patent Application No. 561210, 2 pages.

Response to Official Action from Intellectual Property Office of New Zealand, dated Nov. 22, 2010, for Patent Application No. 561210, 2 pages.

Official Action from Intellectual Property Office of New Zealand, dated Nov. 30, 2010, for Patent Application No. 561210, 1 page.

Response to Official Action from Intellectual Property Office of New Zealand, dated Feb. 21, 2011, for Patent Application No. 561210, 2 pages.

Official Action from Intellectual Property Office of New Zealand, dated Feb. 25, 2011, for Patent Application No. 591268, 2 pages.

Official Action from Intellectual Property Office of Republic of the Philippines, dated Sep. 22, 2010, for Patent Application No. 1-2007-502050, 2 pages.

Response to Official Action from Intellectual Property Office of the Philippines, dated Jan. 20, 2011, for Patent Application No. 1-2007-502050, 85 pages.

Translation of Official Action from Intellectual Property Office of Russia, dated Mar. 16, 2010, for Patent Application No. 2007141632/04(045572), 7 pages.

Translation of Official Action from Intellectual Property Office of Russia, dated Sep. 22, 2010, for Patent Application No. 2007141632/04(045572), 7 pages.

Chafeev et al., entitled Spiro-Oxindole Compounds and Their Uses as Therapeutic Agents, Office Action mailed Jun. 14, 2011, for U.S. Appl. No. 12/650,196, 17 pages.

Chafeev et al., entitled Spiro-Oxindole Compounds and Their Uses as Therapeutic Agents, Amendment dated Sep. 2, 2011, for U.S. Appl. No. 12/650,196, 15 pages.

Chafeev et al., entitled Spiro-Oxindole Compounds and Their Uses as Therapeutic Agents, Notice of Allowance dated Sep. 20, 2011, for U.S. Appl. No. 12/650,196, 11 pages.

Sun et al., entitled Spiro-Oxindole Compounds and Their Uses as Therapeutic Agents, Preliminary Amendment dated Jun. 24, 2011, for U.S. Appl. No. 13/078,678, 32 pages.

Sun et al., entitled Spiro-Oxindole Compounds and Their Uses as Therapeutic Agents, Restriction Requirement dated Nov. 28, 2011, for U.S. Appl. No. 13/078,678, 7 pages.

Official Action from European Patent Office, dated Aug. 5, 2008, for Patent Application No. 06 758 436.7, 5 pages.

Official Action from European Patent Office, dated Nov. 27, 2008, for Patent Application No. 06 740 804.7, 3 pages.

Response to Official Action from European Patent Office, dated Feb. 11, 2009, for Patent Application No. 06 740 804.7, 3 pages.

Official Action from Israel Patent Office, dated Jan. 16, 2011, for Patent Application No. 186615, 3 pages.

Response to Official Action from Israel Patent Office, dated Jul. 13, 2011, for Patent Application No. 186615, 3 pages.

Official Action from Intellectual Property of India, dated May 18, 2009, for Patent Application No. 4598/CHENP/2007, 2 pages.

Response to Official Action from Intellectual Property of India, dated Mar. 15, 2010, for Patent Application No. 4598/CHENP/2007, 27 pages.

Translation of Official Action from Patent Office of Japan, dated Nov. 4, 2011, for Patent Application No. 2008-506574, 10 pages.

Official Action from Intellectual Property Corporation of Malaysia, dated May 31, 2011, for Patent Application No. PI 20061651, 3 pages.

Response to Official Action from Intellectual Property Corporation of Malaysia, filed Aug. 11, 2011, for Patent Application No. PI 20061651, 30 pages.

Official Action from Intellectual Property Office of New Zealand, dated Aug. 27, 2009, for Patent Application No. 561204, 2 pages.

Response to Official Action from Intellectual Property Office of New Zealand, dated Nov. 22, 2010, for Patent Application No. 561204, 2 pages.

Official Action from Intellectual Property Office of New Zealand, dated Dec. 6, 2010, for Patent Application No. 561204, 1 page.
Response to Official Action from Intellectual Property Office of New Zealand, dated Feb. 16, 2011, for Patent Application No. 561204, 2 pages.
Translation of Official Action from Intellectual Property Office of Russia, dated Feb. 27, 2010, for Patent Application No. 2007141633/04(045573), 4 pages.
Chafeev et al., Spiroheterocyclic Compounds and Their Uses as Therapeutic Agents, Office Action mailed Aug. 25, 2011, for U.S. Appl. No. 12/855,514, 43 pages.
Official Action from State Intellectual Property Office of China, dated May 5, 2011, for Patent Application No. 200780038272.9, 9 pages.
Official Action from State Intellectual Property Office of China, dated Oct. 28, 2010, for Patent Application No. 200780038111.X, 5 pages.
Official Action from State Intellectual Property Office of China, dated Jul. 14, 2011, for Patent Application No. 200780038111.X, 5 pages.
Official Action from European Patent Office, dated Jul. 7, 2009, for Patent Application No. 07 868 434.7, 3 pages.
Official Action from European Patent Office, dated Jul. 23, 2010, for Patent Application No. 07 868 434.7, 6 pages.
Response to Official Action from European Patent Office, dated May 23, 2011, for Patent Application No. 07 868 434.7, 3 pages.
Translation of Official Action from Intellectual Property Office of Russia, dated Aug. 31,2011, for Patent Application No. 2009117642, 4 pages.
International Search Report and Written Opinion, mailed Dec. 1, 2011, for PCTAN PCT/US2010/052703, 13 pages.
International Search Report and Written Opinion, mailed Feb. 9, 2010, for PCTAN PCT/US2009/063290, 13 pages.
International Preliminary Report on Patentability, mailed May 10, 2011, for PCTAN PCT/US2009/063290, 7 pages.
International Preliminary Report on Patentability, mailed Jan. 4, 2012, for PCTAN PCT/US2010/040187, 7 pages.
Official Action from Intellectual Property Office of New Zealand, mailed Sep. 9, 2011, for New Zealand Patent Application No. 592275, 2 pages.
Chafeev et al., entitled Spiro-Oxindole Compounds and Their Use as Therapeutic Agents, Restriction Requirement mailed Aug. 15, 2011, for U.S. Appl. No. 12/578,148, 10 pages.
Chafeev et al., entitled Spiro-Oxindole Compounds and Their Use as Therapeutic Agents, Response to Restriction Requirement dated Sep. 14, 2011, for U.S. Appl. No. 12/578,148, 57 pages.
Chafeev et al., entitled Spiro-Oxindole Compounds and Their Use as Therapeutic Agents, Office Action mailed Oct. 21, 2011, for U.S. Appl. No. 12/578,148, 51 pages.
Response to Official Action from European Patent Office, dated Jan. 10, 2012, for Patent Application No. 09 740 589.8, 4 pages.
Chafeev et al., entitled Spiro-Oxindole Compounds and Their Use as Therapeutic Agents, Amendment dated Jul. 1, 2011, for U.S. Appl. No. 12/577,799, 21 pages.
Chafeev et al., entitled Spiro-Oxindole Compounds and Their Use as Therapeutic Agents, Notice of Allowance mailed Oct. 7, 2011, for U.S. Appl. No. 12/577,799, 14 pages.
International Preliminary Report on Patentability, mailed Jun. 29, 2011, for PCTAN PCT/US2009/069663, 6 pages.
International Search Report and Written Opinion, mailed Jul. 11, 2011, for PCTAN PCT/US2010/034223, 18 pages.
International Preliminary Report on Patentability, mailed Nov. 15, 2011, for PCTAN PCT/US2010/034223, 11 pages.
International Search Report and Written Opinion, mailed Jun. 9, 2011, for PCTAN PCT/US2011/026359, 14 pages.
Dierks et al., "A Method for the Simultaneous Evaluation of the Activities of Seven Major Human Drug-Metabolizing Cytochrome P450S Using an In Vitro Cocktail of Probe Substrates and Fast Gradient Liquid Chromatography Tandem Mass Spectrometry," *Drug Metabolism and Disposition* 29(1): 23-29, 2001.
Kis-Toth et al., "Voltage-Gated Channel Nav1.7 Maintains the Membrane Potential and Regulates the Activation and Chemokine-Induced Migration of a Monocyte-Derived Dendritic Cell Subset," *The Journal of Immunology* 187: 1273-1280, 2011.
Lange et al., "Regioselective Aminomethylations of Bicyclic Phenols," *Heterocycles* 53(1): 197-204, 2000.
Le Bourdonnec et al., "Medicinal Chemistry Strategies to Reduce CYP2D6 Inhibitory Activity of Lead Candidates," *Current Medicinal Chemistry* 16: 3093-3121, 2009.
Lorenz et al., "Binary and ternary phase diagrams of two enantiomers in solvent systems," *Thermochimica Acta* 382: 129-142, 2002.
Shin et al., "Potent inhibition of CYP2D6 by haloperidol metabolites: stereoselective inhibition by reduced haloperidol," *J. Clin. Pharmacol.* 51: 45-52, 2001.
Weaver et al., "Cytochrome P450 Inhibition Using Recombinant Proteins and Mass Spectrometry/Multiple Reaction Monitoring Technology in a Cassette Incubation," *Drug Metabolism and Disposition* 31(7): 955-966, 2003.
Official Action from State Intellectual Property Office of China, dated May 9, 2012, for Patent Application No. 201110027693.X, 6 pages.
Official Action from European Patent Office re extended European search report, dated Feb. 2, 2012, for Patent Application No. 11009687.2, 7 pages.
Response to Official Action from Intellectual Property India, mailed Apr. 18, 2012, for India Patent Application No. 4597/CHENP/2007, 86 pages.
Chafeev et al., entitled Tricyclic Spiro-Oxindole Derivatives and Their Uses as Therapeutic Agents, Restriction Requirement mailed Jan. 26, 2012, for U.S. Appl. No. 12/445,271, 7 pages.
Official Action from State Intellectual Property Office of China, dated Feb. 20, 2012, for Patent Application No. 200780038272.9, 5 pages.
Cadieux et al., entitled Spiro (Furo [3, 2-C] Pyridine-3-3' -Indol)-2' (1'H)-One Derivatives and Related Compounds for the Treatment of Sodium-Channel Mediated Diseases, Such as Pain, Restriction Requirement mailed Apr. 19, 2012, for U.S. Appl. No. 12/445,270, 6 pages.
International Preliminary Report on Patentability, mailed Apr. 17, 2012, for PCTAN PCT/US2010/052704, 6 pages.
Cadieux et al., entitled Synthetic Methods for Spiro-Oxindole Compounds, Restriction Requirement mailed May 7, 2012, for U.S. Appl. No. 12/904,880, 7 pages.
Official Action from Intellectual Property Australia, dated Mar. 22, 2012, for Patent Application No. 2007319580, 2 pages.
Translation of Official Action from Intellectual Property Office of Russia, dated Feb. 2, 2012, for Patent Application No. 2009117642, 8 pages.
International Preliminary Report on Patentability, mailed Apr. 17, 2012, for PCTAN PCT/US2010/052703, 9 pages.
Winters et al., entitled Pharmaceutical Compositions for Oral Administration, Restriction Requirement mailed May 7, 2012 for U.S. Appl. No. 12/905,048, 9 pages.
Chafeev et al., entitled Spiro-Oxindole Compounds and Their Use as Therapeutic Agents, Response to Office Action dated Feb. 21, 2012, for U.S. Appl. No. 12/578,148, 46 pages.
Chafeev et al., entitled Spiro-Oxindole Compounds and Their Use as Therapeutic Agents, Notice of Allowance dated Apr. 27, 2012 for U.S. Appl. No. 12/578,148, 12 pages.
Response to Official Action from European Patent Office, dated Feb. 1, 2012, for Patent Application No. 09 741 118.5, 12 pages.

* cited by examiner

ENANTIOMERS OF SPIRO-OXINDOLE COMPOUNDS AND THEIR USES AS THERAPEUTIC AGENTS

CROSS-REFERENCE TO RELATED APPLICATION

This application claims the benefit under 37 U.S.C. §119(e) of U.S. Provisional Patent Application No. 61/221,424, filed Jun. 29, 2009. This application is incorporated herein by reference in its entirety.

FIELD OF THE INVENTION

This invention is directed to a specific enantiomer of a spiro-oxindole compound, specifically to the enantiomer's use in human or veterinary therapeutics for treating diseases or conditions in a mammal, preferably a human, which are ameliorated or alleviated by the modulation, preferably inhibition, of voltage-gated sodium channels.

BACKGROUND OF THE INVENTION

PCT Published Patent Application No. WO 2006/110917, the disclosure of which is incorporated in full by reference herein, discloses certain spiro-oxindole compounds, in particular, 1'-{[5-(trifluoromethyl)furan-2-yl]methyl}spiro[furo[2,3-f][1,3]benzodioxole-7,3'-indol]-2'(1'H)-one, i.e., the compound of the following formula (I):

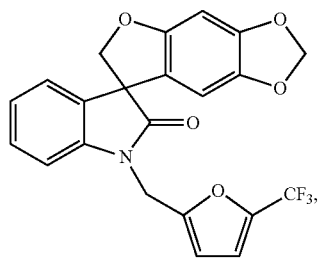

(I)

These compounds are disclosed therein as being useful in treating diseases or conditions, such as pain, in mammals, preferably humans, which are ameliorated or alleviated by the modulation, preferably inhibition, of voltage-gated sodium channels.

SUMMARY OF THE INVENTION

The present invention is directed to the discovery that the (S)-enantiomer and the (R)-enantiomer of the following compound of formula (I):

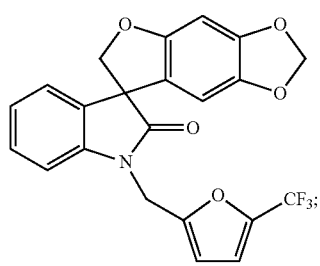

(I)

demonstrate a difference in potency for the inhibition of voltage-gated sodium channel activity.

Accordingly, in one aspect, the invention provides the (S)-enantiomer of 1'-{[5-(trifluoromethyl)furan-2-yl]methyl}spiro[furo[2,3-f][1,3]benzodioxole-7,3'-indol]-2'(1'H)-one, i.e., the (S)-enantiomer having the following formula (I-S):

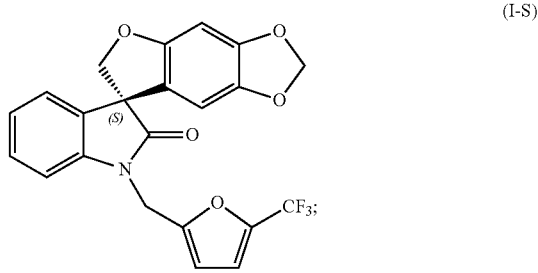

(I-S)

or a pharmaceutically acceptable solvate or prodrug thereof. Preferably, the (S)-enantiomer is substantially free of the (R)-enantiomer.

In another aspect, the invention provides a pharmaceutical composition comprising the (S)-enantiomer, or a pharmaceutically acceptable solvate or prodrug thereof, as set forth above, preferably substantially free of the (R)-enantiomer, and one or more pharmaceutically acceptable excipients.

In one embodiment, the present invention relates to a pharmaceutical composition comprising the (S)-enantiomer, or a pharmaceutically acceptable solvate or prodrug thereof, as set forth above, preferably substantially free of the (R)-enantiomer, in a pharmaceutically acceptable carrier and in an amount effective to treat diseases or conditions related to pain when administered to an animal, preferably a mammal, most preferably a human.

In another aspect, the invention provides pharmaceutical therapy in combination with the (S)-enantiomer, or a pharmaceutically acceptable solvate or prodrug thereof, as set forth above, preferably substantially free of the (R)-enantiomer, and one or more other existing therapies or as any combination thereof to increase the efficacy of an existing or future drug therapy or to decrease the adverse events associated with the existing or future drug therapy. In one embodiment, the present invention relates to a pharmaceutical composition combining the (S)-enantiomer, or a pharmaceutically acceptable solvate or prodrug thereof, as set forth above, preferably substantially free of the (R)-enantiomer, with established or future therapies for the indications listed in the invention.

In another aspect, the invention provides a method of treating a disease or a condition in a mammal, preferably a human, wherein the disease or condition is selected from the group consisting of pain, depression, cardiovascular diseases, respiratory diseases, psychiatric diseases, neurological diseases and seizures, and combinations thereof, wherein the method comprises administering to the mammal in need thereof a therapeutically effective amount of the (S)-enantiomer, as set forth above, or a pharmaceutically acceptable solvate or prodrug thereof.

In another aspect, the invention provides a method for the treatment of pain in a mammal, preferably a human, wherein the method comprises administering to the mammal in need thereof a therapeutically effective amount of the (S)-enantiomer, or a pharmaceutically acceptable solvate or prodrug thereof, as set forth above, preferably substantially free of the (R)-enantiomer.

In another aspect, the present invention provides a method for treating or lessening the severity of a disease, condition, or disorder where activation or hyperactivity of one or more voltage-gated sodium channel proteins, including, but not limited to, $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ voltage-gated sodium channel, is implicated in the disease, condition or disorder, wherein the method comprises administering to the mammal in need thereof a therapeutically effective amount of the (S)-enantiomer, or a pharmaceutically acceptable solvate or prodrug thereof, as set forth above, preferably substantially free of the (R)-enantiomer.

In another aspect, the invention provides a method of treating diseases or conditions in mammals, preferably humans, which are associated with the activity of voltage-gated sodium channels. Accordingly, the invention provides a method of treating diseases or conditions in mammals, preferably humans, which are ameliorated or alleviated by the modulation, preferably inhibition, of voltage-gated sodium channels. Examples of such diseases or conditions include, but are not limited to, pain of any nature and origin, pain associated with HIV, HIV treatment induced neuropathy, trigeminal neuralgia, post-herpetic neuralgia, diabetic neuropathy, complex regional pain syndrome (CRPS), Paroxysmal Extreme Pain Disorder (PEPD), eudynia, heat sensitivity, sarcoidosis, irritable bowel syndrome, Crohns disease, pain associated with multiple sclerosis (MS), motor impairment associated with MS, amyotrophic lateral sclerosis (ALS), pruritis, hypercholesterolemia, benign prostatic hyperplasia, peripheral neuropathy, arthritis, rheumatoid arthritis, osteoarthritis, paroxysmal dystonia, periodic paralysis, myasthenia syndromes, myotonia, malignant hyperthermia, cystic fibrosis, pseudoaldosteronism, rhabdomyolysis, bipolar depression, anxiety, schizophrenia, illness due to exposure to insecticides or other agents that promote neuronal or muscle hyperexcitability, familial erythermalgia, secondary erythermalgia, familial rectal pain, familial facial pain, migraine, headache, neuralgiform headache, familial hemiplegic migraine, conditions associated with cephalic pain, sinus headache, tension headache, phantom limb pain, peripheral nerve injury, cancer, epilepsy, partial and general tonic seizures, restless leg syndrome, arrhythmias, fibromyalgia, neuroprotection under ischaemic conditions caused by stroke, glaucoma or neural trauma, tachy-arrhythmias, atrial fibrillation and ventricular fibrillation, wherein the method comprises administering to the mammal in need thereof a therapeutically effective amount of the (S)-enantiomer, or a pharmaceutically acceptable solvate or prodrug thereof, as set forth above, preferably substantially free of the (R)-enantiomer.

In another aspect, the invention provides a method of treating a disease or condition in a mammal, preferably a human, by the inhibition of ion flux through a voltage-gated sodium channel in the mammal, wherein the method comprises administering to the mammal in need thereof a therapeutically effective amount of the (S)-enantiomer, or a pharmaceutically acceptable solvate or prodrug thereof, as set forth above, preferably substantially free of the (R)-enantiomer.

In another aspect, the invention provides a method of decreasing ion flux through a voltage-gated sodium channel in a cell in a mammal, wherein the method comprises contacting the cell with the (S)-enantiomer, or a pharmaceutically acceptable solvate or prodrug thereof, as set forth above, preferably substantially free of the (R)-enantiomer.

The invention further provides the use of the (S)-enantiomer, or a pharmaceutically acceptable solvate or prodrug thereof, as set forth above, preferably substantially free of the (R)-enantiomer, in the preparation of a medicament composition in the treatment of a disease or condition that is associated with the activity of a voltage-gated sodium channel. Accordingly, the invention provides the use of the (S)-enantiomer, or a pharmaceutically acceptable solvate or prodrug thereof, as set forth above, preferably substantially free of the (R)-enantiomer, in the preparation of a medicament composition in the treatment of a disease or condition which is ameliorated or alleviated by the modulation, preferably inhibition, of a voltage-gated sodium channel.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Definitions

Figure 1:
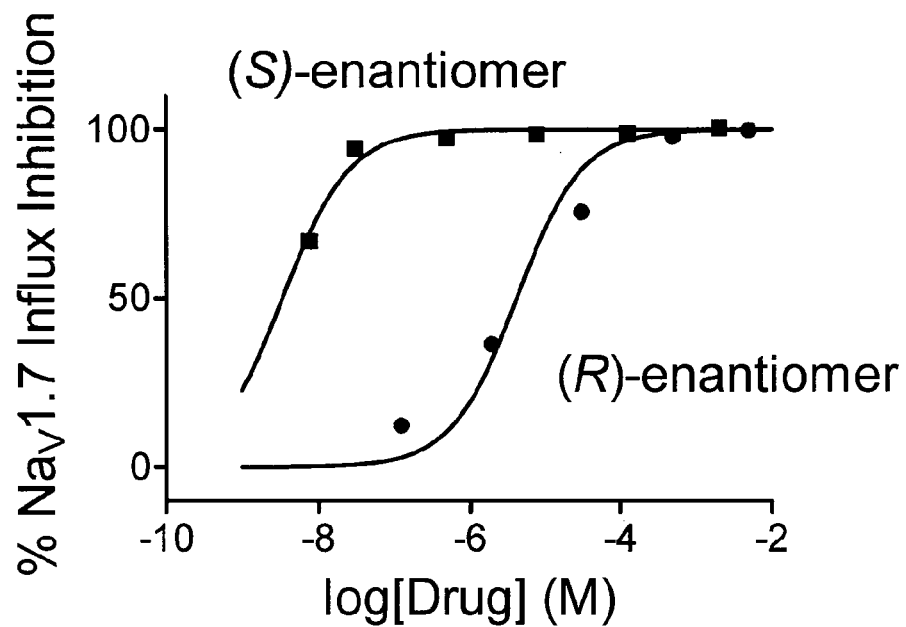
FIG. 1 shows concentration-response relationship for the (S)- and (R)-enantiomers in the Guanidine Influx Assay from Biological Example 1 herein.

As used in the specification and appended claims, unless specified to the contrary, the following terms have the meaning indicated:

"Analgesia" refers to an absence of pain in response to a stimulus that would normally be painful.

"Allodynia" refers to a condition in which a normally innocuous sensation, such as pressure or light touch, is perceived as being painful.

"Enantiomers" refers to asymmetric molecules that can exist in two different isomeric forms which have different configurations in space. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions). Because they do not have a plane of symmetry, enantiomers are not identical with their mirror images; molecules which exist in two enantiomeric forms are chiral, which means that they can be regarded as occurring in "left" and "right" handed forms. The most common cause of chirality in organic molecules is the presence of a tetrahedral carbon bonded to four different substituents or groups. Such a carbon is referred to as a chiral center, or stereogenic center. A method for indicating the three-dimensional arrangement of atoms (or the configuration) at a stereogenic center is to refer to the arrangement of the priority of the groups when the lowest priority group is oriented away from a hypothetical observer: If the arrangement of the remaining three groups from the higher to the lower priority is clockwise, the stereogenic center has an "R" (or "D") configuration; if the arrangement is counterclockwise, the stereogenic center has an "S" (or "L") configuration.

Enantiomers have the same empirical chemical formula, and are generally chemically identical in their reactions, their physical properties, and their spectroscopic properties. However, enantiomers show different chemical reactivity toward other asymmetric compounds, and respond differently toward asymmetric physical disturbances. The most common asymmetric disturbance is polarized light.

An enantiomer can rotate plane-polarized light; thus, an enantiomer is optically active. Two different enantiomers of the same compound will rotate plane-polarized light in the opposite direction; thus, the light can be rotated to the left or counterclockwise for a hypothetical observer (this is levarotatory or "l", or minus or "−") or it can be rotated to the right or clockwise (this is dextrorotatory or "d" or plus or "+"). The sign of optical rotation (+) or (−), is not related to the R,S designation. A mixture of equal amounts of two chiral enantiomers is called a racemic mixture, or racemate, and is denoted either by the symbol (+/−) or by the prefix "d,l" to indicate a mixture of dextrorotatory and levorotatory forms. The compound of formula (I), as described herein, is a racemate. Racemates or racemic mixtures show zero optical rotation because equal amounts of the (+) and (−) forms are present. In general, the presence of a single enantiomer rotates polarized light in only one direction; thus, a single enantiomer is referred to as optically pure.

The designations "R" and "S" are used to denote the absolute configuration of the molecule about its chiral center(s). The designations may appear as a prefix or as a suffix; they may or may not be separated from the enantiomer name by a hyphen; they may or may not be hyphenated; and they may or may not be surrounded by parentheses.

The designations or prefixes "(+) and (−)" are employed herein to designate the sign of rotation of plane-polarized light by the compound, with (−) meaning that the compound is levorotatory (rotates to the left). A compound prefixed with (+) is dextrorotatory (rotates to the right).

"Resolution" or "resolving" when used in reference to a racemic compound or mixture refers to the separation of a racemate into its two enantiomeric forms (i.e., (+) and (−); (R) and (S) forms).

"Enantiomeric excess" or "ee" refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purposes of this invention, the (S)-enantiomer of the invention is considered to be "substantially free" of the (R)-enantiomer when the (S)-enantiomer is present in enantiomeric excess of greater than 80%, preferably greater than 90%, more preferably greater than 95% and most preferably greater than 99%.

The chemical naming protocol and structure diagrams used herein are a modified form of the I.U.P.A.C. nomenclature system, using the ACD/Name Version 9.07 software program. For example, the compound of formula (I), as set forth above in the Summary of the Invention, is named herein as 1'-{[5-(trifluoromethyl)furan-2-yl]methyl}spiro[furo[2,3-f][1,3]benzodioxole-7,3'-indol]-2'(1'H)-one. The corresponding (S)-enantiomer, i.e., the (S)-enantiomer of formula (I-S), as set forth above in the Summary of the Invention, is named herein as (S)-1'-{[5-(trifluoromethyl)furan-2-yl]methyl}spiro[furo[2,3-f][1,3]benzodioxole-7,3'-indol]-2'(1'H)-one. The corresponding (R)-enantiomer, the (R)-enantiomer of the following formula (I-R):

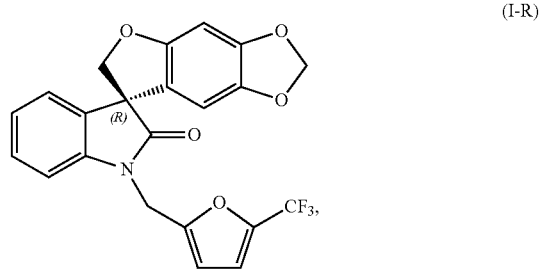

(I-R)

or a pharmaceutically acceptable solvate or prodrug thereof, is named herein as (R)-1'-{[5-(trifluoromethyl)furan-2-yl]methyl}spiro[furo[2,3-f][1,3]benzodioxole-7,3'-indol]-2'(1'H)-one.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass the (S)-enantiomer and the (R)-enantiomer disclosed herein being isotopically-labelled by having one or more atoms replaced by an atom having a different atomic mass or mass number. Examples of isotopes that can be incorporated into the disclosed compounds include isotopes of hydrogen, carbon, nitrogen, oxygen, such as $^{2}H$, $^{3}H$, $^{11}C$, $^{13}C$, $^{14}C$, $^{13}N$, $^{15}N$, $^{15}O$, $^{17}O$, $^{18}O$, and $^{18}F$, respectively. These radiolabelled compounds could be useful to help determine or measure the effectiveness of the compounds, by characterizing, for example, the site or mode of action on the voltage-gated sodium channels, or binding affinity to pharmacologically important site of action on the voltage-gated sodium channels. Isotopically-labelled compounds are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. A radioligand incorporating tritium ($^3$H) is particularly useful for ligand binding studies with membranes that contain voltage-gated sodium channels because tritium has a long half-life of decay and the emission is of relatively low energy and the radioisotope is therefore relatively safe. The radioligand is typically prepared by exchange of tritium with a hydrogen in an unlabeled compound. The identification of active and inactive enantiomers of a particular racemate facilitates the development of a ligand binding assay because the unlabeled inactive enantiomer can be added to the assay to reduce, eliminate or otherwise control non-specific binding of the tritiated active enantiomer.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topgraphy (PET) studies for examining substrate receptor occupancy. Isotopically-labeled enantiomers of the invention can generally be prepared by conventional techniques known to those skilled in the art or by processes analogous to those described herein using an appropriate isotopically-labeled reagent in place of the non-labeled reagent previously employed.

The invention disclosed herein is also meant to encompass the in vivo metabolic products of the disclosed enantiomers. Such products may result from, for example, the oxidation, reduction, hydrolysis, amidation, esterification, and the like of the administered compound, primarily due to enzymatic processes. Accordingly, the invention includes metabolic products produced by a process comprising contacting an enantiomer of this invention with a mammal for a period of time sufficient to yield the metabolic product. Such metabolic products may be identified by administering a radiolabelled enantiomer of the invention in a detectable dose to an animal, such as rat, mouse, guinea pig, monkey, or to human, allowing sufficient time for metabolism to occur, and isolating the metabolic product from the urine, blood or other biological samples.

"Selectivity" and "selective" as used herein is a relative measure of the tendency for a compound of the invention to preferentially associate with one thing as opposed to another (or group of others), as between or among voltage-gated sodium channels. For example, the selectivity may be determined by comparative measurements of the kinetics and equilibrium binding affinity and/or functional measures of ion transport through the voltage-gated sodium channels. The tendency of a compound to associate with a voltage-gated sodium channel can be measured by many different techniques, and many types of association are known to those skilled in the art, as disclosed elsewhere herein. Selectivity means that in a particular type of association, measured in a specific way, a compound demonstrates a tendency or preference to associate with one voltage-gated sodium channel as opposed to one or more of the other voltage-gated sodium channels. This association may be different for different types of assays or different ways of measurement.

"Stable enantiomer" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g. cats, dogs, swine, cattle, sheep, goats, horses, and rabbits), and non-domestic animals such as wildlife and the like.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by, for non-limiting example, the United States Food and Drug Administration, Health Canada or the European Medicines Agency, as being acceptable for use in humans or domestic animals.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefore.

The pharmaceutical compositions of the invention comprise one or more pharmaceutically acceptable excipients, which include, but are not limited to, any solvent, adjuvant, bioavailability enhancer, carrier, glidant, sweetening agent, diluent, preservative, dye/colorant, flavor enhancer, surfactant, wetting agent, dispersing agent, suspending agent, stabilizer, isotonic agent, buffer and/or emulsifier approved by, for non-limiting example, the United States Food and Drug Administration, Health Canada or the European Medicines Agency, as being acceptable for use in humans or domestic animals. Exemplary pharmaceutically acceptable excipients include, but are not limited to, the following:

benzyl alcohol
benzyl benzoate
caprylocaproyl macrogolglycerides (e.g. Labrasol®)
dimethylamine ("DMA")
ethanol
2-(2-ethoxyethoxy)ethanol (e.g., Transcutol®)
glucose (solution)
glyceryl caprylate/caprate and PEG-8 (polyethylene glycol) caprylate/caprate complex (e.g., Labrasol®)
isopropyl alcohol
Lauroyl Macrogol-32 Glycerides (e.g. Gelucire® 44/14)
macrogol-15 hydroxystearate (e.g., Solutol® HS15)
medium chain triglycerides (e.g., Miglyol® 810, Miglyol® 840 or Miglyol® 812)
peanut oil
polysorbate 80 (e.g., Tween® 80)
polyethylene glycol (PEG)
polyethylene glycol 400 (PEG400, e.g., Lutrol® E 400)
polyethylene glycol 6000
polyoxyl 35 castor oil (e.g., Cremophor® EL)
polyoxyl 40 hydrogenated castor oil (e.g., Cremophor® RH 40)
propylene glycol (PG)
propylene glycol monocaprylate (Capryol® 90)
soybean oil
sulfobutylether-β-cyclodextrin (e.g., Capitsol®)
TPGS (α-tocopherol polyethylene glycol succinate)
water
Additional pharmaceutically acceptable excipients are disclosed herein.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

"Therapeutically effective amount" refers to that amount of a compound of the invention which, when administered to a mammal, preferably a human, is sufficient to effect treatment, as defined below, of a disease or condition of interest in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain with or without addressing the underlying disease or condition.

As used herein, the terms "ameliorating", "ameliorated", "alleviating" or "alleviated" are to be given their generally acceptable definitions. For example, to "ameliorate" generally means to make better or to improve a condition relative to the condition prior to the ameliorating event. To "alleviate" generally means to make a condition more bearable relative to the condition prior to the alleviating event. As used herein, "ameliorating" or "ameliorated" can refer to a disease or condition that is made better or improved by the administration of a compound of the invention. As used herein, "alleviating" or "alleviated" can refer to a disease or condition that is made bearable by the administration of a compound of the invention. For example, "alleviating" pain would include reducing the severity or amount of pain.

As used herein, the terms "disease", "disorder" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

Utility and Testing of the Compounds of the Invention

The present invention relates to the (S)-enantiomer of 1'-{[5-(trifluoromethyl)furan-2-yl]methyl}spiro[furo[2,3-f][1,3]benzodioxole-7,3'-indol]-2'(1'H)-one, pharmaceutical compositions and methods of using the (S)-enantiomer of the invention and pharmaceutical compositions for the treatment of diseases or conditions which are ameliorated or alleviated by the modulation, preferably inhibition, of voltage-gated sodium channels, preferably diseases and conditions related to pain and pruritus; central nervous system conditions such as epilepsy, restless leg syndrome, anxiety, depression and bipolar disease; cardiovascular conditions such as arrhythmias, atrial fibrillation and ventricular fibrillation; neuromuscular conditions such as muscle paralysis, myotonia or tetanus; neuroprotection against stroke, neural trauma and multiple sclerosis; and channelopathies such as erythromelalgia and familial rectal pain syndrome, by administering to a patient in need of such treatment an effective amount of a voltage-gated sodium channel blocker modulating, especially inhibiting, agent, preferably the enantiomers of the invention.

In general, the present invention provides a method for treating a mammal, preferably a human, for, or protecting a mammal, preferably a human, from developing, a disease or condition that is associated with the activity of voltage-gated sodium channels, especially pain, wherein the method comprises administering to the mammal a therapeutically effective amount of the (S)-enantiomer, or a pharmaceutically acceptable solvate or prodrug thereof, as set forth above in the Summary of the Invention, wherein the (S)-enantiomer modulates, preferably inhibits, the activity of one or more of the voltage-gated sodium channels.

The voltage-gated sodium channel family of proteins has been extensively studied and shown to be involved in a number of vital body functions. Research in this area has identified variants of the alpha subunits that result in major changes in channel function and activities, which can ultimately lead to major pathophysiological conditions. In addition, excessive sodium influx can arise indirectly via inflammatory agents or factors that result in hyperexcitability. Implicit with function, this family of proteins are considered prime points of therapeutic intervention. Voltage-gated sodium channel proteins $Na_v1.1$ and $Na_v1.2$ are highly expressed in the brain (Raymond, C. K., et al., *J. Biol. Chem.* (2004), 279(44): 46234-41) and are vital to normal brain function. In humans, mutations in $Na_v1.1$ and $Na_v1.2$ result in epileptic states and in some cases mental decline and migraines (Rhodes, T. H., et at, *Proc. Natl. Acad. Sci.* USA (2004), 101(30):11147-52; Kamiya, K., et at, *J. Biol. Chem.* (2004), 24(11):2690-8; Pereira, S., et al., *Neurology* (2004), 63(1):191-2; Meisler, M. H. et at, *J. Physiol.* (Lond.) (in press). As such both channels have been considered as validated targets for the treatment of epilepsy (see PCT Published Patent Publication No. WO 01/38564).

$Na_v1.3$ is expressed primarily in the central nervous system in neonatal animals and at low levels throughout the body in adults (Raymond, C. K., et al., op. cit.). It has been demonstrated to have its expression upregulated in the dorsal horn sensory neurons of rats after nervous system injury (Hains, B. D., et al., *J. Neurosci.* (2003), 23(26):8881-92). Many experts in the field have considered $Na_v1.3$ as a suitable target for pain therapeutics because its expression is induced by nerve injury (Lai, J., et at, *Curr. Opin. Neurobiol.* (2003), (3):291-72003; Wood, J. N., et al., *J. Neurobiol.* (2004), 61(1):55-71; Chung, J. M., et al., *Novartis Found Symp.* (2004), 261:19-27; discussion 27-31, 47-54; Priest, B. T., *Curr. Opin. Drug Discov. Devel.* (2009) 12:682-693).

$Na_v1.4$ expression is essentially limited to muscle (Raymond, C. K., et al., op. cit.). Mutations in this gene have been shown to have profound effects on muscle function including paralysis (Tamaoka A., *Intern. Med.* (2003), (9):769-70). Thus, this channel is considered a target for the treatment of periodic paralysis, myotonia, abnormal muscle contractility, spasm or paralysis.

The cardiac voltage-gated sodium channel, $Na_v1.5$, is expressed mainly in cardiac myocytes (Raymond, C. K., et al., op. cit.), and can be found in the atria, ventricles, sinoatrial node, atrio-ventricular node and Purkinje cells. The rapid upstroke of the cardiac action potential and the rapid impulse conduction through cardiac tissue is due to the opening of $Na_v1.5$. As such, $Na_v1.5$ is involved in cardiac arrhythmias. Mutations in human $Na_v1.5$ result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H. et at, *Am. J. Pharmacogenomics* (2003), 3(3):173-9; Ruan, Y et al., *Nat. Rev. Cardiol.* (2009) 6: 337-48). Voltage-gated sodium channel blocker therapy has been used extensively in treating cardiac arrhythmias. The first antiarrhythmic drug, quinidine, discovered in 1914, is classified as a sodium channel blocker.

$Na_v1.6$ encodes an abundant, widely distributed voltage-gated sodium channel found throughout the central and peripheral nervous systems, clustered in the nodes of Ranvier of neural axons (Caldwell, J. H., et al., *Proc. Natl. Acad. Sci. USA* (2000), 97(10): 5616-20). Loss of function mutations in mice result in ataxia and convulsions (Papale, L. A. et al., *Human Mol. Genetics*. (2009) 18, 1633-1641). Although no mutations in humans have been detected, $Na_v1.6$ is thought to play a role in the manifestation of the symptoms associated with multiple sclerosis and has been considered as a target for the treatment of this disease (Craner, M. J., et al., *Proc. Natl. Acad. Sci.* USA (2004), 101(21):8168-73).

$Na_v1.7$ is expressed primarily in the peripheral nervous system in both sensory and sympathetic neurons (Raymond, C. K., et al., op. cit.). Loss of function mutations in humans cause congenital indifference to pain (CIP) without impairment of cognitive or motor function (Cox, J. J. et al., *Nature* (2006) 444 (7121), 894-8; Goldberg, Y. P. et al., *Clin. Genet.* (2007) 71 (4), 311-9). Individuals with CIP do not experience inflammatory or neuropathic pain, suggesting that selective block of $Na_v1.7$ would eliminate multiple forms of chronic and acute pain without deleterious effect on the central or peripheral nervous systems or on muscle. Moreover, a single nucleotide polymorphism (R1150W) that has very subtle effects on the time- and voltage-dependence of $Na_v1.7$ gating has large effects on pain perception (Reimann, F. et al., *Proc. Natl. Acad. Sci.* USA (2010), 107 (11), 5148-53). About 10% of the patients with a variety of pain conditions are heterozygous for the allele conferring greater sensitivity to pain. The involvement of $Na_v1.7$ in mediating pain responses is also evidenced by gain of function mutations that result in erythromelalgia or Paroxysmal extreme pain disorder (Dib-Hajj S. D. et al., *Adv. Genet.* (2009) 63: 85-110). Although $Na_v1.7$ is expressed primarily in the peripheral nervous system, a point mutation in $Na_v1.7$ causes febrile seizures, indicating a role for this channel in the CNS. Thus, voltage-gated sodium channel blockers may be useful as anticonvulsant agents.

The expression of $Na_v1.8$ is predominately in the dorsal root ganglia (DRG) (Raymond, C. K., et al., op. cit.). The upstroke of the action potential in sensory neurons from DRG is primarily carried by current through $Na_v1.8$, so that block of this current is likely to block pain responses (Blair, N T and Bean, B P, *J. Neurosci.* 22: 10277-90). Consistent with this finding, knock-down of $Na_v1.8$ in rats has been achieved by using antisense DNA or small interfering RNAs and virtually complete reversal of neuropathic pain was achieved in the spinal nerve ligation and chronic constriction injury models. A selective blocker of $Na_v1.8$ has been reported and it is effective at blocking both neuropathic and inflammatory pain (Jarvis, M. F. et al., *Proc. Natl. Acad. Sci.* USA (2007), 104 (20), 8520-5). PCT Published Patent Application No. WO03/037274A2 describes pyrazole-amides and sulfonamides for the treatment of central or peripheral nervous system conditions, particularly pain and chronic pain by blocking sodium channels associated with the onset or recurrence of the indicated conditions. PCT Published Patent Application No. WO03/037890A2 describes piperidines for the treatment of central or peripheral nervous system conditions, particularly pain and chronic pain by blocking sodium channels associated with the onset or recurrence of the indicated conditions. The compounds, compositions and methods of these inventions are of particular use for treating neuropathic or inflammatory pain by the inhibition of ion flux through a channel that includes a PN3 ($Na_v1.8$) subunit.

The peripheral nervous system voltage-gated sodium channel $Na_v1.9$, disclosed by Dib-Hajj, S. D., et al. (see Dib-Hajj, S. D., et al., *Proc. Natl. Acad. Sci.* USA (1998), 95(15):8963-8) was shown to be expressed in the dorsal root ganglia. It has been demonstrated that $Na_v1.9$ underlies neurotrophin (BDNF)-evoked depolarization and excitation. The limited pattern of expression of this channel has made it a candidate target for the treatment of pain (Lai, J, et al., op. cit.; Wood, J. N., et al., op. cit.; Chung, J. M. et al., op. cit.).

NaX is a putative sodium channel, which has not been shown to be voltage gated. In addition to expression in the lung, heart, dorsal root ganglia, and Schwann cells of the peripheral nervous system, NaX is found in neurons and ependymal cells in restricted areas of the CNS, particularly in the circumventricular organs, which are involved in body-fluid homeostasis (Watanabe, E., et al., *J. Neurosci.* (2000), 20(20):7743-51). NaX-null mice showed abnormal intakes of hypertonic saline under both water- and salt-depleted conditions. These findings suggest that the NaX plays an important role in the central sensing of body-fluid sodium level and regulation of salt intake behaviour. Its pattern of expression and function suggest it as a target for the treatment of cystic fibrosis and other related salt regulating maladies.

Studies with the voltage-gated sodium channel blocker tetrodotoxin (TTX) used to lower neuron activity in certain regions of the brain, indicate its potential use in the treatment of addiction. Drug-paired stimuli elicit drug craving and relapse in addicts and drug-seeking behavior in rats. The functional integrity of the basolateral amygdala (BLA) is necessary for reinstatement of cocaine-seeking behaviour elicited by cocaine-conditioned stimuli, but not by cocaine itself. BLA plays a similar role in reinstatement of heroin-seeking behavior. TTX-induced inactivation of the BLA on conditioned and heroin-primed reinstatement of extinguished heroin-seeking behaviour in a rat model (Fuchs, R. A. and See, R. E., *Psychopharmacology* (2002) 160(4):425-33).

A subset of C fibers mediate responses to pruritogenic agents, especially itch caused by histamine, activators of PAR-2 receptors, cholestasis, and viral infections (Steinhoff, M. et al., *J. Neurosci.* 23:6176-80; Twycross, R. et al., *Q. J. Med.* 96:7-26). Voltage-gated sodium channels are expressed in and mediate C-fiber nerve impulses.

The general value of the (S)-enantiomer of the invention in modulating, especially inhibiting, the voltage-gated sodium channel ion flux can be determined using the assays described below in the Biological Assays section. Alternatively, the general value of the (S)-enantiomer of the invention in treating conditions and diseases may be established in industry standard animal models for demonstrating the efficacy of compounds in treating pain. Animal models of human neuropathic pain conditions have been developed that result in reproducible sensory deficits (allodynia, hyperalgesia, and spontaneous pain) over a sustained period of time that can be evaluated by sensory testing. By establishing the degree of mechanical, chemical, and temperature induced allodynia and hyperalgesia present, several physiopathological conditions observed in humans can be modeled allowing the evaluation of pharmacotherapies.

In rat models of peripheral nerve injury, ectopic activity in the injured nerve correlates with the behavioural signs of pain. In these models, intravenous application of the (S)-enantiomer of the invention and local anesthetic lidocaine can suppress the ectopic activity and reverse the tactile allodynia at concentrations that do not affect general behaviour and motor function (Mao, J. and Chen, L. L, *Pain* (2000), 87:7-17). Allimetric scaling of the doses effective in these rat models, translates into doses similar to those shown to be efficacious in humans (Tanelian, D. L. and Brose, W. G., *Anesthesiology* (1991), 74(5):949-951). Furthermore, Lidoderm®, lidocaine applied in the form of a dermal patch, is currently an FDA approved treatment for post-herpetic neuralgia (Devers, A. and Glaler, B. S., *Clin. J. Pain* (2000), 16(3):205-8).

Voltage-gated sodium channel blockers have clinical uses in addition to pain. Epilepsy and cardiac arrhythmias are often targets of sodium channel blockers. Recent evidence from animal models suggest that voltage-gated sodium channel blockers may also be useful for neuroprotection under ischaemic conditions caused by stroke or neural trauma and in patients with multiple sclerosis (MS) (Clare, J. J. et al., op. cit. and Anger, T. et al., op. cit.).

The (S)-enantiomer of the invention modulates, preferably inhibits, ion flux through a voltage-gated sodium channel in a mammal, especially in a human. Any such modulation, whether it be partial or complete inhibition or prevention of ion flux, is sometimes referred to herein as "blocking" and corresponding compounds as "blockers" or "inhibitors". In general, the compound of the invention modulates the activity of a voltage-gated sodium channel downwards, inhibits the voltage-dependent activity of the voltage-gated sodium channel, and/or reduces or prevents sodium ion flux across a cell membrane by preventing voltage-gated sodium channel activity such as ion flux.

The (S)-enantiomer of the invention is a sodium channel blocker and is therefore useful for treating diseases and conditions in mammals, preferably in humans, and other organisms, including all those human diseases and conditions which are the result of aberrant voltage-gated sodium channel biological activity or which may be ameliorated or alleviated by modulation, preferably inhibition, of voltage-gated sodium channel biological activity.

As defined herein, a disease or condition which is ameliorated or alleviated by the modulation, preferably inhibition of a voltage-gated sodium channel refers to a disease or condition which is ameliorated or alleviated upon the modulation, preferably inhibition, of the voltage-gated sodium channel and includes, but is not limited to, pain and pruritis; central nervous conditions such as epilepsy, anxiety, depression (Morinville et al., *J. Comp. Neurol.*, 504:680-689 (2007)) and bipolar disease (Ettinger and Argoff, *Neurotherapeutics*, 4:75-83 (2007)); cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromelalgia and familial rectal pain syndrome.

Additional diseases and conditions include pain associated with HIV, HIV treatment induced neuropathy, trigeminal neuralgia, glossopharyngeal neuralgia, neuropathy secondary to metastatic infiltration, adiposis dolorosa, thalamic lesions, hypertension, autoimmune disease, asthma, drug addiction (e.g. opiate, benzodiazepine, amphetamine, cocaine, alcohol, butane inhalation), Alzheimer's (Kim DY, Carey et al., *Nat. Cell Biol.* 9(7):755-764 (2007)), dementia, age-related memory impairment, Korsakoff syndrome, restenosis, urinary dysfunction, incontinence, parkinson's disease (Do and Bean, *Neuron* 39:109-120 (2003); Puopolo et al., *J. Neurosci.* 27:645-656 (2007)), cerebrovascular ischemia, neurosis, gastrointestinal disease, sickle cell anemia, sickle cell disease, transplant rejection, heart failure, myocardial infarction, reperfusion injury, intermittent claudication, angina, convulsion, respiratory disorders, cerebral or myocardial ischemias, long-QT syndrome, Catecholeminergic polymorphic ventricular tachycardia, ophthalmic diseases, spasticity, spastic paraplegia, myopathies, myasthenia gravis, paramyotonia congentia, hyperkalemic periodic paralysis, hypokalemic periodic paralysis, alopecia, anxiety disorders, psychotic disorders, mania, paranoia, seasonal affective disorder, panic disorder, obsessive compulsive disorder (OCD), phobias, autism, Aspergers Syndrome, Retts syndrome, disintegrative disorder, attention deficit disorder, aggressivity, impulse control disorders, thrombosis, pre clampsia, congestive cardiac failure, cardiac arrest, Freidrich's ataxia, Spinocerebellear ataxia, tremor, muscle weakness, myelopathy, radiculopathy, systemic lupus erythamatosis, granulomatous disease, olivo-ponto-cerebellar atrophy, spinocerebellar ataxia, episodic ataxia, myokymia, progressive pallidal atrophy, progressive supranuclear palsy and spasticity, traumatic brain injury, cerebral oedema, hydrocephalus injury, spinal cord injury, anorexia nervosa, bulimia, Prader-Willi syndrome, obesity, optic neuritis, cataract, retinal haemorrhage, ischaemic retinopathy, retinitis pigmentosa, acute and chronic glaucoma, macular degeneration, retinal artery occlusion, Chorea, Huntington's disease, Huntington's chorea, cerebral edema, proctitis, post-herpetic neuralgia, eudynia, heat sensitivity, sarcoidosis, irritable bowel syndrome, Tourette syndrome, Lesch-Nyhan Syndrome, Brugado syndrome, Liddle syndrome, Crohns disease, multiple sclerosis and the pain associated with multiple sclerosis (MS), amyotrophic lateral sclerosis (ALS), disseminated sclerosis, diabetic neuropathy, peripheral neuropathy, charcot marie tooth syndrome, arthritis, rheumatoid arthritis, osteoarthritis, chondrocalcinosis, paroxysmal dystonia, myasthenia syndromes, myotonia, myotonic dystrophy, muscular dystrophy, malignant hyperthermia, cystic fibrosis, pseudoaldosteronism, rhabdomyolysis, mental handicap, bipolar depression, anxiety, schizophrenia, sodium channel toxin related illnesses, familial erythromelalgia, primary erythromelalgia, rectal pain, cancer, epilepsy, partial and general tonic seizures, febrile seizures, absence seizures (petit mal), myoclonic seizures, atonic seizures, clonic seizures, Lennox Gastaut, West Syndome (infantile spasms), sick sinus syndrome (Haufe V, Chamberland C, Dumaine R, *J. Mol. Cell. Cardiol.* 42(3):469-477 (2007)), multiresistant seizures, seizure prophylaxis (anti-epileptogenic), familial Mediterranean fever syndrome, gout, restless leg syndrome, arrhythmias, fibromyalgia, neuroprotection under ischaemic conditions caused by stroke or neural trauma, tachyarrhythmias, atrial fibrillation and ventricular fibrillation and as a general or local anaesthetic.

As used herein, the term "pain" refers to all categories of pain, regardless of its nature or origin, and is understood to include, but not limited to, neuropathic pain, inflammatory pain, nociceptive pain, idiopathic pain, neuralgic pain, orofacial pain, burn pain, chronic bone pain, low back pain, neck pain, abdominal pain, burning mouth syndrome, somatic pain, visceral pain (including abdominal), myofacial pain, dental pain, cancer pain, chemotherapy pain, myofascial pain syndrome, complex regional pain syndrome (CRPS), temporomandibular joint pain, trauma pain, Paroxysmal Extreme Pain Disorder, surgical pain, post-surgical pain, childbirth pain, labor pain, reflex sympathetic dystrophy, brachial plexus avulsion, neurogenic bladder, acute pain, musculoskeletal pain, post-operative pain, chronic pain, persistent pain, peripherally mediated pain, centrally mediated pain, chronic headache, tension headache, cluster headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, post-herpetic pain, non-cardiac chest pain, irritable bowel syndrome and pain associated with bowel disorders and dyspepsia, and combinations thereof.

The present invention also relates to compounds, pharmaceutical compositions and methods of using the compounds and pharmaceutical compositions for the treatment or prevention of diseases or conditions such as benign prostatic hyperplasia (BPH), hypercholesterolemia, cancer and pruritus (itch).

Benign prostatic hyperplasia (BPH), also known as benign prostatic hypertrophy, is one of the most common diseases affecting aging men. BPH is a progressive condition which is characterized by a nodular enlargement of prostatic tissue resulting in obstruction of the urethra. Consequences of BPH can include hypertrophy of bladder smooth muscle, a decompensated bladder, acute urinary retention and an increased incidence of urinary tract infection.

BPH has a high public health impact and is one of the most common reasons for surgical intervention among elderly men. Attempts have been made to clarify the etiology and pathogenesis and, to that end, experimental models have been developed. Spontaneous animal models are limited to the chimpanzee and the dog. BPH in man and the dog share many common features. In both species, the development of BPH occurs spontaneously with advanced age and can be prevented by early/prepubertal castration. A medical alternative to surgery is very desirable for treating BHP and the consequences.

The prostatic epithelial hyperplasia in both man and the dog is androgen sensitive, undergoing involution with androgen deprivation and resuming epithelial hyperplasia when androgen is replaced. Cells originating from the prostate gland have been shown to express high levels of voltage gated sodium channels. Immunostaining studies clearly demonstrated evidence for voltage gated sodium channels in prostatic tissues (*Prostate Cancer Prostatic Dis.* 2005; 8(3):266-73). Inhibiton of voltage-gated sodium channel function with tetrodotoxin, a selective blocker, inhibits migration of cells derived from prostate and breast cancers (Brackenbury, W. J. and Djamgoz, M. B. A., *J. Physiol.* (Lond) (2006) 573: 343-56; Chioni, A-M. et al., Int. *J. Biochem. Cell Biol.* (2009) 41:1216-1227).

Hypercholesterolemia, i.e., elevated blood cholesterol, is an established risk factor in the development of, e.g., atherosclerosis, coronary artery disease, hyperlipidemia, stroke, hyperinsulinemias, hypertension, obesity, diabetes, cardiovascular diseases (CVD), myocardial ischemia, and heart attack. Thus, lowering Ithe levels of total serum cholesterol in individuals with high levels of cholesterol has been known to reduce the risk of these diseases. The lowering of low density lipoprotein cholesterol in particular is an essential step in the prevention of CVD. Although there are a variety of hypercholesterolemia therapies, there is a continuing need and a continuing search in this field of art for alternative therapies.

The invention provides compounds which are useful as antihypercholesterolemia agents and their related conditions. The present compounds may act in a variety of ways. While not wishing to be bound to any particular mechanism of action, the compounds may be direct or indirect inhibitors of the enzyme acyl CoA: cholesterol acyl transferase (ACAT) that results in inhibition of the esterification and transport of cholesterol across the intestinal wall. Another possibility may be that the compounds of the invention may be direct or indirect inhibitors of cholesterol biosynthesis in the liver. It is possible that some compounds of the invention may act as both direct or indirect inhibitors of ACAT and cholesterol biosynthesis.

Pruritis, commonly known as itch, is a common dermatological condition. There exist two broad categories of itch based upon the etiology: inflammatory skin itch and neuropathic itch (Binder et al., *Nature Clinical Practice,* 4:329-337, 2008). In the former case, inflammatory mediators activate cutaneous pruriceptors, a subset of dermal afferent nerve fibers, primarily unmyelinated C fibers. Treatments for this type of itch consist of either blocking receptors for the inflammatory agents (such as anti-histamines) or blocking the ensuing electrical activity. Voltage-gated sodium channels have a central role in the transmission of electrical activity in neurons and modulation of voltage-gated sodium channels is a well established means of modulating this signalling. Although the causes of neuropathic pruritis are complex and less well understood, there is well established evidence of central sensitization and hypersensitivity of input from sensory neuron C fibers in the dermis. As for inflammatory itch, sodium channels likely are essential for propagating electrical signals from the skin to the CNS. Transmission of the itch impulses results in the unpleasant sensation that elicits the desire or reflex to scratch.

Both inflammatory and neuropathic itch can be blocked by known voltage-gated sodium channel blockers, most commonly lidocaine (Villamil et al., *American Journal of Medicine* 118:1160-1163, 2005; Inan et al., *Euorpean Journal of Pharmacology* 616: 141-146, 2009; Fishman et al., *American Journal of Medicine* 102: 584-585, 1997; Ross et al., *Neuron* 65: 886-898, 2010). The doses of lidocaine needed to relieve itch are comparable to those effective in treating pain. Both sensory circuits share common mediators and related neuronal pathways (Ikoma et al., *Nature Reviews Neuroscience,* 7:535-547, 2006). However, other treatments for pain are ineffective against itch and can exacerbate pruritis rather than relieve it. For example, opioids, in particular, are effective at relieving pain, yet can generate severe pruritis. Thus, voltage-gated sodium channel block is a particularly promising therapy for both pain and itch.

Compounds of the present invention have been shown to have analgesic effects in a number of animal models at oral doses ranging from 1 mg/Kg to 100 mg/Kg. The compounds of the invention can also be useful for treating pruritis.

The types of itch or skin irritation, include, but are not limited to:

a) psoriatic pruritis, itch due to hemodyalisis, aguagenic pruritis, and itching caused by skin disorders (e.g., contact dermatitis), systemic disorders, neuropathy, psychogenic factors or a mixture thereof;

b) itch caused by allergic reactions, insect bites, hypersensitivity (e.g., dry skin, acne, eczema, psoriasis), inflammatory conditions or injury;

c) itch associated with vulvar vestibulitis;

d) skin irritation or inflammatory effect from administration of another therapeutic such as, for example, antibiotics, antivirals and antihistamines; and e) itch due to activation of PAR-2 G-protein coupled receptors.

The (S)-enantiomer of the invention modulates, preferably inhibits, the ion flux through a voltage-dependent sodium channel. Preferably, the (S)-enantiomer of the invention is a state- or frequency-dependent modifier of the voltage-gated sodium channels, having a low affinity for the rested/closed state and a high affinity for the inactivated state. While not wishing to be bound to any particular mechanism of action, the (S)-enantiomer of the invention is likely to interact with overlapping sites located in the inner cavity of the sodium conducting pore of the channel similar to that described for other state-dependent sodium channel blockers (Cestèle, S., et al, op. cit.). The (S)-enantiomer of the invention may also be likely to interact with sites outside of the inner cavity and have allosteric effects on sodium ion conduction through the channel pore.

In a preferred embodiment of the invention, the (S)-enantiomer of the invention modulates, preferably inhibits, the activity of $Na_v1.7$. In another preferred embodiment of the invention, the (S)-enantiomer of the invention selectively modulates, preferably inhibits, the activity of $Na_v1.7$ as compared to the modulation or inhibition of other voltage-gated sodium channels (i.e. $Na_v1.1$ to $Na_v1.6$ and $Na_v1.8$ to $Na_v1.9$). Because most other sodium channels are implicated in other important physiological processes, such as contraction and rhythmicity of the heart ($Na_v1.5$), contraction of skeletal muscle ($Na_v1.4$), and conduction of electrical activity in CNS and motor neurons ($Na_v1.1$, $Na_v1.2$ and $Na_v1.6$), it is desirable that the (S)-enantiomer of the invention avoid significant modulation of these other sodium channels.

Any of these consequences may ultimately be responsible for the overall therapeutic benefit provided by the (S)-enantiomer of the invention.

Typically, a successful therapeutic agent of the invention will meet some or all of the following criteria. Oral availability should be at or above 20%. Animal model efficacy is less than about 0.1 µg to about 100 mg/Kg body weight and the target human dose is between 0.1 µg to about 100 mg/Kg body weight, although doses outside of this range may be acceptable ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 µM, preferably below 1 µM and most preferably below 50 nM. The $IC_{50}$ ("Inhibitory Concentration—50%") is a measure of the amount of the (S)-enantiomer of the invention required to achieve 50% inhibition of ion flux through a sodium channel, over a specific time period, in an assay of the invention.

Another aspect of the invention relates to inhibiting $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ activity in a biological sample or a mammal, preferably a human, which method comprises administering to the mammal, or contacting the biological sample with, the (S)-enantiomer of the invention or a composition comprising the (S)-enantiomer of the invention. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

In addition to the foregoing uses of the (S)-enantiomer of the invention, the compound may also be useful in the modulation, preferably inhibition, of voltage-gated sodium channel activity in a biological sample for a variety of purposes that are known to one of skill in the art. Examples of such purposes include, but are not limited to, the study of voltage-gated sodium ion channels in biological and pathological phenomena; and the comparative evaluation of new or other voltage-gated sodium ion channel modulators.

The (S)-enantiomer of the invention may also be used to treat non-human mammals (i.e., veterinary methods of treatment) for diseases or conditions which are ameliorated or alleviated by the modulation, preferably inhibition, of voltage-gated sodium channels, particularly for the treatment of inflammation and pain. Such treatment is understood to be of particular interest for companion mammals, such as dogs and cats.

Pharmaceutical Compositions of the Invention and Administration

The present invention also relates to pharmaceutical composition containing the (S)-enantiomer of the invention. In one embodiment, the present invention relates to a composition comprising the (S)-enantiomer of the invention in a pharmaceutically acceptable carrier and in an amount effective to modulate, preferably inhibit, ion flux through a voltage-gated sodium channel to treat diseases, such as pain, when administered to an animal, preferably a mammal, most preferably a human patient.

Administration of the (S)-enantiomer of the invention, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient, preferably a mammal, more preferably a human, take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J., current edition).

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred compositions contain, in addition to the (S)-enantiomer of the invention, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of the (S)-enantiomer of the invention such that a suitable dosage will be obtained. Typically, this amount is at least 0.01% of the (S)-enantiomer of the invention in the composition. When intended for oral administration, this amount may be varied to be between 0.1 and about 70% of the weight of the composition. Preferred oral pharmaceutical compositions contain between about 4% and about 50% of the (S)-enantiomer of the invention. Preferred pharmaceutical compositions and preparations according to the present invention are prepared so that a parenteral dosage unit contains between 0.01 to 10% by weight of the (S)-enantiomer of the invention prior to dilution.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the (S)-enantiomer of the invention from about 0.1 to about 10% w/v (weight per unit volume).

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of the (S)-enantiomer of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

A typical formulation for intramuscular or intrathecal administration will consist of a suspension or solution of active in an oil or solution of active ingredient in an oil, for example arachis oil or seasame oil. A typical formulation for intravenous or intrathecal administration will consist of sterile isotonic aqueous solution containing, for example active ingredient and dextrose or sodium chloride or a mixture of dextrose and sodium chloride.

The compositions of the invention can be formulated so as to provide quick, sustained or delayed release of the active ingredient, i.e, the (S)-enantiomer of the invention, after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the (S)-enantiomer of the invention in a substantially zero order pattern on a daily basis similar to devises used to apply testosterone as described in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transport ionized drugs into and through body tissues). Those skilled in the art would combine the best suited excipients with the (S)-enantiomer of the invention for safe and effective intra-ocular administration.

The most suitable route of administration will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the (S)-enantiomer of the invention to a subject in need thereof.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the (S)-enantiomer of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of the (S)-enantiomer of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining the (S)-enantiomer of the invention with sterile, distilled water so as to form a solution. A surfactant may be added to facilitate the formation of a homogeneous solution or suspension. Surfactants are compounds that non-covalently interact with the (S)-enantiomer of the invention so as to facilitate dissolution or homogeneous suspension of the compound in the aqueous delivery system.

The (S)-enantiomer of the invention is to be administered in a therapeutically effective amount, which will vary depending upon a variety of factors including the activity of the specific compound employed; the metabolic stability and length of action of the (S)-enantiomer of the invention; the age, body weight, general health, sex, and diet of the patient; the mode and time of administration; the rate of excretion; the drug combination; the severity of the particular disorder or condition; and the subject undergoing therapy. Generally, a therapeutically effective daily dose of the (S)-enantiomer of the invention is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.70 mg) to about 50 mg/Kg (i.e., 3.5 g); and more preferably a therapeutically effective dose is (for a 70 Kg mammal) from about 1 mg/Kg (i.e., 70 mg) to about 25 mg/Kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts. (see, e.g., Berkowet at, eds., The Merck Manual, $16^{th}$ edition, Merck and Co., Rahway, N.J., 1992; Goodmanetna., eds., Goodman and Cilman's The Pharmacological Basis of Therapeutics, $10^{th}$ edition, Pergamon Press, Inc., Elmsford, N.Y., (2001); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, (1985); Osolci al., eds., Remington's Pharmaceutical Sciences, $18^{th}$ edition, Mack Publishing Co., Easton, Pa. (1990); Katzung, Basic and Clinical Pharmacology, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. Effective amounts of the (S)-enantiomer of the invention or composition of the invention are from about 0.1 μg to about 100 mg/Kg body weight, administered at intervals of 4-72 hours, for a period of 2 hours to 1 year, and/or any range or value therein, such as 0.0001-0.001, 0.001-0.01, 0.01-0.1, 0.1-1.0, 1,0-10, 5-10, 10-20, 20-50 and 50-100 mg/Kg, at intervals of 1-4, 4-10, 10-16, 16-24, 24-36, 24-36, 36-48, 48-72 hours, for a period of 1-14, 14-28, or 30-44 days, or 1-24 weeks, or any range or value therein.

The recipients of administration of the (S)-enantiomer of the invention and/or compositions of the invention can be any animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

Combination Therapy

The (S)-enantiomer of the invention may be usefully combined with one or more other therapeutic agent or as any combination thereof, in the treatment of diseases and conditions in mammals, preferably humans, which are ameliorated or alleviated by the modulation, preferably inhibition, of voltage-gated sodium channels. For example, the (S)-enantiomer of the invention may be administered simultaneously, sequentially or separately in combination with other therapeutic agents, including, but not limited to:

- opiates analgesics, e.g. morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;
- non-opiate analgesics, e.g. acetomeniphen, salicylates (e.g. aspirin);
- nonsteroidal antiinflammatory drugs (NSAIDs), e.g. ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;
- anticonvulsants, e.g. carbamazepine, oxcarbazepine, lamotrigine, valproate, topiramate, gabapentin and pregabalin;
- antidepressants such as tricyclic antidepressants, e.g. amitriptyline, clomipramine, despramine, imipramine and nortriptyline;
- COX-2 selective inhibitors, e.g. celecoxib, rofecoxib, parecoxib, valdecoxib, deracoxib, etoricoxib, and lumiracoxib;
- alpha-adrenergics, e.g. doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;
- barbiturate sedatives, e.g. amobarbital, aprobarbital, butabarbital, butabital, mephobarbital, metharbital, methohexital, pentobarbital, phenobartital, secobarbital, talbutal, theamylal and thiopental;
- tachykinin (NK) antagonist, particularly an NK-3, NK-2 or NK-1 antagonist, e.g. (αR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);
- coal-tar analgesics, in particular paracetamol;
- serotonin reuptake inhibitors, e.g. paroxetine, sertraline, norfluoxetine (fluoxetine desmethyl metabolite), metabolite demethylsertraline, 3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;
- noradrenaline (norepinephrine) reuptake inhibitors, e.g. maprotiline, lofepramine, mirtazepine, oxaprotiline, fezolamine, tomoxetine, mianserin, buprorion, buprorion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;
- dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;
- acetylcholinesterase inhibitors such as donepezil;
- 5-HT3 antagonists such as ondansetron;
- metabotropic glutamate receptor (mGluR) antagonists or agonists or allosteric potentiators of glutamate at mGluR's;
- local anaesthetic such as mexiletine and lidocaine;
- corticosteroid such as dexamethasone;
- antiarrhythimics, e.g. mexiletine and phenyloin;
- muscarinic antagonists, e.g., tolterodine, propiverine, tropsium t chloride, darifenacin, solifenacin, temiverine and ipratropium;
- muscarinic agonists or allosteric potentiators of acetylcholine at muscarinic receptors
- cannabinoids or allosteric potentiators of endorphins at cannabinoid receptors;
- vanilloid receptor agonists (e.g. resinferatoxin) or antagonists (e.g. capsazepine);
- sedatives, e.g. glutethimide, meprobamate, methaqualone, and dichloralphenazone;
- anxiolytics such as benzodiazepines,
- antidepressants such as mirtazapine,
- topical agents (e.g. lidocaine, capsacin and resiniferotoxin);
- muscle relaxants such as benzodiazepines, baclofen, carisoprodol, chlorzoxazone, cyclobenzaprine, methocarbamol and orphrenadine;
- anti-histamines or H1 antagonists;
- NMDA receptor antagonists;
- 5-HT receptor agonists/antagonists;
- PDEV inhibitors;
- Tramadol®;
- cholinergic (nicotinic) analgesics;
- alpha-2-delta ligands;
- prostaglandin E2 subtype antagonists;
- leukotriene B4 antagonists;
- 5-lipoxygenase inhibitors; and
- 5-HT3 antagonists.

Diseases and conditions that may be treated and/or prevented using such combinations include, but are not limited to, pain, central and peripherally mediated, acute, chronic, neuropathic diseases, as well as other diseases with associated pain and other central nervous disorders such as epilepsy, anxiety, depression and bipolar disease; or cardiovascular disorders such as arrhythmias, atrial fibrillation and ventricular fibrillation; neuromuscular disorders such as restless leg syndrome and muscle paralysis or tetanus (Hamann M, Meisler M H, Richter, A *Exp. Neurol.* 184(2):830-838 (2003)); neuroprotection against stroke, neural trauma and multiple sclerosis; and channelopathies such as erythromelalgia and familial rectal pain syndrome.

As used herein "combination" refers to any mixture or permutation of the (S)-enantiomer of the invention with one or more additional therapeutic agent. Unless the context makes clear otherwise, "combination" may include simultaneous or sequentially delivery of the (S)-enantiomer of the invention with one or more therapeutic agents. Unless the context makes clear otherwise, "combination" may include dosage forms of the (S)-enantiomer of the invention with another therapeutic agent. Unless the context makes clear otherwise, "combination" may include routes of administration of the (S)-enantiomer of the invention with another therapeutic agent. Unless the context makes clear otherwise, "combination" may include formulations of the (S)-enantiomer of the invention with another therapeutic agent. Dosage forms, routes of administration and pharmaceutical compositions include, but are not limited to, those described herein.

One combination therapy of the invention includes a topical application of the (S)-enantiomer of the invention with an oral agent. The topical application of the (S)-enantiomer of the invention has very low systemic exposure and has activity that is additive with a number of oral analgesics. Another possible combination therapy includes an oral dose of the (S)-enantiomer of the invention with an oral agent. A further combination therapy of the invention includes a topical application of the (S)-enantiomer of the invention with a topical agent.

The (S)-enantiomer of the invention may be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described above and a carrier suitable for coating the implantable device. In still another aspect, the present invention includes an implantable device coated with a composition comprising the (S)-enantiomer of the invention and a carrier suitable for coating the implantable device. Suitable coatings and the general preparation of coated implantable devices are described in U.S. Pat. Nos. 6,099,562; 5,886,026; and 5,304,121.

Kits-of-Parts

The present invention also provides kits that contain a pharmaceutical composition of the invention. The kit also includes instructions for the use of the pharmaceutical composition for modulating the activity of ion channels, for the treatment of pain, as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that such compositions which are light and/or air sensitive may require special packaging and/or formulation. For example, packaging may be used which is opaque to light, and/or sealed from contact with ambient air, and/or formulated with suitable coatings or excipients.

Preparation of the (S)-Enantiomer of the Invention

The (S)-enantiomer of the invention and the corresponding (R)-enantiomer are prepared by the resolution of the compound of formula (I), as set forth above in the Summary of the Invention, using either chiral high pressure liquid chromatography methods or by simulated moving bed chromatography methods, as described below in the following Reaction Scheme wherein "chiral HPLC" refers to chiral high pressure liquid chromatography and "SMB" refers to simulated moving bed chromatography:

REACTION SCHEME

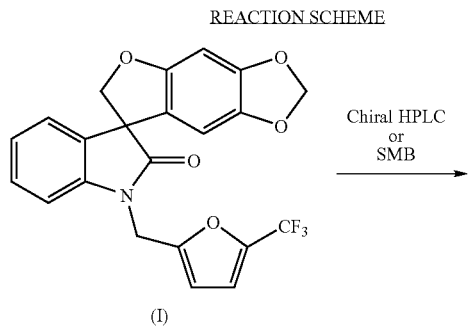

(I)

Chiral HPLC or SMB
→

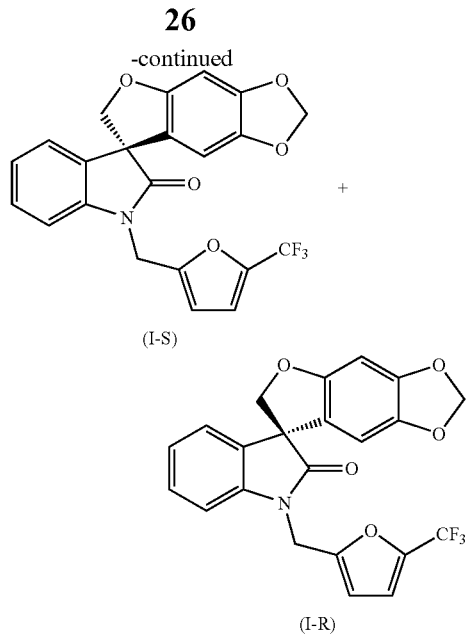

The compound of formula (I) can be prepared by the methods disclosed in PCT Published Patent Application No. WO 2006/110917, by methods disclosed herein, or by methods known to one skilled in the art.

One of ordinary skill in the art would recognize variations in the above Reaction Scheme which are appropriate for the resolution of the individual enantiomers.

Alternatively, the (S)-enantiomer of formula (I-S) and the (R)-enantiomer of formula (I-R), can be synthesized from starting materials which are known or readily prepared using process analogous to those which are known.

Preferably, the (S)-enantiomer of the invention obtained by the resolution methods disclosed herein is substantially free of the (R)-enantiomer or contains only traces of the (R)-enantiomer.

The following Synthetic Examples serve to illustrate the resolution methods disclosed by the above Reaction Schemes and are not intended to limit the scope of the invention.

SYNTHETIC EXAMPLE 1

Synthesis of 1-{[5-(trifluoromethyl)furan-2-yl]methyl}spiro[furo[2,3-f][1,3]benzodioxole-7,3'-indol]-2'(1'H)-one (Compound of formula (I))

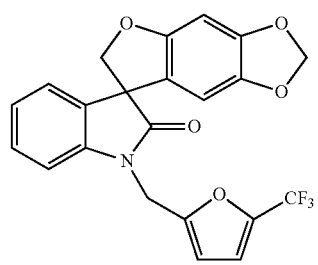 [SMILES: O=C1N(Cc2ccc(C(F)(F)F)o2)c2ccccc2C12COc1cc3c(cc12)OCO3]

To a suspension of spiro[furo[2,3-f][1,3]benzodioxole-7,3'-indol]-2'(1'H)-one (1.0 g, 3.6 mmol), which can be prepared according to the methods disclosed in PCT Published Patent Application No. WO 2006/110917, and cesium carbonate (3.52 g, 11 mmol) in acetone (50 mL) was added 2-bromomethyl-5-trifluoromethylfuran (1.13 g, 3.9 mmol) in one portion and the reaction mixture was stirred at 55-60° C. for 16 hours. Upon cooling to ambient temperature, the reaction mixture was filtered and the filtrate was evaporated under reduced pressure. The residue was subjected to column chromatography, eluting with ethyl acetate/hexane (1/9-1/1) to afford 1'-{[5-(trifluoromethyl)furan-2-yl]methyl}spiro[furo[2,3-f][1,3]benzodioxole-7,3'-indol]-2'(1 'H)-one, i.e., the compound of formula (I), (1.17 g, 76%) as a white solid: mp 139-141° C.; $^1$H NMR (300 MHz, CDCl$_3$) δ 7.32-6.97 (m, 5H), 6.72 (d, J=3.3 Hz, 1H), 6.66 (s, 1H), 6.07 (s, 1H), 5.90-5.88 (m, 2H), 5.05, 4.86 (ABq, J$_{AB}$=16.1 Hz, 2H), 4.91 (d, J=9.0 Hz, 1H), 4.66 (d, J=9.0 Hz, 1H); $^{13}$C NMR (75 MHz, CDCl$_3$) δ 176.9, 155.7, 153.5, 148.8, 142.2, 141.9, 140.8, 140.2, 139.7, 139.1, 132.1, 129.2, 124.7, 124.1, 123.7, 121.1, 120.1, 117.6, 114.5, 114.4, 110.3, 109.7, 103.0, 101.9, 93.8, 80.0, 57.8, 36.9;

MS (ES+) m/z 430.2 (M+1), 452.2 (M+23); Cal'd for C$_{22}$H$_{14}$F$_3$NO$_5$: C, 61.54%; H, 3.29%; N, 3.26%; Found: C, 61.51%; H, 3.29%; N, 3.26%.

SYNTHETIC EXAMPLE 2

Resolution of Compound of Formula (I) by Chiral HPLC

The compound of formula (I) was resolved into the (S)-enantiomer of the invention and the corresponding (R)-enantiomer by chiral HPLC under the following conditions:

Column: Chiralcel® OJ-RH; 20 mm I.D.×250 mm, 5 mic; Lot: OJRH CJ-EH001 (Daicel Chemical Industries, Ltd)

Eluent: Acetonitrile/Water (60/40, v/v, isocratic)

Flow rate: 10 mL/min

Run time: 60 min

Loading: 100 mg of compound of formula (I) in 1 mL of acetonitrile

Temperature: Ambient

Under the above chiral HPLC conditions, the (R)-enantiomer of the compound of formula (I), i.e., (R)-1'-{[5-(trifluoromethyl)furan-2-yl]methyl}spiro[furo[2,3-f][1,3]-benzodioxole-7,3'-indol]-2'(1'H)-one, was isolated as the first fraction as a white solid; ee (enantiomeric excess)>99% (analytical OJ-RH, 55% acetonitrile in water); mp 103-105° C.; $^1$H NMR (300 MHz, DMSO-d$_6$) δ 7.32-6.99 (m, 5H), 6.71 (d, J=3.4 Hz, 1H), 6.67 (s, 1H), 6.05 (s, 1H), 5.89 (d, J=6.2 Hz, 2H), 5.13, 5.02 (ABq, J$_{AB}$=16.4 Hz, 2H), 4.82, 4.72 (ABq, J$_{AB}$=9.4 Hz, 2H); $^{13}$C NMR (75 MHz, CDCl$_3$) δ 177.2, 155.9, 152.0, 149.0, 142.4, 142.0, 141.3, 132.0, 129.1, 123.9, 120.6, 119.2, 117.0, 112.6, 109.3, 108.9, 103.0, 101.6, 93.5, 80.3, 58.2, 36.9; MS (ES+) m/z 430.2 (M+1), [α]$_D$−17.46° (c 0.99, DMSO). The (S)-enantiomer of the compound of formula (I), i.e., (S)-1'-{[5-(trifluoromethyl)furan-2-yl]methyl}spiro[furo[2,3-f][1,3]benzodioxole-7,3'-indol]-2'(1'H)-one was isolated as the second fraction as a white solid; ee>99% (analytical OJ-RH, 55% acetonitrile in water); mp 100-102° C.; $^1$H NMR (300 MHz, DMSO-d$_6$) δ 7.32-6.99 (m, 5H), 6.71 (d, J=3.4 Hz, 1H), 6.67 (s, 1H), 6.05 (s, 1H), 5.89 (d, J=6.3 Hz, 2H), 5.12, 5.02 (ABq, J$_{AB}$=16.4 Hz, 2H), 4.82, 4.72 (ABq, J$_{AB}$=9.4 Hz, 2H); $^{13}$C NMR (75 MHz, CDCl$_3$) δ 177.2, 155.9, 152.0, 149.0, 142.4, 142.0, 141.3, 132.0, 129.1, 123.9, 120.6, 119.2, 117.0, 112.6, 109.3, 108.9, 103.0, 101.6, 93.5, 80.3, 58.2, 36.9; MS (ES+) m/z 430.2 (M+1), [α]$_D$+14.04° (c 0.99, DMSO).

SYNTHETIC EXAMPLE 3

Resolution of Compound of Formula (I) by SMB Chromatography

The compound of formula (I) was resolved into the (S)-enantiomer of the invention and the corresponding (R)-enantiomer by SMB chromatography under the following conditions:

Extract: 147.05 mL/min

Raffinate: 76.13 mL/min

Eluent: 183.18 mL/min

Feed: 40 mL/min

Recycling: 407.88 mL/min

Run Time: 0.57 min

Temperature: 25° C.

Pressure: 46 bar

The feed solution (25 g of compound of formula (I) in 1.0 L of mobile phase (25:75:0.1 (v:v:v) mixture of acetonitrile/methanol/trifluoroacetic acid)) was injected continuously into the SMB system (Novasep Licosep Lab Unit), which was equipped with eight identical columns in 2-2-2-2 configuration containing 110 g (per column, 9.6 cm, 4.8 cm I.D.) of ChiralPAK-AD as stationary phase. The first eluting enantiomer (the (R)-enantiomer of the compound of formula (I)) was contained in the raffinate stream and the second eluting enantiomer (the (S)-enantiomer of the compound of formula (I)) was contained in the extract stream. The characterization data of the (S)-enantiomer and the (R)-enantiomer obtained from the SMB resolution were identical to those obtained above utilizing chiral HPLC.

The compound of formula (I) was resolved into its constituent enantiomers on a Waters preparative LCMS autopurification system. The first-eluting enantiomer from the chiral column was brominated (at a site well-removed from the stereogenic centre) to give the corresponding 5'-bromo derivative, which was subsequently crystallized to generate a single crystal suitable for X-ray crystallography. The crystal structure of this brominated derivative of the first-eluting enantiomer was obtained and its absolute configuration was found to be the same as the (R)-enantiomer of the invention. Hence, the second-eluting enantiomer from the chiral column is the (S)-enantiomer of the invention. Moreover, the material obtained from the extract stream of the SMB resolution had a specific optical rotation of the same sign (positive, i.e. dextrorotatory) as that of the material obtained from the aforementioned LC resolution.

Biological Assays

Various techniques are known in the art for testing the activity of the compound of the invention or determining their solubility in known pharmaceutically acceptable excipients. In order that the invention described herein may be more fully understood, the following biological assays are set forth. It should be understood that these examples are for illustrative purposes only and are not to be construed as limiting this invention in any manner.

BIOLOGICAL EXAMPLE 1

Guanidine Influx Assay (In Vitro Assay)

This example describes an in vitro assay for testing and profiling test agents against human or rat voltage-gated sodium channels stably expressed in cells of either an endogenous or heterologously expressed origin. The assay is also useful for determining the IC$_{50}$ of a voltage-gated sodium channel modulating (preferably blocking) compound. The assay is based on the guanidine influx assay described by Reddy, N. L., et al., *J. Med. Chem.* (1998), 41(17):3298-302.

The guanidine influx assay is a radiotracer flux assay used to determine ion flux activity of voltage-gated sodium channels in a high-throughput microplate-based format. The assay uses $^{14}$C-guanidine hydrochloride in combination with various known voltage-gated sodium channel modulators that produce maintained influx, to assay the potency of test agents. Potency is determined by an IC$_{50}$ calculation. Selectivity is determined by comparing potency of the compound for the voltage-gated sodium channel of interest to its potency against other voltage-gated sodium channels (also called 'selectivity profiling').

Each of the test agents is assayed against cells that express the voltage-gated sodium channels of interest. Voltage-gated sodium channels are characterized as TTX sensitive or insensitive. This property is useful when evaluating the activities of a voltage-gated sodium channel of interest when it resides in a mixed population with other voltage-gated sodium channels. The following Table 1 summarizes cell lines useful in screening for a certain voltage-gated sodium channel activity in the presence or absence of TTX.

TABLE 1

| CELL LINE | mRNA Expression | Functional Characterization |
|---|---|---|
| CHO-K1 (Chinese Hamster Ovary; recommended host cell line) ATTC accession number CCL-61 | Na$_v$1.4 expression has been shown by RT-PCR No other Na$_v$ expression has been detected | The 18- to 20-fold increase in [$^{14}$C] guanidine influx was completely blocked using TTX. (Na$_v$1.4 is a TTX sensitive channel) |
| L6 (rat myoblast cell) ATTC Number CRL-1458 | Expression of Na$_v$1.4 and 1.5 | The 10- to 15-fold increase in [$^{14}$C] guanidine influx was only partially blocked by TTX at 100 nM (Na$_v$1.5 is TTX resistant) |
| SH-SY5Y (Human neuroblastoma) ATTC Number CRL-2266 | Published Expression of Na$_v$1.9 and Na$_v$1.7 (Blum et al.) | The 10- to 16-fold increase in [$^{14}$C] guanidine influx above background was partially blocked by TTX (Na$_v$1.9 is TTX resistant) |
| SK-N-BE2C (a human neuroblastoma cell line ATCC Number CRL-2268) | Expression of Na$_v$1.8 | Stimulation of BE2C cells with pyrethroids results in a 6-fold increase in [$^{14}$C] guanidine influx above background. TTX partially blocked influx (Na$_v$1.8 is TTX resistant) |
| PC12 (rat pheochromocytoma) ATTC Number CRL-1721 | Expression of Na$_v$1.2 and Na$_v$1.7 | The 8- to 12-fold increase in [$^{14}$C] guanidine influx was completely blocked using TTX. (Na$_v$1.2 and Na$_v$1.7 are TTX sensitive channels) |
| HEK293 (human embryonic kidney) ATTC Number CRL-1573 | Expression of hNa$_v$1.7 | Nav1.7 is a TTX sensitive channel. The TTX IC$_{50}$ in the functional Guanidinium assay is 8 nM. |

It is also possible to employ immortalized cell lines that heterologously express voltage-gated sodium channels. Cloning, stable transfection and propagation of such cell lines are known to those skilled in the art (see, for example, Klugbauer, N, et al., *EMBO J.* (1995), 14(6):1084-90; and Lossin, C., et al., *Neuron* (2002), 34, pp. 877-884).

Cells expressing the voltage-gated sodium channel of interest are grown according to the supplier or in the case of a recombinant cell in the presence of selective growth media such as G418 (Gibco/Invitrogen). The cells are disassociated from the culture dishes with an enzymatic solution (1×) Trypsin/EDTA (Gibco/Invitrogen) and analyzed for density and viability using haemocytometer (Neubauer). Disassociated cells are washed and resuspended in their culture media then plated into Poly-D-Lysine coated Scintiplates (Perkin Elmer) (approximately 100,000 cells/well) and incubated at 37° C./5% CO$_2$. for 20-24 hours. After an extensive wash with Low sodium HEPES-buffered saline solution (LNHBSS) (150 mM Choline Chloride, 20 nM HEPES (Sigma), 1 mM Calcium Chloride, 5 mM Potassium Chloride, 1 mM Magnesium Chloride, 10 mM Glucose) the test agents are diluted with LNHBSS and then added to each well at the desired concentration. (Varying concentrations of test agent may be used). The activation/radiolabel mixture contains an alkaloid such as veratridine or Aconitine (Sigma) or a pyrethroid such as deltamethrin, venom from the scorpion Leiurus quinquestriatus hebraeus (Sigma) and $^{14}$C-guanidine hydrochloride (ARC) to measure flux through the voltage-gated sodium channels.

After loading the cells with test agent and activation/radiolabel mixture, the Poly-D-Lysine coated Scintiplates are incubated at ambient temperature. Following the incubation, the Poly-D-Lysine coated Scintplates are extensively washed with LNHBSS supplemented with Guanidine (Sigma). The Poly-D-Lysine coated Scintiplates are dried and then counted using a Wallac MicroBeta TriLux (Perkin-Elmer Life Sciences). The ability of the test agent to block voltage-gated sodium channel activity is determined by comparing the amount of $^{14}$C-guanidine present inside the cells expressing the different voltage-gated sodium channels. Based on this data, a variety of calculations, as set out elsewhere in this specification, may be used to determine whether a test agent is selective for a particular voltage-gated sodium channel.

The IC$_{50}$ value of a test agent for a specific voltage-gated sodium channel may be determined using the above general method. The IC$_{50}$ may be determined using a 3, 8, 10, 12 or 16 point curve in duplicate or triplicate with a starting concentration of 1, 5 or 10 µM diluted serially with a final concentration reaching the sub-nanomolar, nanomolar and low micromolar ranges. Typically the mid-point concentration of test agent is set at 1 µM, and sequential concentrations of half dilutions greater or smaller are applied (e.g. 0.5 µM; 5 µM and 0.25 µM; 10 µM and 0.125 µM; 20 µM etc.). The IC$_{50}$ curve is calculated using the 4 Parameter Logistic Model or Sigmoidal Dose-Response Model formula (fit=(A+((B−A)/(1+((C/x)^D)))).

The fold selectivity, factor of selectivity or multiple of selectivity, is calculated by dividing the IC$_{50}$ value of the test voltage-gated sodium channel by the reference voltage-gated sodium channel, for example, Na$_v$1.5.

Accordingly, the compound of formula (I), the (S)-enantiomer of the compound of formula (I), i.e., the (S)-enantiomer of the invention, and the (R)-enantiomer of the compound of formula (I), when tested in this assay, demonstrated voltage-gated sodium channel blocking activity against hNa$_v$1.7 as set forth below in Table 2:

TABLE 2

| Compound | Chemical Name | IC$_{50}$ (µM) |
|---|---|---|
| (I) | 1'-{[5-(trifluoromethyl)furan-2-yl]methyl}spiro[furo[2,3-f][1,3]benzodioxole-7,3'-indol]-2'(1'H)-one | 0.007 |
| (I-R) | (R)-1'-{[5-(trifluoromethyl)furan-2-yl]methyl}spiro[furo[2,3-f][1,3]benzodioxole-7,3'-indol]-2'(1'H)-one | 4.200 |
| (I-S) | (S)-1'-{[5-(trifluoromethyl)furan-2-yl]methyl}spiro[furo[2,3-f][1,3]benzodioxole-7,3'-indol]-2'(1'H)-one | 0.003 |

The concentration-response relationship for the (S)-enantiomer of the invention and the (R)-enantiomer is shown in FIG. 1. The solid curves indicate the least-squares best fit to a 1:1 binding isotherm; the $IC_{50}$'s that describe these curves are given in Table 2. The (S)-enantiomer of the invention demonstrated a significantly higher (i.e. >1000-fold) inhibition potency against $hNa_v1.7$ in this model when compared to the inhibition potency of the corresponding (R)-enantiomer.

These results favor the use of the (S)-enantiomer of the invention over the (R)-enantiomer or the compound of formula (I) (the racemate) for the utilities described herein in that a higher pharmacological activity may be achieved at lower dosage levels with possibly fewer side effects. Moreover, the (R)-enantiomer is a very important tool for safety studies because it allows one to distinguish between mechanism-based effects (those mediated by block of sodium channels) and off-target activities that can be eliminated in analogs without compromising efficacy. If an adverse effect is mechanism-based, then the (S)-enantiomer will be much more potent then the (R)-enantiomer, as secondary sites of action are unlikely to have identical stereoselectivity and the two enantiomers are likely to have similar effects, including potency, on secondary sites of action.

BIOLOGICAL EXAMPLE 2

Electrophysiological Assay (In Vitro Assay)

HEK293 Cells expressing $hNa_v1.7$ were cultured in DMEM growth media (Gibco) with 0.5 mg/mL G418, +/−1% PSG, and 10% heat-inactivated fetal bovine serum at 37° C. and 5% $CO_2$. For electrophysiological recordings, cells were plated on 10 mm dishes.

Whole cell recordings were examined by established methods of whole cell voltage clamp (Bean et al., op. cit.) using an Axopatch 200B amplifier and Clampex software (Axon Instruments, Union City, Calif.). All experiments were performed at ambient temperature. Electrodes were fire-polished to resistances of 2-4 Mohms Voltage errors and capacitance artifacts were minimized by series resistance compensation and capacitance compensation, respectively. Data were acquired at 40 kHz and filtered at 5 kHz. The external (bath) solution consisted of: NaCl (140 mM), KCl (5 mM), $CaCl_2$ (2 mM), $MgCl_2$ (1 mM), HEPES (10 mM) at pH 7.4. The internal (pipette) solution consisted of (in mM): NaCl (5), $CaCl_2$ (0.1), $MgCl_2$ (2), CsCl (10), CsF (120), HEPES (10), EGTA (10), at pH 7.2.

To estimate the steady-state affinity of compounds for the resting and inactivated state of the channel ($K_r$ and $K_i$, respectively), 12.5 ms test pulses to depolarizing voltages from −60 to +90 mV from a holding potential of −120 mV was used to construct current-voltage relationships (I-V curves). A voltage near the peak of the I V-curve (−30 to 0 mV) was used as the test pulse throughout the remainder of the experiment. Steady-state inactivation (availability) curves were then constructed by measuring the current activated during a 8.75 ms test pulse following 1 second conditioning pulses to potentials ranging from −120 to −10 mV.

The steady-state voltage-dependence of binding of a compound to a voltage-gated sodium channel was determined by measuring the blockage of the ionic current at two holding potentials. Binding to rested-state channels was determined by using a holding potential of −120 mV, so that maximal availability was achieved. Binding to inactivated-state channels was evaluated at a holding potential such that only about 10% of the channels were available to open. The membrane potential was held at this voltage for at least 10 seconds so that drug binding could equilibrate.

The apparent dissociation constant at each voltage was calculated with the equation:

$$\% \text{ inhibition} = \frac{[\text{Drug}]}{([\text{Drug}] + K_d)} \times 100$$

where $K_d$ is the dissociation constant (either $K_r$ or $K_i$), and [Drug] is the concentration of the test compound.

Accordingly, the compound of formula (I), the (S)-enantiomer of the compound of formula (I), i.e., the (S)-enantiomer of the invention, and the (R)-enantiomer of the compound of formula (I), when tested in this model, demonstrated affinities for the rested/closed state and the inactivated state of $hNa_v1.7$ as set forth below in Table 3:

TABLE 3

| Compound | Chemical Name | $K_i$ (µM) | $K_r$ (µM) |
|---|---|---|---|
| (I) | 1'-{[5-(trifluoromethyl)furan-2-yl]methyl}spiro[furo[2,3-f][1,3]benzodioxole-7,3'-indol]-2'(1'H)-one | 0.142 | >10 uM |
| (I-R) | (R)-1'-{[5-(trifluoromethyl)furan-2-yl]methyl}spiro[furo[2,3-f][1,3]benzodioxole-7,3'-indol]-2'(1'H)-one | 0.869 | >10 uM |
| (I-S) | (S)-1'-{[5-(trifluoromethyl)furan-2-yl]methyl}spiro[furo[2,3-f][1,3]benzodioxole-7,3'-indol]-2'(1'H)-one | 0.161 | >10 uM |

As demonstrated by these results, the (S)-enantiomer of the invention is a state- or voltage-dependent modifier of $hNa_v1.7$, having a low affinity for the rested/closed state and a high affinity for the inactivated state. The results demonstrated that the (S)-enantiomer was about 5 times more potent in binding to the inactivated-state of $hNa_v1.7$ than the (R)-enantiomer. Furthermore, the results demonstrated that the (S)-enantiomer is primarily responsible for the potency of the racemate, i.e., the compound of formula (I).

BIOLOGICAL EXAMPLE 3

In Vivo Assays

Acute Pain (Formalin Test)

The formalin test is used as an animal model of acute pain. In the formalin test, animals are briefly habituated to the plexiglass test chamber on the day prior to experimental day for 20 minutes. On the test day, animals are randomly injected with the test articles. At 30 minutes after drug administration, 50 µL of 10% formalin is injected subcutaneously into the plantar surface of the left hind paw of the rats. Video data acquisition begins immediately after formalin administration, for duration of 90 minutes.

The images are captured using the Actimetrix Limelight software which stores files under the *.llii extension, and then converts it into the MPEG-4 coding. The videos are then analyzed using behaviour analysis software "The Observer 5.1", (Version 5.0, Noldus Information Technology, Wageningen, The Netherlands). The video analysis is done by watching the animal behaviour and scoring each according to type, and defining the length of the behaviour (Dubuisson and Dennis, 1977). Scored behaviours include: (1) normal behaviour, (2) putting no weight on the paw, (3) raising the paw, (4) licking/biting or scratching the paw. Elevation, favoring, or excessive licking, biting and scratching of the injected paw indicate a pain response. Analgesic response or protection from compounds is indicated if both paws are resting on the floor with no obvious favoring, excessive licking, biting or scratching of the injected paw.

Analysis of the formalin test data is done according to two factors: (1) Percent Maximal Potential Inhibitory Effect (% MPIE) and (2) pain score. The % MPIEs is calculated by a series of steps, where the first is to sum the length of non-normal behaviours (behaviours 1,2,3) of each animal. A single value for the vehicle group is obtained by averaging all scores within the vehicle treatment group. The following calculation yields the MPIE value for each animal:

$$MPIE(\%) = 100 - [(\text{treatment sum/average vehicle value}) \times 100\%]$$

The pain score is calculated from a weighted scale as described above. The duration of the behaviour is multiplied by the weight (rating of the severity of the response), and divided by the total length of observation to determine a pain rating for each animal. The calculation is represented by the following formula:

$$\text{Pain rating} = [0(T_0) + 1(T_1) + 2(T_2) + 3(T_3)] / (T_0 + T_1 + T_2 + T_3)$$

CFA Induced Chronic Inflammatory Pain

In this test, tactile allodynia is assessed with calibrated von Frey filaments. Following a full week of acclimatization to the vivarium facility, 150 µL of the "Complete Freund's Adjuvant" (CFA) emulsion (CFA suspended in an oil/saline (1:1) emulsion at a concentration of 0.5 mg/mL) was injected subcutaneously into the plantar surface of the left hind paw of rats under light isoflurane anaesthesia. Animals were allowed to recover from the anaesthesia and the baseline thermal and mechanical nociceptive thresholds of all animals were assessed one week after the administration of CFA. All animals were habituated to the experimental equipment for 20 minutes on the day prior to the start of the experiment. The test and control articles were administered to the animals, and the nociceptive thresholds were measured at defined time points after drug administration to determine the analgesic responses to each of the six available treatments. The time points used were previously determined to show the highest analgesic effect for each test compound.

Figure 2:
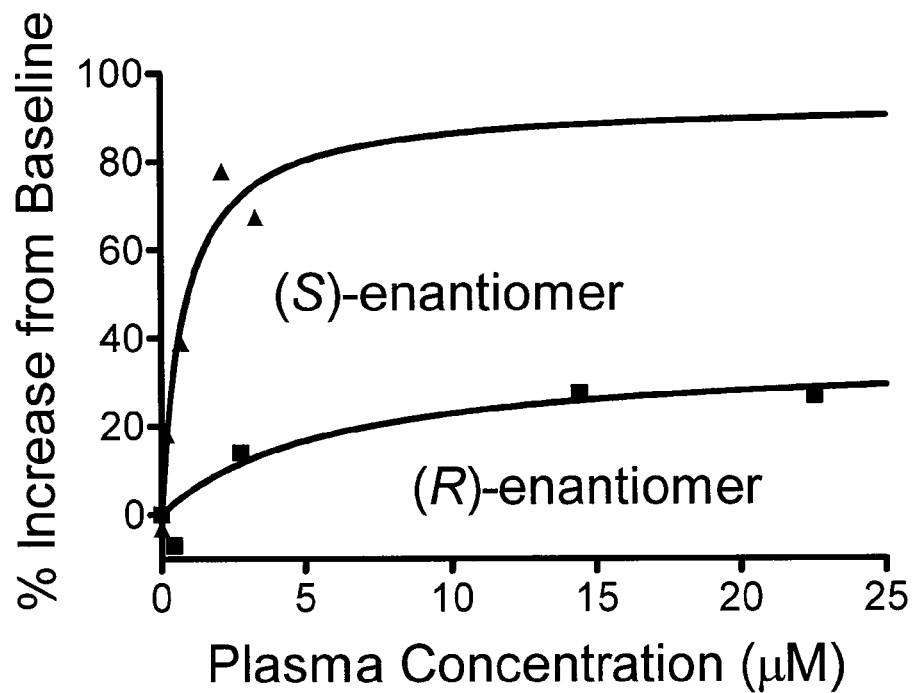
FIG. 2 shows comparison of the efficacy of the (S)- and (R)-enantiomers with oral dosing in an inflammatory pain model from Biological Example 3 herein.

The (S)-enantiomer of the invention and the corresponding (R)-enantiomer were compared using both oral and topical dosing. FIG. 2 shows a comparison of the efficacy of the (S)-enantiomer of the invention and the (R)-enantiomer with oral dosing. Each enantiomer was dosed at 10, 30, 100 or 200 mg/Kg. The plasma concentration achieved with each dose was also determined and the reversal of pain response (as the % increase from baseline threshold) is plotted as a function of plasma concentration.

The (S)-enantiomer had a greater maximal effect when dosed at 200 mg/Kg. The (R)-enantiomer achieved a much higher plasma concentration at an equivalent dose level. This was an unexpected and unusual finding. As a consequence, the use of the racemate, i.e., the compound of formula (I), would result in about a 10-fold excess of the inactive enantiomer, e., the (R)-enantiomer. Accordingly, the use of the (S)-enantiomer of the invention would greatly improved the likelihood of obtaining efficacy with minimal chance of encountering off-target activities that are not stereoselective.

The (S)-enantiomer of the invention was also administered topically to the animals in varying dosages (1%, 2%, 4% and 8% (w/v)) and the nociceptive thresholds measured at defined time points after drug administration to determine the analgesic responses to each of the available treatments. The time points used were previously determined to show the highest analgesic effect for each test compound.

The response thresholds of the animals to tactile stimuli were measured using the Model 2290 Electrovonfrey anesthesiometer (IITC Life Science, Woodland Hills, Calif.) following the Hargreaves test. The animals were placed in an elevated Plexiglas enclosure set on a wire mesh surface. After 15 minutes of accommodation, a pre-calibrated Von Frey hair was applied perpendicularly to the plantar of the ipsilateral hind paws of the animals, with sufficient force, measured in grams, to elicit a crisp response of the paw. The response indicated a withdrawal from the painful stimulus and constituted the efficacy endpoint. Testing continues until the hair with the lowest force to induce a rapid flicking of the paw was determined or when the cut off force of approximately 20 g was reached. This cut off force is used because it represent approximately 10% of the animals' body weight and it serves to prevent raising of the entire limb due to the use of stiffer hairs, which would change the nature of the stimulus. The data were expressed as percent increase from baseline threshold measured in grams.

The (S)-enantiomer of the invention, when tested in this model, demonstrated an analgesic effect as set forth below in Table 4.

TABLE 4

| Compound | % Increase From Base Line (CFB) | | | |
|---|---|---|---|---|
|  | 1% topical | 2% topical | 4% topical | 8% topical |
| (I-S) | 0.62 | 16.71 | 28.79 | 45.06 |

The (S)-enantiomer of the invention at 2%, 4% and 8% (w/v) showed increases in the von Frey mechanical paw withdrawal thresholds as expressed by percent increase from baseline (IFB) to indicate an analgesic effect. The analgesic effect for the (S)-enantiomer increased with increasing doses up to the highest dose tested of 8% (w/v), which showed the maximum percent IFB at +45.1%. The 1% (w/w) dosage group, however, did not demonstrate an observable increase in von Frey mechanical paw withdrawal threshold. The results indicate that the (S)-enantiomer have analgesic effects in the CFA-induced inflammatory pain model in the range of 2% to 8% (w/v).

Postoperative Models of Nociception

In this model, the hypealgesia caused by an intra-planar incision in the paw is measured by applying increased tactile stimuli to the paw until the animal withdraws its paw from the applied stimuli. While animals are anaesthetized under 3.5% isofluorane, which is delivered via a nose cone, a 1 cm longitudinal incision was made using a number 10 scalpel blade in the plantar aspect of the left hind paw through the skin and fascia, starting 0.5 cm from the proximal edge of the heel and extending towards the toes. Following the incision, the skin is apposed using 2, 3-0 sterilized silk sutures. The injured site is covered with Polysporin and Betadine. Animals are returned to their home cage for overnight recovery.

The withdrawal thresholds of animals to tactile stimuli for both operated (ipsilateral) and unoperated (contralateral) paws can be measured using the Model 2290 Electrovonfrey anesthesiometer (IITC Life Science, Woodland Hills, Calif.). Animals are placed in an elevated Plexiglas enclosure set on a mire mesh surface. After at least 10 minutes of acclimatization, pre-calibrated Von Frey hairs are applied perpendicularly to the plantar surface of both paws of the animals in an ascending order starting from the 10 g hair, with sufficient force to cause slight buckling of the hair against the paw. Testing continued until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Neuropathic Pain Model; Chronic Constriction Injury

In this model, an approximately 3 cm incision was made through the skin and the fascia at the mid thigh level of the animals' left hind leg using a no. 10 scalpel blade. The left sciatic nerve was exposed via blunt dissection through the biceps femoris with care to minimize haemorrhagia. Four loose ligatures were tied along the sciatic nerve using 4-0 non-degradable sterilized silk sutures at intervals of 1 to 2 mm apart. The tension of the loose ligatures is tight enough to induce slight constriction of the sciatic nerve when viewed under a dissection microscope at a magnification of 4 fold. In the sham-operated animal, the left sciatic nerve was exposed without further manipulation. Antibacterial ointment was applied directly into the wound, and the muscle was closed using sterilized sutures. Betadine was applied onto the muscle and its surroundings, followed by skin closure with surgical clips.

The response thresholds of animals to tactile stimuli were measured using the Model 2290 Electrovonfrey anesthesiometer (IITC Life Science, Woodland Hills, Calif.). Animals were placed in an elevated Plexiglas enclosure set on a mire mesh surface. After 10 minutes of accommodation, pre-calibrated Von Frey hairs were applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represents approximately 10% of the animals' body weight and it serves to prevent raising of the entire limb due to the use of stiffer hairs, which would change the nature of the stimulus.

Thermal nociceptive thresholds of the animals were assessed using the Hargreaves test. Following the measurement of tactile thresholds, animals were placed in a Plexiglass enclosure set on top of an elevated glass platform with heating units. The glass platform was thermostatically controlled at a temperature of approximately 24 to 26° C. for all test trials. Animals were allowed to accommodate for 10 minutes following placement into the enclosure until all exploration behaviour ceases. The Model 226 Plantar/Tail Stimulator Analgesia Meter (IITC, Woodland Hills, Calif.) was used to apply a radiant heat beam from underneath the glass platform to the plantar surface of the hind paws. During all test trials, the idle intensity and active intensity of the heat source were set at 1 and 55 respectively, and a cut off time of 20 seconds was used to prevent tissue damage.

Figure 3:
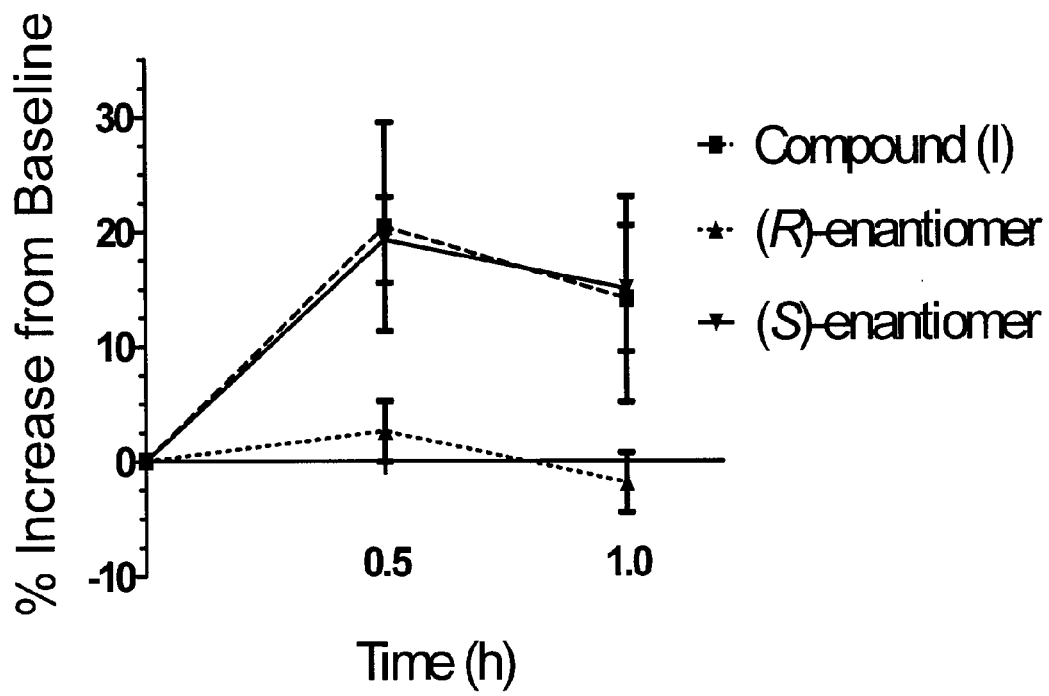
FIG. 3 shows comparison of the efficacy of the (S)- and (R)-enantiomers with topical administration in a neuropathic pain model from Biological Example 3 herein.

The (S)-enantiomer was compared with the corresponding (R)-enantiomer and racemate (compound of formula (I)) in this CCI model using topical application of drug, as described for the CFA model (see FIG. 3). Each test compound was administered as an ointment containing 2% (w/v). Consistent with the differing activities of these two enantiomers as voltage-gated sodium channel inhibitors, only the (S)-enantiomer of the invention reversed pain responses while the (R)-enantiomer had no significant increase from baseline. Both the (S)-enantiomer and the racemate show similar percent increase from baseline which tend to suggest that the (S)-enantiomer is responsible for the analgesic affect.

BIOLOGICAL EXAMPLE 4

Aconitine Induced Arrhythmia Assay

The antiarrhythmic activity of compounds of the invention is demonstrated by the following test. Arrhythmia is provoked by intravenous administration of aconitine (2.0 µg/Kg) dissolved in physiological saline solution. Test compounds of the invention are intravenously administered 5 minutes after the administration of aconitine. Evaluation of the anti-arrhythmic activity is conducted by measuring the time from the aconitine administration to the occurrence of extrasystole (ES) and the time from the aconitine administration to the occurrence of ventricular tachycardia (VT).

In rats under isoflurane anaesthesia (1/4 to 1/3 of 2%), a tracheotomy is performed by first creating an incision in the neck area, then isolating the trachea and making a 2 mm incision to insert tracheal tube 2 cm into the trachea such that the opening of the tube is positioned just on top of the mouth. The tubing is secured with sutures and attached to a ventilator for the duration of the experiment.

Incisions (2.5 cm) are then made into the femoral areas and using a blunt dissection probe, the femoral vessels are isolated. Both femoral veins are cannulated, one for pentobarbital anaesthetic maintenance (0.02-0.05 mL) and one for the infusion and injection of drug and vehicle. The femoral artery is cannulated with the blood pressure gel catheter of the transmitter.

The ECG leads are attached to the thoracic muscle in the Lead II position (upper right/above heart—white lead and lower left/below heart—red lead). The leads are secured with sutures.

All surgical areas are covered with gauze moistened with 0.9% saline. Saline (1-1.5 mL of a 0.9% solution) is supplied to moisten the areas post-surgery. The animals' ECG and ventilation are allowed to equilibrate for at least 30 minutes.

The arrhythmia is induced with a 2 µg/Kg/min aconitine infusion for 5 minutes. During this time the ECG is recorded and continuously monitoired.

BIOLOGICAL EXAMPLE 5

Ischemia Induced Arrhythmia Assay

Rodent models of ventricular arrhythmias, in both acute cardioversion and prevention paradigms have been employed in testing potential therapeutics for both atrial and ventricular arrhythmias in humans. Cardiac ischemia leading to myocardial infarction is a common cause of morbidity and mortality. The ability of a compound to prevent ischemia-induced ventricular tachycardia and fibrillation is an accepted model for determining the efficacy of a compound in a clinical setting for both atrial and ventricular tachycardia and fibrillation.

Anaesthesia is first induced by pentobarbital (i.p.), and maintained by an i.v. bolus infusion. Male SD rats have their trachea cannulated for artificial ventilation with room air at a stroke volume of 10 mL/Kg, 60 strokes/minute. The right femoral artery and vein are cannulated with PE50 tubing for mean arterial blood pressure (MAP) recording and intravenous administration of compounds, respectively.

The chest is opened between the $4^{th}$ and $5^{th}$ ribs to create a 1.5 cm opening such that the heart was visible. Each rat is placed on a notched platform and metal restraints are hooked onto the rib cage opening the chest cavity. A suture needle is used to penetrate the ventricle just under the lifted atrium and exited the ventricle in a downward diagonal direction so that a >30% to <50% occlusion zone (OZ) would be obtained. The exit position is ~0.5 cm below where the aorta connects to the left ventricle. The suture is tightened such that a loose loop (occluder) is formed around a branch of the artery. The chest is then closed with the end of the occluder accessible outside of the chest.

Electrodes are placed in the Lead II position (right atrium to apex) for ECG measurement as follows: one electrode is inserted into the right forepaw and the other electrode is inserted into the left hind paw.

The body temperature, mean arterial pressure (MAP), ECG, and heart rate are constantly recorded throughout the experiment. Once the critical parameters have stabilized, a 1-2 minute recording is taken to establish the baseline values. Infusion of a compound of the invention or control substance is initiated once baseline values are established. After a 5-minute infusion of compound or control, the suture is pulled tight to ligate the LCA and create ischemia in the left ventricle. The critical parameters are recorded continuously for 20 minutes after ligation, unless the MAP reaches the critical level of 20-30 mm Hg for at least 3 minutes, in which case the recording is stopped because the animal would be declared deceased and is then sacrificed. The ability of compounds of the invention to prevent arrhythmias and sustain near-normal MAP and HR is scored and compared to control.

BIOLOGICAL EXAMPLE 6

Compared to the racemate, i.e., the compound of formula (I), the (S)-enantiomer, substantially free of the (R)-enantiomer, has a better solubility profile in a variety of pharmaceutically acceptable excipients. Thus, the (S)-enantiomer can be formulated in a fewer number of dosage units than the racemate. This property facilitates dosing patients at a higher level if needed to achieve efficacy. Examples of the difference in solubility are shown in Table 5 below:

TABLE 5

| Excipient | Compound of formula (I) (racemate) | (S)-enantiomer |
| --- | --- | --- |
| Labrasol ® | 72.5 mg/mL | 231 mg/mL |
| Propylene glycol | 2.7 mg/mL | 9.8 mg/mL |
| PEG 400 | <50 mg/mL | >55 mg/mL |
| Capryol ® 90 | 18.1 mg/mL | 96 mg/mL |
| Tween ® 80 | 64 mg/mL | >123 mg/mL |
| Ethanol | 10.0 mg/mL | 36.4 mg/mL |
| Labrasol ®/PEG 400 60/40 | 70.4 mg/mL | 182 mg/mL |
| Labrasol ®/Capryol ® 90 60/40 | 44.4 mg/mL | 191 mg/mL |
| Labrasol ®/Transcutol ® 60/40 | 74.2 mg/mL | 186 mg/mL |

BIOLOGICAL EXAMPLE 7

In Vivo Assay for Treatment of Pruritis

Histamine induces pruritis (itching) in humans. Accordingly, this assay evaluates the efficacy of topically and orally administered (S)-enantiomer of the invention on histamine-induced pruritis in male ICR mice.

The animals were randomly divided into test groups including an untreated group, a group treated with a topical pharmaceutical composition with 8% (w/v) (S)-enantiomer, and a group treated with an oral pharmaceutical composition of 50 mg/Kg (S)-enantiomer. One day prior to testing, the scapular regions on the animals were shaved with hair clippers. On the testing day, the animals were habituated for 60 minutes in the test chamber comprising of a clear plastic tube placed vertically on a flat surface. After the habituation period, the animals were removed from the plastic tube, placed in a restrainer, and injected with histamine at the shaved scapular region. The injections were made intradermally into the skin in small injection volumes (10 µL) using a Hamilton syringe. The injection solutions consisted of histamine dissolved in saline at a concentration of 100 µg/10 µL (or 10 mg/mL). 10 µg of the solution was injected into each mouse. Immediately after the injections, the animals were returned to the test chambers and observed by cameras placed above the test chambers for a total of 50 minutes. The cameras were connected to a computer where digital video files were created, saved, and analyzed.

The number of itching bouts was scored over 40 minutes. An "itching bout" was defined as the lifting of a hind leg, using it to scratch the scapular region, and then placing it back on the ground. Alternatively, if instead of placing the hind leg back on the ground the mouse was observed to lick the paw, then that too was counted as an itching bout.

To the untreated group, animals (n=7) were habituated in the test chamber for 60 minutes prior to the histamine injection. To evaluate topical (S)-enantiomer in the histamine-induced pruritis, animals (n=16/group) were habituated in the test chamber for 30 minutes, followed by the application of 50 mg of 8% (w/v) topical (S)-enantiomer or vehicle to the shaved region on the back. The animals were returned to the test chamber for another 30 minutes of habituation prior to the injection of histamine. To evaluate oral (S)-enantiomer, animals (n=8/group) were dosed by oral gavage with 50 mg/Kg (S)-enantiomer or vehicle followed by habituation in the test chamber for 60 minutes prior to the histamine injection.

The data were analyzed using GraphPad Prism 5 statistical analysis software and an unpaired t-test was used for univariate analysis. Results are expressed as mean±SEM. Values that reached a p<0.05 level of significance were considered statistically significant.

Results

Figure 4:
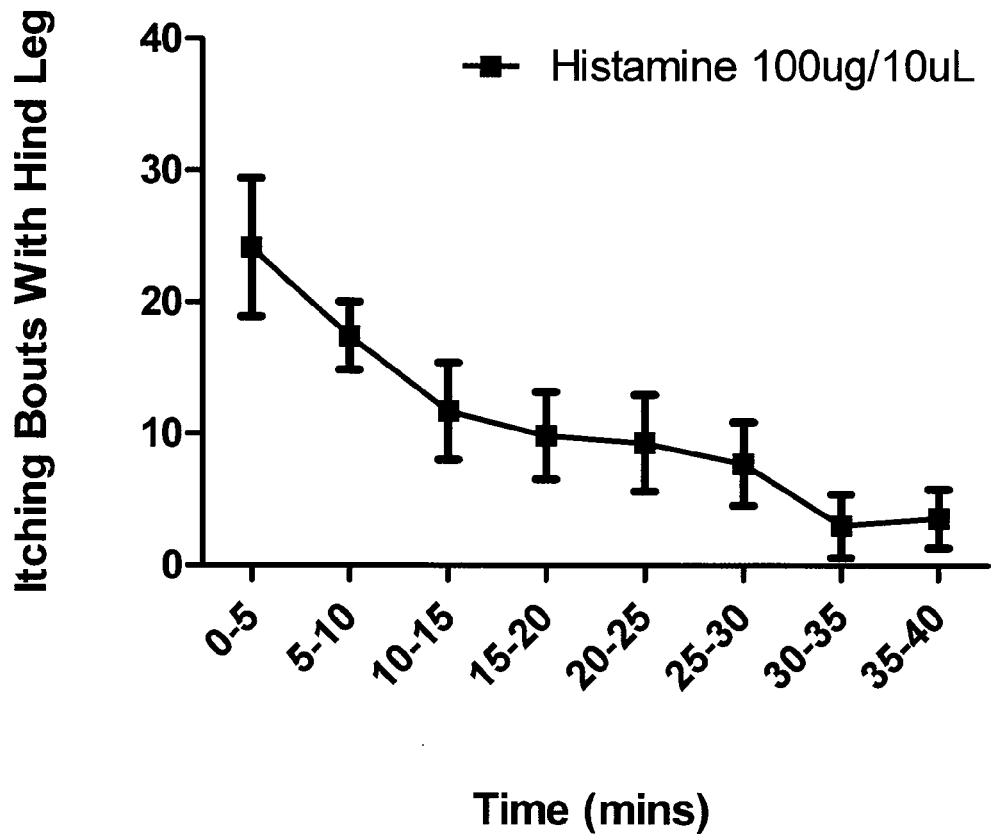
FIG. 4 shows the time course of histamine-induced itching in untreated mice in the in vivo assay described in Biological Example 7. Data are expressed as Mean±SD itching bouts.
Figure 5:
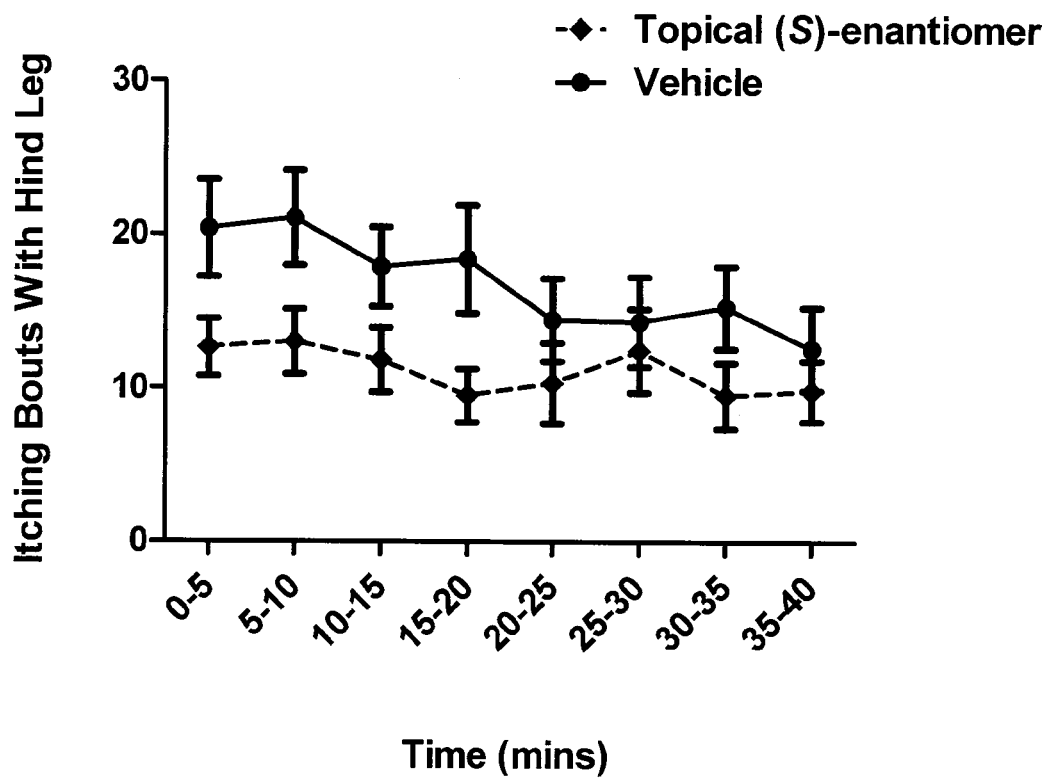
FIG. 5 shows the efficacy against histamine-induced itch of a topically applied ointment containing 8% (w/v) of the (S)-enantiomer. Data are expressed as Mean±SD itching bouts.
Figure 6:
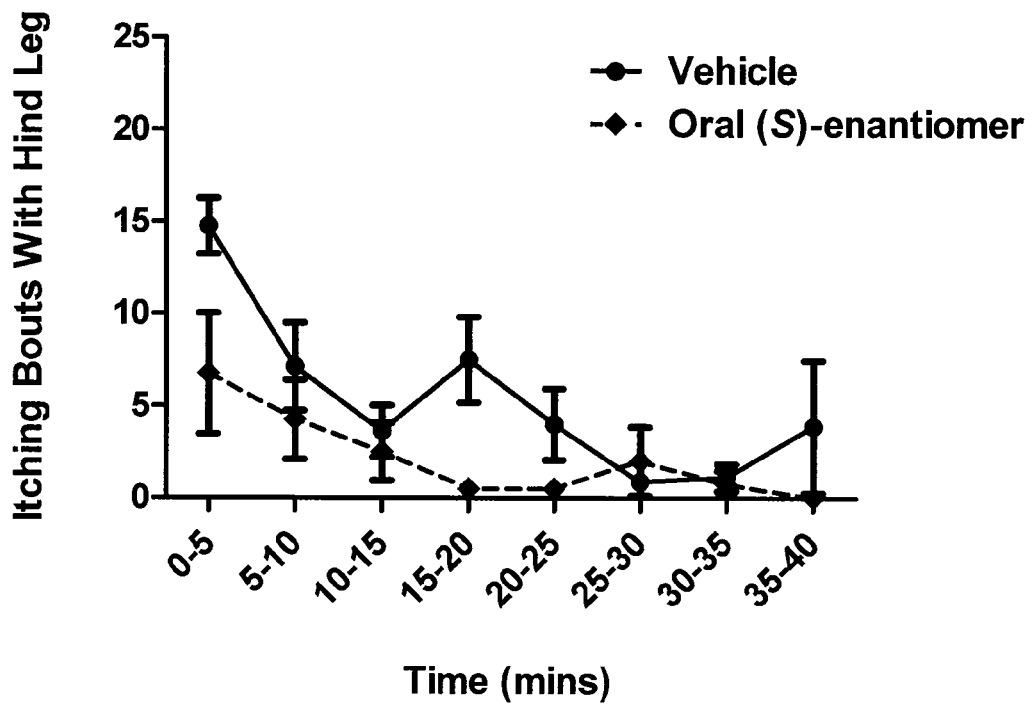
FIG. 6 shows the efficacy of the (S)-enantiomer against histamine-induced itch when administered orally rather than topically. Data are expressed as Mean±SD itching bouts.

The injection of histamine into the skin caused the animals to itch sporadically in bouts that lasted 1-2 seconds. In the untreated group, itching bouts began immediately post-injection and lasted for roughly 40 minutes thereafter (see FIG. 4). The group treated with 8% (w/v) of topical (S)-enantiomer showed significantly reduced pruritis (see FIG. 5). Animals treated with the vehicle only had a total number of 134.3±13.31 (n=16) itching bouts whereas mice treated with topical (S)-enantiomer had 89.00±10.51 (n=16) itching bouts. The difference between these groups was statistically significant with a p value of 0.0122. The group treated with 50 mg/Kg oral (S)-enantiomer similarly showed significantly reduced pruritis (see FIG. 6). Animals treated with vehicle only had a total number of 42.88±6.667 (n=8) itching bouts whereas mice treated with (S)-enantiomer had 17.25±6.310 (n=8) itching bouts. The difference between the orally-treated groups was also statistically significant with a p value of 0.0144. The results demonstrated that orally and topically administered (S)-enantiomer reduced pruritis. Furthermore, it is apparent that two common modes of drug delivery, oral and topical, can be used to deliver the (S)-enantiomer to achieve this therapeutic effect.

BIOLOGICAL EXAMPLE 8

Clinical Trial in Humans for the Treatment of Primary/Inherited Erythromelalgia (IEM)

Primary/Inherited Erythromelalgia (IEM) is a rare inherited pain condition. The underlying cause of IEM can be one or more gain-of-function mutation(s) in the $Na_v1.7$ voltage-gated sodium channel, which the (S)-enantiomer of the invention has been shown to inhibit.

Human patients with IEM have recurrent episodes of intense burning pain associated with redness and warmth in the hands and feet, but eventually the pain becomes constant. The pain is relieved by cooling, but has been largely resistant to pharmacological intervention. However, there are reports of voltage-gated sodium channel blockers showing moderate to outstanding pain relief for this condition.

A clinical trial for determining the efficacy of the (S)-enantiomer of the invention in ameliorating or alleviating IEM can be designed to be a three-period, double-blind, multiple-dose, and crossover study to minimize the dropout rate of participants, and will take into consideration that the patients enrolled will only be available for a 10-day study. Each patient enrolled in the study will serve as their own control, receiving both placebo and 400 mg of the (S)-enantiomer of the invention twice daily in a cross-over fashion.

BIOLOGICAL EXAMPLE 9

Clinical Trial in Humans for Treatment of Dental Pain

The purpose of this clinical trial was to compare the safety and efficacy (onset, duration of relief, and overall efficacy) of a single 500 mg dose of the (S)-enantiomer of the invention versus placebo dose for relief of pain following extraction of impacted third molar teeth.

Sixty-one subjects were enrolled in the study. The mean age for the subjects was 20.4 years, and all subjects were male. The majority of subjects were Caucasians (95.1%).

The severity and relief of the pain was measured using an 11-point Pain Intensity Numerical Rating Scale (graded from 0=no pain at all to 10=worst pain imaginable) (PINRS) and a 5-point Categorical Pain Relief Scale (REL). Subjects completed the PINRS after surgery, but before the administration of (S)-enantiomer of the invention. Efficacy variables were derived from the REL and PINRS scores and included total pain relief (TOTPAR), pain intensity difference (PID), and summed pain intensity difference (SPID) and evaluated at time points of 4, 6, 8, and 12 hours after administration of the (S)-enantiomer of the invention.

However, the primary and all secondary endpoints showed a consistent analgesic trend with distinct separation of the (S)-enantiomer from placebo. These results suggest that the (S)-enantiomer has analgesic properties, but statistical significance from the placebo was not achieved due to two main reasons: (1) relatively high placebo response rate and (2) the slow onset of action of the (S)-enantiomer. The dental model utilized is designed and best suited for the evaluation of drugs with rapid onset such as the NSAID class of antiinflammatory agents. It was evident from this study that the (S)-enantiomer of the invention did not have such a NSAID-like rapid onset of action. However, the pain relief demonstrated by those subjects who received the (S)-enantiomer was higher compared to those subjects who only received the placebo, sufficiently so that the total efficacy population showed a consistent analgesic signal for all endpoints evaluated.

BIOLOGICAL EXAMPLE 10

Clinical Trial in Humans for the Safety of the (S)-Enantiomer of the Invention

This clinical trial was a Phase 1, randomised, double-blind, placebo-controlled study in healthy subjects to evaluate the safety and pharmacokinetics of topically applied ointment containing the (S)-enantiomer of the invention.

The (S)-enantiomer ointment was applied daily for 21 consecutive days to determine the local skin toxicity/irritancy of the (S)-enantiomer. Systemic pharmacokinetics and local skin drug levels were also assessed. The systemic exposure to the (S)-enantiomer following topical applications and local skin irritation following multiple-doses of the (S)-enantiomer ointment were evaluated. Each subject received 5 treatments for 21 consecutive days: (S)-enantiomer as ointment with 4% and 8% (w/w) (1×100 µL; Treatments A and B, respectively), placebo as ointment (Treatment C), saline (0.9%) solution (1×100 µL; negative control; Treatment D), and sodium-lauryl-sulphate (SLS) 0.1% solution (1×100 µL; positive control; Treatment E). The treatments were applied on two different sites on each subject's upper back in an occluded manner (five treatments) and partially occluded manner (first three treatments). The location for each treatment on each site (Treatments A, B, C, D, and E on occluded site and Treatments A, B, and C on partially occluded site) was randomised. Subjects were confined to the clinical research facility from approximately 18 hours prior to the first dosing on Day 1 until approximately 8 hours post-$2^{rd}$ dose (Day 2). Subjects came back each day for 19 consecutive days (Days 3 to 21) for dosing and study procedures.

No Serious Adverse Events (SAEs) or deaths were reported. All Adverse Events (AEs) were mild or moderate in severity, with the majority of AEs related to local skin reactions from the surgical tape used to adhere the occlusive dressings. All subjects reacted to the positive control. The positive control was stopped in all subjects on Day 4 following complaints of excessive discomfort from the subjects. Skin irritation scores were low for all treatments administered (maximum score of 3 measured on a scale of 0-7) indicating that (S)-enantiomer ointment was locally well tolerated. No difference was observed between cumulative irritation scores for (S)-enantiomer 4% (w/w), (S)-enantiomer 8% (w/w), placebo ointments and the negative control (0.9% saline). Signs of irritation had completely resolved by Day 28 (7 days following the final dose) for the majority of subjects.

Electrocardiography tracings did not demonstrate clinically significant changes in pulse rate, quiescent resting state, or $QT_c$ intervals of the subjects and no clinically significant changes from baseline were observed in the subjects' vital signs, physical examinations, or laboratory assessments. Systemic exposure to (S)-enantiomer was negligible, as (S)-enantiomer concentrations in plasma were below the lower limit of quantification (LLOQ) (0.1 ng/mL or 100 pg/mL) in most samples (489 out of 546=~90%). The highest level of (S)-enantiomer observed in one subject during the dosing period (Day 22) was 994 pg/mL. Based on the minimal local irritation and favourable safety profile, together with low (S)-enantiomer systemic exposure, it was concluded that the (S)-enantiomer of the invention was well tolerated and safe as a topical analgesic.

BIOLOGICAL EXAMPLE 11

Clinical Trial in Humans for Treatment of Post-Herpetic Neuralgia

Post Herpetic Neuralgia (PHN) is a well established and well recognized model for studying neuropathic pain. Furthermore, PHN demonstrates strong evidence of sodium channel blocker efficacy. The following study represents a randomized, double-blind, placebo-controlled, two-treatment, two-period cross-over study to evaluate the safety, tolerability, preliminary efficacy and systemic exposure of the (S)-enantiomer of the invention topically administered to patients with PHN. The primary objectives are (a) to compare the safety and efficacy of an ointment containing the (S)-enantiomer to that of placebo for the relief of pain in patients with PHN, and (b) to evaluate the extent of systemic exposure of the (S)-enantiomer following topical application of (S)-enantiomer in patients with PHN. The treatments will consist of (S)-enantiomer 8% (w/w) ointment and the matching placebo ointment.

The study will include the following four periods:
1. An initial screening and washout period (up to 3 weeks);
2. A single-blind, placebo run-in period (1 week);
3. A cross-over treatment period that will consist of 2 treatment periods each lasting 3 weeks separated by 2 weeks of washout/single-blind placebo run-in (total of 8 weeks); and
4. A safety follow-up period (2 weeks).

\* \* \* \* \*

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. The (S)-enantiomer of 1'-{[5-(trifluoromethy)furan-2-yl]methyl}spiro[furo[2,3-f][1,3]benzodioxole-7,3'-indol]-2'(1'H)-one having the following formula (I-S):

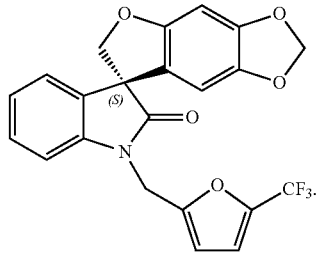

(I-S)

2. A pharmaceutical composition comprising a pharmaceutically acceptable excipient and the (S)-enantiomer of claim 1.

3. A method of treating post-herpetic neuralgia in a mammal, wherein the method comprises administering to the mammal in need thereof a therapeutically effective amount of the (S)-enantiomer of claim 1.

\* \* \* \* \*